US008652467B2

(12) United States Patent
Markovitz et al.

(10) Patent No.: US 8,652,467 B2
(45) Date of Patent: Feb. 18, 2014

(54) DEK PROTEIN COMPOSITIONS AND METHODS OF USING THE SAME

(75) Inventors: David M. Markovitz, Ann Arbor, MI (US); Nirit Mor-Vaknin, Ann Arbor, MI (US); Michael Khodadoust, Ann Arbor, MI (US); Barbara S. Adams, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 1222 days.

(21) Appl. No.: 12/090,164

(22) PCT Filed: Oct. 16, 2006

(86) PCT No.: PCT/US2006/041010
§ 371 (c)(1),
(2), (4) Date: Sep. 9, 2008

(87) PCT Pub. No.: WO2007/047907
PCT Pub. Date: Apr. 26, 2007

(65) Prior Publication Data
US 2009/0004197 A1    Jan. 1, 2009

Related U.S. Application Data

(60) Provisional application No. 60/726,674, filed on Oct. 14, 2005.

(51) Int. Cl.
*A61K 39/395* (2006.01)
(52) U.S. Cl.
USPC .................. 424/130.1; 424/133.1; 424/141.1; 424/156.1
(58) Field of Classification Search
None
See application file for complete search history.

(56) References Cited

U.S. PATENT DOCUMENTS

| | | | |
|---|---|---|---|
| 4,109,496 A | 8/1978 | Allemann et al. |
| 4,323,546 A | 4/1982 | Crockford et al. |
| 4,968,103 A | 11/1990 | McNab et al. |
| 4,981,785 A | 1/1991 | Nayak et al. |
| 5,034,506 A | 7/1991 | Summerton et al. |
| 5,223,409 A | 6/1993 | Ladner et al. |
| 5,283,317 A | 2/1994 | Saifer et al. |
| 5,358,691 A | 10/1994 | Clark et al. |
| 5,489,677 A | 2/1996 | Sanghvi et al. |
| 5,538,848 A | 7/1996 | Livak et al. |
| 5,539,082 A | 7/1996 | Nielsen et al. |
| 5,565,332 A | 10/1996 | Hoogenboom et al. |
| 5,585,089 A | 12/1996 | Queen et al. |
| 5,599,677 A | 2/1997 | Dowell et al. |
| 5,602,240 A | 2/1997 | De Mesmaeker et al. |
| 5,631,169 A | 5/1997 | Lakowicz et al. |
| 5,639,606 A | 6/1997 | Willey et al. |
| 5,643,765 A | 7/1997 | Willey et al. |
| 5,672,480 A | 9/1997 | Dowell et al. |
| 5,705,188 A | 1/1998 | Junichi et al. |
| 5,714,331 A | 2/1998 | Buchardt et al. |
| 5,719,262 A | 2/1998 | Buchardt et al. |
| 5,824,544 A | 10/1998 | Armentano et al. |
| 5,830,730 A | 11/1998 | German et al. |
| 5,872,154 A | 2/1999 | Wilson et al. |
| 5,876,978 A | 3/1999 | Willey et al. |
| 5,885,530 A | 3/1999 | Babson et al. |
| 5,885,808 A | 3/1999 | Spooner et al. |
| 5,981,225 A | 11/1999 | Kochanek et al. |
| 5,994,106 A | 11/1999 | Kovesdi et al. |
| 5,994,128 A | 11/1999 | Fallaux et al. |
| 5,994,132 A | 11/1999 | Chamberlain et al. |
| 6,001,557 A | 12/1999 | Wilson et al. |
| 6,019,978 A | 2/2000 | Ertl et al. |
| 6,033,908 A | 3/2000 | Bout et al. |
| 6,054,297 A | 4/2000 | Carter et al. |
| 6,159,750 A | 12/2000 | Edmonds |
| 6,180,370 B1 | 1/2001 | Queen et al. |
| 6,198,107 B1 | 3/2001 | Seville |
| 6,897,069 B1 | 5/2005 | Jarvis et al. |
| 2003/0175734 A1 | 9/2003 | Kroes et al. |
| 2003/0219752 A1 | 11/2003 | Short et al. |
| 2004/0053876 A1 | 3/2004 | Turner et al. |

FOREIGN PATENT DOCUMENTS

| | | |
|---|---|---|
| WO | WO 9410300 | 5/1994 |
| WO | WO 9730731 | 8/1997 |
| WO | WO 9902685 | 1/1999 |
| WO | WO 0009675 | 2/2000 |
| WO | WO 0012738 | 3/2000 |
| WO | WO 0198537 | 12/2001 |
| WO | WO 03002598 | 1/2003 |

OTHER PUBLICATIONS

Adams et al., "DEk binding to class II MHC Y-box sequences is gene- and allele-specific" Arthritis Research & Therapy, 5(4), 2003, pp. R226-R233.*
Banic et al., "Effect of Cyclosporine in a Murine Model of Experimental Colitis" Digestive Diseases and Sciences, 47(6), Jun. 2002, pp. 1362-1368.*
Forero et al., "Juvenile Arthritis, HLA-A2 and Binding of DEK Oncogene-Peptides" Human Immunology, 59, 1998, pp. 443-450.*
Hegen et al., "Utility of animal models for identification of potential therapeutics for rheumatoid arthritis" Ann Rheum Dis, 67, 2008, pp. 1505-1515.*

(Continued)

*Primary Examiner* — Daniel E Kolker
*Assistant Examiner* — James Rogers
(74) *Attorney, Agent, or Firm* — Kirk J. Hogan; Casimir Jones S.C.

(57) ABSTRACT

The present invention relates to DEK protein compositions (e.g., antibodies, small molecule inhibitors, siRNAs) and methods of using the same. In particular, the present invention provides compositions and methods for treating autoimmune disease (e.g., juvenile rheumatoid arthritis, lupus, etc.) and for inhibiting inflammation (e.g., associated with autoimmune disease) and cellular chemotaxis (e.g., of neutrophils, NK cells and T cells). The present invention further provides a diagnostic marker (e.g., DEK antigen) for autoimmune disease.

9 Claims, 20 Drawing Sheets

(56) References Cited

OTHER PUBLICATIONS

Kim et al., "Treatment with cyclosporin switching to hydroxycholoroquine in patients with rheumatoid arthritis" Ann Rheum Dis, 60, 2001, pp. 514-517.*
Mor-Vaknin et al., "The nuclear protein DEK, a putative autoantigen in JRA, is secreted by activated human macrophages and exhibits chemokine activity" Arthritis & Rheumatism, 52(9), Sep. 2005, p. S442.*
Mor-Vaknin et al., Cover page to 2005 Annual Scientific Meeting, Arthritis & Rheumatism, 52(9), Sep. 2005.*
Thomas Blom "Comment on 'the influence of the proinflammatory cytokine, osteopontin, on autoimmune demyelinating disease'" Science, 299 (2003), p. 1845.*
Hnatowich et al., "The Preparation and Labeling of DTPA-Coupled Albumin," Int J Appl Radiat Isot, 33, pp. 327 (1982).
Hollenbach et al., "Daxx and histone deacetylase II associate with chromatin through an interaction with core histones and the chromatin-associated protein Dek ," J Cell Sci, 115, pp. 3319-3330 (2002).
Holmes et al., "Structure and functional expression of a human interleukin-8 receptor," Science, 253, pp. 1278-1280 (1991).
Horuk et al., "Expression of chemokine receptors by subsets of neurons in the central nervous system," J Immunol, 158, pp. 2882-2890 (1997).
Houghten et al., "The Use of Synthetic Peptide Combinatorial Libraries for the Identification of Bioactive Peptides," Biotechniques, 13, pp. 412-421 (1992).
Iwabuchi et al., "Use of the two-hybrid system to identify the domain of p53 involved in oligomerization," Oncogene, 8, 1693-1696 (1993).
Izzo et al., "Interleukin-8 and Neutrophil Markers in Colonic Mucosa from Patients with Ulcerative Colitis," Am J Gastroentrol, 87, pp. 1447-1452, (1992).
Jones et al., "In vivo assessment of lung inflammatory cell activity in patients with COPD and asthma," Eur Respir J, 21, pp. 567-573 (2003).
Kappes et al., "Functional Domains of the Ubiquitous Chromatin Protein DEK," Mol Cell Biol, 24, pp. 6000-6010 (2004).
Kappes et al., "Phosphorylation by Protein Kinase CK2 Changes the DNA Binding Properties of the Human Chromatin Protein DEK," Mol Cell Biol, 24, pp. 6011-6020 (2004).
Khaw et al., "Myocardial Infarct Imaging of Antibodies to Canine Cardiac Myosin with Indium-111-Diethylenetriamine Pantaacetic Acid," Science, 209, pp. 295-297 (1980).
Koch et al., "Regulation of angiogenesis by the C-X-C chemokines interleukin-8 and epithelial neutrophil activating peptide 78 in the rheumatoid joint," Arthritis and Rheutmatism, 44, pp. 31-40 (2001).
Koehler et al., "Continuous Cultures of Fused Cells Secreting Antibody of Predefined Specificity," Nature, 256, pp. 495-497 (1975).
Kojima,"GRO-α mRNA is Selectively Overexpressed in Psoriatic Epidermis and is Reduced by Cyclosporin A In Vivo, but not in Cultured Keratinocytes," J Invest Dermatol, 101, pp. 767-772 (1993).
Kondoh et al., "Identification and Characterization of Genes Associated with Human Hepatocellular Carcinogenesis ," Cancer Res, 59, pp. 4990-4996 (1996).
Kroes et al., "The identification of novel therapeutic targets for the treatment of malignant brain tumors," Cancer Lett, 156, pp. 191-198 (2000).
Lam et al., "A new type of synthetic peptide library for identifying ligand-binding activity," Nature, 354, pp. 82-84 (1991).
Lam, "Application of combinatorial library methods in cancer research and drug discovery," Anticancer Drug Des, 12, pp. 145-167 (1997).
Lane et al., "Interleukin-8 Stimulates Human Immunodeficiency Virus Type 1 Replication and Is a Potential New Target for Antiretroviral Therapy," J Virol, 75, pp. 8195-8202 (2001).
Lauffer, "Targeted Relaxation Enhancement Agents for MRI," Methods in Enzymology, Magnetic Resonance in Medicine, 22, pp. 339-342 (1991).
Li et al., "Lentiviral vector delivery of recombinant small interfering RNA expression cassettes.," Methods Enzymol, 392, pp. 218-226 (2005).
Loizou et al., "The Protein Kinase CK2 Facilitates Repair of Chromosomal DNA Single-Strand Breaks," Cell, 117, pp. 17-28 (2004).
Macon et al., "Natural Killer-Like T-cell Lymphomas: Aggressive Lymphomas of T-Large Granular Lymphocytes," Blood, 87, pp. 1474-1483 (1996).
Madura et al., "N-recognin/Ubc2 Interactions in the N-end Rule Pathway," J Biol Chem, 268, pp. 12046-12054 (1993).
Mahida et al., "Enhanced Synthesis of neutrophil-activating peptide-I/interleukin-8 in active ulcerative colitis," Clin Sci, 82, pp. 273 (1992).
Maniatis et al., "An extensive network of coupling among gene expression machines.," Nature, 416, pp. 499-506 (2002).
Martin et al. Remington's Pharmaceutical Sciences, 15th ed., (1975).
Martin et al., "A New Access to 2'-O-Alkylated Ribonucleosides and Properties of 2'-O-Alkylated Oligoribonucleotides,"Helv Chim Acta, 78, pp. 486 (1995).
Matsukawa et al., "Involvement of Growth-Related Protein in Lipopolysaccharide-Induced Rabbit Arthritis: Cooperation between Growth-Related Protein and IL-8, and Interrelated Regulation among TNFα, IL-1, IL-1 Receptor Antagonist, IL-8, and Growth-Related Protein," Lab Invest, 79, pp. 591-600 (1999).
McConnell et al., "The Cytosensor Microphysiometer: Biological Applications of Silicon Technology," Science, 257, pp. 1906-1912 (1992).
McGarvey et al., "The Acute Myeloid Leukemia-associated Protein, DEK, Forms a Splicing-dependent Interaction with Exon-product Complexes," J Cell Biol, 150, pp. 309-320 (2000).
Mehul et al., "Plasma membrane targetting, vesicular budding and release of galectin 3 from the cytoplasm of mammalian cells during secretion," J Cell Sci, 110, pp. 1169-1178 (1997).
Mor-Vaknin et al., "Vimentin is secreted by activated macrophages," Nat Cell Biol, 5, pp. 59-63 (2003).
Murphy et al., "Cloning of complementary DNA encoding a functional human interleukin-8 receptor," Science, 253, pp. 1280-1283 (1991).
Murray et al- "Antibodies to the 45 kDa DEK nuclear antigen in pauciarticular onset juvenile rheumatoid arthritis and iridocyclitis: selective association with MHC gene," J Rheumatol, 24, pp. 560-567 (1997).
Nielsen et al., "Sequence-Selective Recognition of DNA by Strand Displacement with a Thymine-Substituted Polyamide," Science, 254, pp. 1497 (1991).
Paleolog, "Angiogenesis in rheumatoid arthritis," Arthritis Res., 4(Supp 3), pp. s81-s90 (2002).
Peichl et al., "Presence of NAP-1/IL-8 in synovial fluids indicates a possible pathogenic role in rheumatoid arthritis," Scand J Immunol, 34, pp. 333-339 (1991).
Punturieri et al., "Regulation of Elastinolytic Cysteine Proteinase Activity in Normal and Cathepsin K-deficient Human Macrophages," J Exp Med, 192, pp. 789-799 (2000).
Quan et al., "Antibodies against the N-terminus of IL-8 receptor A inhibit neutrophil chemotaxis," Biochem Biophys Res Commun, 219, pp. 405-411 (1996).
Raposo et al., "B lymphocytes secrete antigen-presenting vesicles," J Exp Med, 183, pp. 1161-1172 (1996).
Reddy et al., "Pericellular mobilization of the tissue-destructive cysteine proteinases, cathepsins B, L, and S, by human monocytederived macrophages," Proc Natl Acad Sci USA, 92, pp. 3849-3853 (1995).
Rivas et al., "New Developments in the Study of biomolecular associations via sedimentation equilibrium," Trends Biochem Sci, 18, pp. 284-287 (1993).
Rovaris et al., "MR-based technology for in vivo detection, characterization, and quantification of pathology of relapsing-remitting multiple sclerosis," J Rehabil Res Dev, 39, pp. 243-259 (2002).
Samanta et al., "Identification and Characterization of Specific Receptors for Monocyte-Derived Neutrophil Chemotactic Factor (Mdncf) on Human Neutrophils," J Exp Med, 169, pp. 1185-1189 (1989).

(56) References Cited

OTHER PUBLICATIONS

Sambrook et al. "Molecular Cloning: A Laboratory Manual" 2nd ed., pp. 16.9-16.15 (1989).
Santamaria-Babi et al., "The interleukin-8 receptor B and CXC chemokines can mediate transendothelial migration of human skin homing T cells," Eur J Immunol, 26, pp. 2056-2061 (1996).
Sarno et al., "Selectivity of 4,5,6,7-tetrabromobenzotriazole, an ATP site-directed inhibitor of protein kinase CK2 ('casein kinase-2')," FEBS Lett, 496, pp. 44-48 (2001).
Sarno et al., "Toward the rational design of protein kinase casein kinase-2 inhibitors," Pharmacol Ther, 93, pp. 159-168 (2002).
Adams et al. "DEK binding to class II MHC Y-box sequences is gene- and allele-specific," Arthritis Res Ther, 5, pp. R226-R233 (2003).
Alexiadis et al., "The protein encoded by the proto-oncogene DEK changes the topology of chromatin and reduces the efficiency of DNA replication in a chromatin-specific manner," Genes Dev, 14, pp. 1308-1312 (2000).
Al-Qahtani et al., "Species-specificity in endoplasmic reticulum signal peptide utilization revealed by proteins from *Trypanosoma brucei* and *Leishmania*," Biochem J, 331 (pt 2), pp. 521-529, (1998).
Anderson et al. "Quantitative Filter Hybridization," Nucleic Acid Hybridization: A Practical Approach, Chapter 4, pp. 73-111 (1985).
Ausubel et al., Current Protocols in Molecular Biology, (1999).
Bartel et al., "Elimination of False Positives that Arise in Using the Two-Hybrid System," Biotechniques, 14, pp. 920-924 (1993).
Besemer et al., "Specific binding, internalization, and degradation of human neutrophil activating factor by human polymorphonuclear leukocytes," J Biol Chem, 264, pp. 17409-17415 (1989).
Boisvert et al., "A Leukocyte Homologue of the IL-8 Receptor CCXR-2 Mediates the Accumulation of Macrophages in Atherosclerotic Lesions of LDL Receptor-deficient Mice," J Clin Invest, 101, pp. 353-363 (1998).
Bonaldi et al., "Monocytic cells hyperacetylate chromatin protein HMGB1 to redirect it towards secretion," Embo J, 22, pp. 5551-5560 (2003).
Broberger et al., "Autoantibodies in Human Ulcerative Coltis," J Exp Med, 110, pp. 657-674 (1959).
Bruhn et al., ALY, a context-dependent coactivator of LEF-1 and AML-1 is required for TCRα enhancer function Genes & Dev, 11, pp. 640-653, (1997).
Carrell et al., "A Solution-Phase Screening Procedure for the Isolation of Active Compounds from a Library of Molecules," Angew Chem Int Ed Engl, 33, pp. 2061-2064 (1994).
Carrell et al., "A Novel Procedure for the Synthesis of Libraries Containing Small Organic Molecules," Angew Chem Int Ed Engl, 33, pp. 2059-2061 (1994).
Cassidy et al. Textbook of Pediatric Rheumatology, 4th ed., (2001).
Cho et al., "An Unnatural Biopolymer," Science, 261, pp. 1303-1305 (1993).
Chuntharapai et al., "Monoclonal Antibodies Detect Different Distribution Patterns of IL-8 Receptor A and IL-8 Receptor B on Human Periphal Blood Leukocytes," J Immunol, 153, pp. 5682 (1994).
Chuntharapai et al., "Regulation of the expression of IL-8 receptor A/B by IL-8: possible functions of each receptor," J Immunol, 155, pp. 2587-2594 (1995).
Cleary et al., "p300/CBP-associated Factor Drives DEK into Interchromatin Granule Clusters," J Biol Chem, 280, pp. 31760-31767 (2005).
Cull et al., "Screening for receptor ligands using large libraries of peptides linked to the C terminus of the lac repressor," Proc Natl Acad Sci USA, 89, pp. 1865-1869 (1992).
Cummings, "Expression and Function of the Chemokine Receptors CXCR1 and CXCR2 in Sepsis," J Immunol, 162, pp. 2341-2346 (1999).
Cwirla et al, "Peptides on phage: A vast library of peptides for identifying ligands," Proc Natl Acad Sci USA, 87, 6378-6382 (1990).
Daibata et al., "Differential Gene-Expression Profiling in the Leukemia Cell Lines Derived From Indolent and Aggressive Phases of Cd56+ T-Cell Large Granular Lymphocyte Leukemia," Int J Cancer, 108, pp. 854-851 (2004).
Devlin et al., " Random Peptide Libraries: A Source of Specific Protein Binding Molecules," Science, 249, pp. 404-406 (1990).
DeWitt et al., ""Diversomers": An approach to nonpeptide, nonoligomeric chemical diversity," Proc Natl Acad Sci USA, 90, pp. 6909-6913 (1993).
Dong et al., "Autoantibodies to Dek Oncoprotein in Human Inflammatory Disease," Arthritis Rheum, 43, pp. 85-93 (2000).
Dong et al., "Autoantibodies to DEK oncoprotein in a patient with systemic lupus erythematosus and sarcoidosis," Arthritis Rheum, 41, pp. 1505-1510 (1998).
Endo et al., "Elevation of Interleukin-8 (IL-8) Levels in Joint Fluids of Patients with Rheumatoid Arthritis and the Induction by IL-8 of Leukocyte Infiltration and Synovitis in Rabbit Joints," Lymphokine Cytokine Res, 10, pp. 245-252 (1991).
Erb et al., "Recursive Deconvolution of Combinatorial Chemical Libraries," Proc Natl Acad Sci USA, 91, pp. 11422-11426 (1994).
Escola et al., "Selective Enrichment of Tetraspan Proteins on the Internal Vesicles of Multivesicular Endosomes and on Exosomes Secreted by Human B-lymphocytes," J Biol Chem, 273, pp. 20121-20127 (1998).
Evans et al., "Defining a 0.5-Mb Region of Genomic Gain on Chromosome 6p22 in Bladder Cancer by Quantitative-Multiplex Polymerase Chain Reaction," Am J Pathol, 164, pp. 285-293 (2004).
Faulkner et al., "Protein Phosphatase 2A Activates the HIV-2 Promoter through Enhancer Elements That Include the pets Site," J Biol Chem, 276, pp. 25804-25812 (2001).
Felici et al., "Selection of Antibody Ligands from a Large Library of Oligopeptides Expressed on a Multivalent Exposition Vector," J Mol Biol, 222, pp. 301-310 (1991).
Fevrier et al., "Cells release prions in association with exosomes," Proc Natl Acad Sci USA, 101, 9683-9688 (2004).
Fodor et al., "Multiplexed biochemical assays with biological chips," Nature, 364, pp. 555-556 (1993).
Fornerod et al., "Relocation of the carboxyterminal part of CAN from the nuclear envelope to the nucleus as a result of leukemia-specific chromosome rearrangements," Oncogene, 10, pp. 1739-1748 (1995).
Fu et al., "DEK, an autoantigen involved in a chromosomal translocation in acute myelogenous leukemia, binds to the HIV-2 enhancer," Proc Natl Acad Sci USA, 94, pp. 1811-1815 (1997).
Fu et al., "Purification of the pets Factor: A Nuclear Protein That Binds to the Inducible Tg-Rich Element of the Human Immunodeficiency Virus Type 2 Enhancer," J Biol Chem, 271, pp. 19599-19605 (1996).
Gallop et al., "Applications of Combinatorial Technologies to Drug Discovery. 1. Background and Peptide Combinatorial Libraries," J Med Chem, 37, pp. 1233-1251 (1994).
Gardella et al., "The nuclear protein HMGB1 is secreted by monocytes via a non-classical, vesicle-mediated secretory pathway," EMBO Rep, 3, pp. 995-1001 (2002).
Gatfield et al., "REF1/Aly and the additional exon junction complex proteins are dispensible for nuclear mRNA export," J Cell Biol, 159, pp. 579-588 (2002).
Ghose et al., "Preparation of Antibody-Linked Cytotoxic Agents," Methods Enzymol, 93, pp. 280-333 (1983).
Gillitzer et al., "Differential Expression of GRO-α and IL-8 mRNa in Psoriasis: A Model for Neutrophil Migration and Accumulation In Vivo," J Invest Dermatol, 107, pp. 778 (1996).
Griffin et al., "Initial Clinical Study of Indium-111-Labedl Clone 110 Anticarcinoembryonic Antigen Antibody in Patients with Colorectal Cancer," J Clinc Onc, 9, pp. 631-640 (1991).
Grob et al., "Characterization of a Receptor for Human Monocyte-derived Neutrophil Chemotactic Factor/Interleukin-8," J Biol Chem, 265, pp. 8311 (1990).
Grottke et al., "Identification of Differentially Expressed Genes in Human Melanoma Cells With Acquired Resistance to Various Antineoplastic Drugs," Int J Cancer, 88, pp. 535-546 (2000).
Haber et al., "Antinuclear Antibody in Juvenile Rheumatoid Arthritis Sera Reacts with 50-40 kDa Antigen(s) Found in HeLa Nuclear Extracts," J Rheumatol, 16, pp. 949-954 (1989).
Hage et al., "Recent advances in chromatographic and electrophoretic methods for the study of drug-protein interactions," J Chromatogr Biomed Sci Appl, 699, pp. 499-525 (1997).

(56) References Cited

OTHER PUBLICATIONS

Hammond et al., "IL-8 Induces Neutrophil Chemotaxis Predominatly Via Type I IL-8 Receptors," J Immunol, 155, pp. 1428-1433 (1995).
Hayashida et al., "Synovial stromal cells from rheumatoid arthritis patients attract monocytes by producing MCP-1 and IL-8," Arthritis Res, 3, pp. 1816-1826 (2001).
Heegaard, "Capillary electrophoresis for the study of affinity interactions," J Mol Recognit, 11, pp. 141-148 (1998).
Sarno et al., "Unique Activation Mechanism of Protein Kinase CK2:The N-Terminal Segment Is Essential for Constitutive Activity of the Catalytic Subunit But Not of the Holoenzyme," J Biol Chem, 277, pp. 22509-22514 (2002).
Scheinberg et al., "Tumor Imaging with Radioactive Metal Chelates Conjugated to Monoclonal Antibodies," Science, 215, pp. 1511-1513 (1982).
Schwartz et al., "Role of the GRO Family of Chemokines in Monocyte Adhesion to MM-LDL-Stimulated Endothelium," J Clin Invest, 94, pp. 1968 (1994).
Scott et al., "Searching for Peptide Ligands with an Epitope Library," Science, 249, pp. 386-390 (1990).
Sexton et al., "Immunomagnetic capture of lens membrane fractions containing steroid binding protein," Biochem Biophys Res Commun, 295, pp. 1027-1031 (2002).
Sierakowska et al., "The putative oncoprotein DEK, part of a chimera protein associated with acute myeloid leukaemia, is an autoantigen in juvenile rheumatoid arthritis," Clin Exp Immunol, 94, pp. 435-439 (1993).
Sjolander et al., "Integrated Fluid Handling System for Biomolecular Interaction Analysis," Anal Chem, 63, pp. 2338-2345 (1991).
Smith et al., "GLI-2 Modulates Retroviral Gene Expression," J Virol, 75, pp. 2301-2313 (2001).
Spits et al., "Development of Human T and Natural Killer Cells," Blood, 85, pp. 2654-2670, (1995).
Stewart et al., "Lentivirus-delivered stable gene silencing by RNAi in primary cells," RNA, 9, pp. 493-501 (2003).
Streiter et al., "The Functional Role of the ELR Motif in CXC Chemokine-mediated Angiogenesis," J Biol Chem, 270, pp. 27348-27357 (1995).
Sumerdon et al., "An Optimized Antibody-Chelator Conjugate for Imaging of Carcinoembryonic Antigen with Indium-111," Nucl Med Biol, 17, pp. 247-254 (1990).
Szabo et al., "Surface plasmon resonance and its use in biomolecular interaction analysis (BIA)," Curr Opin Struct Biol, 5, pp. 699-705 (1995).
Szer et al., "A Novel Autoantibody to the Putative Oncoprotein DEK in Pauciarticular Onset Juvenile Rheumatoid Arthritis," J Rheumatol, 21, pp. 2136-2142 (1994).
Szer et al., "Antinuclear Antibody Profile in Juvenile Rheumatoid Arthritis," J Rheumatol, 18, pp. 401-408 (1991).
Takata et al., "Cutting edge: expression of chemokine receptor CXCR1 on human effector CD8+ T cells," J Immunol, 173, pp. 2231-2235 (2004).
Tani et al., "Interferon-gamma maintains the binding and functional capacity of receptors for IL-8 on cultured human T cells," Eur J Immunol, 28, pp. 502-507 (1998).
Terkeltaub et al. "The murine homolog of the interleukin-8 receptor CXCR-2 is essential for the occurrence of neutrophilic inflammation in the air pouch model of acute urate crystal-induced gouty synovitis,", Arthritis Rheum, 41, pp. 900-909 (1998).
Terkeltaub et al., "Chemokines and atherosclerosis," Curr Opin Lipidol, 9, pp. 397-405(1998).
Thery et al., "Proteomic Analysis of Dendritic Cell-Derived Exosomes: A Secreted Subcellular Compartment Distinct from Apoptotic Vesicles," J Immunol, 166, pp. 7308-7318 (2001).
Thorpe et al., "Improved Antitumor Effects of Immunotoxins Prepared with Deglycosylated Ricin A-Chain and Hindered Bisulfide Linkages," Cancer Res, 48, pp. 6396-6403 (1988).
Troughton et al., "Synovial Fluid Interleukin-8 and Neutrophil Function in Rheumatoid Arthritis and Seronegative Polyarthritis," Br J Rheumatol, 35, pp. 1244-1251 (1996).
Verbaugh et al., "Interleukin-8 (IL-8) in synovial fluid of rheumatoid and nonrheumatoid joint effusions," Clin Rheumatol, 12, pp. 494-499 (1993).
Von Lindern et al., "Characterization of the translocation breakpoint sequences of two DEK-CAN fusion genes present in t(6;9) acute myeloid leukemia and a SET-CAN fusion gene found in a case of acute undifferentiated leukemia," Genes Chrom Cancer, 5, pp. 227-234 (1992).
Von Lindern et al., "The Translocation (6;9), Associated with a Specific Subtypeof Acute Myeloid Leukemia, Results in the Fusion of Two Genes, dek and can, and the Expression of a Chimeric, Leukemia-Specific dek-can mRNA," Mol Cell Biol, 12, pp. 1687-1697 (1992).
Von Lindern et al., "Translocation t(6;9) in acute non-lymphocytic leukaemia results in the formation of a DEK-CAN fusion gene," Baillieres Clin Haematol, 5, pp. 857-879 (1992).
Waldmann et al., "The DEK protein—an abundant and ubiquitous constituent of mammalian chromatin," Gene, 343, pp. 1-9 (2004).
Waldmann et al., "The Ubiquitous Chromatin Protein DEK Alters the Structure of DNA by Introducing Positive Supercoils," J Biol Chem, 277, pp. 24988-24994 (2002).
Wang et al., "Chemokines and their role in tumor growth and metastasis," J Immunol Methods, 220, pp. 1-17 (1998).
Wang et al., "HMG-1 as a Late Mediator of Endotoxin Lethality in Mice," Science, 285, pp. 248-251 (1999).
White et al., "Identification of a Potent, Selective Non-peptide CXCR2 Antagonist That Inhibits Interleukin-8-induced Neutrophil Migration," J Biol Chem, 273, pp. 10095-10098 (1998).
Wong et al., "A Rapid Chemical Method of Labeling Human Plasma Proteins with 99mTc-Pertechnetate at pH 7.4," Int J Appl Radiat Isot, 29, pp. 251-253 (1978).
Wong et al., "Imaging Endocarditis with Tc-99m-Labeled Antibody—An Experimental Study: Concise Communication," J Nucl Med, 23, pp. 229-234 (1982).
Xia et al., "Chemokines/chemokine receptors in the central nervous system and Alzheimer's disease," J Neurovirol, 5, pp. 32-41 (1999).
Xia et al., "Interleukin-8 Receptor B Immunoreactivity in Brain and Neuritic Plaques of Alzheimer's Disease," Am J Pathol, 150, pp. 1267-1274 (1997).
Xu et al., "Modulation of IL-8 receptor expression on purified human T lymphocytes is associated with changed chemotactic responses to IL-8," J Leukocyte Biol, 57, pp. 335-342 (1995).
Zervos et al., "Mxi1, a Protein that Specifically Interacts with Max to Bind Myc-Max Recognition Sites," Cell, 72, pp. 223-232 (1993).
Zuckermann et al., "Discovery of Nanomolar Ligands for 7-Transmembrane G-Protein-Coupled Receptors from a Diverse N-(Substituted)glycine Peptoid Library," J Med Chem, 37, pp. 2678-2685 (1994).
Stinchcombe et al., "Regulated Secretion from Hemopoietic Cells," J Cell Biol, 147, pp. 1-5 (1999).

* cited by examiner

A

B

C

DEK PROTEIN COMPOSITIONS AND METHODS OF USING THE SAME

The present application is a national phase application under 35 U.S.C. §371 of PCT International Application No. PCT/US2006/041010, filed on Oct. 16, 2006, which claims priority to U.S. Provisional Patent Application Ser. No. 60/726,674 filed Oct. 14, 2005, each of which are herein incorporated by reference in their entirety.

This invention was made with government support under AI036658, AR056748 and AR055620 awarded by the National Institutes of Health. The government has certain rights in the invention.

FIELD OF THE INVENTION

The present invention relates to DEK protein compositions (e.g., antibodies, small molecule inhibitors, siRNAs) and methods of using the same. In particular, the present invention provides compositions and methods for treating autoimmune disease (e.g., juvenile rheumatoid arthritis, lupus, etc.) and for inhibiting inflammation (e.g., associated with autoimmune disease) and cellular chemotaxis (e.g., of neutrophils, NK cells and T cells). The present invention further provides a diagnostic marker (e.g., DEK antigen) for autoimmune disease.

BACKGROUND OF THE INVENTION

Autoimmune diseases are generally understood to be diseases where the target of the disease is "self" or "self antigen." Among the many types of autoimmune diseases, there are a number of diseases that are believed to involve T cell immunity directed to self antigens, including, for example, multiple sclerosis (MS), Type I diabetes, and rheumatoid arthritis (RA).

Juvenile rheumatoid arthritis/juvenile idiopathic arthritis (JRA/JIA) is the most common rheumatic disease in children and the most common cause of childhood disability (See, e.g., Cassidy and Petty, Textbook of Pediatric Rheumatology, 4$^{th}$ Edition, Philadelphia: W.B. Saunders Co., (2001)). JRA/JIA is considered to be an autoimmune disease, although it pathogenesis is not well understood (e.g., an inciting antigen(s) has not been identified).

When a patient is diagnosed with an autoimmune disease such as JRA, the choice of appropriate therapeutic interventions would be considerably facilitated by diagnostic and prognostic indicators that accurately reflect the current severity of the disease, predict future severity, and monitor response to therapy. Thus, there is a need in the art for reliable diagnostic and prognostic methods to monitor disease activity and response to therapy in patients suffering from autoimmune and chronic inflammatory diseases. Additionally, new treatments (e.g., therapeutic compositions and methods) are needed for inflammatory and autoimmune diseases (e.g., JRA).

SUMMARY OF THE INVENTION

The present invention relates to DEK protein compositions (e.g., antibodies, small molecule inhibitors, siRNAs) and methods of using the same. In particular, the present invention provides compositions and methods for treating autoimmune disease (e.g., juvenile rheumatoid arthritis, lupus, etc.) and for inhibiting inflammation (e.g., associated with autoimmune disease) and cellular chemotaxis (e.g., of neutrophils, NK cells and T cells). The present invention further provides a diagnostic marker (e.g., DEK antigen) for autoimmune disease.

Accordingly, the present invention provides a method of treating a subject with an autoimmune or chronic inflammatory disease (e.g., JRA) comprising altering DEK expression and/or activity in the cells. In some embodiments, altering DEK expression and/or activity comprises providing to the cells DEK specific siRNAs. In some embodiments, the siRNAs reduce expression of DEK in macrophages of the subject. In some embodiments, the macrophages are involved in recruiting cells to a site (e.g., of inflammation) within the subject. In some embodiments, the cells are selected from the group comprising neutrophils, CD8$^+$ T cells, and NK cells. In some embodiments, altering DEK expression and/or activity comprises providing to the subject an antibody specific for DEK. In some embodiments, the antibody reduces activity and/or function of DEK. In some embodiments, the antibody inhibits chemotaxis of neutrophils, CD8$^+$ T cells, and/or NK cells. In some embodiments, the method of treating reduces the amount of DEK released into the extracellular matrix of the macrophage cells. In some embodiments, the method of treating reduces DEK interaction with one or more other proteins (e.g., ALY). In some embodiments, reduced levels of interaction between DEK and ALY protein alters chromatin structure (e.g., leads to DNA supercoiling). In some embodiments, altering DEK expression and/or activity in the subject (e.g., in macrophages within the subject) sensitizes the subject to therapeutic treatment (e.g., with an anti-inflammatory agent). In some embodiments, sensitizing the subject to therapeutic treatment reduces signs, symptoms and pathologies associated with autoimmune disease (e.g., JRA). In some embodiments, treating comprises administration of an anti-inflammatory agent and/or an immunosuppressive agent to the subject.

The present invention also provides a method of treating a subject with autoimmune disease comprising: providing a composition comprising an inhibitor of DEK; and administering the composition to the subject under conditions such that DEK expression and/or activity is reduced in the subject. In some embodiments, treating inhibits signs, symptoms and pathologies associated with autoimmune disease. In some embodiments, treating inhibits chemotaxis of neutrophils, CD8$^+$ T cells, and/or NK cells in the subject. In some embodiments, the inhibition of chemotaxis of neutrophils, CD8$^+$ T cells, and/or NK cells prevents these cells from being recruited by DEK (e.g., into a site of inflammation). In some embodiments, the inhibitor of DEK is a DEK specific siRNA. In some embodiments, the inhibitor of DEK is an antibody specific for DEK. In some embodiments, the composition comprising an inhibitor of DEK is co-administered with a composition comprising an anti-inflammatory or immunosuppressive agent (e.g., cyclosporing or dexamethasone). In some embodiments, the method of treating reduces the amount of DEK released into the extracellular matrix of cells expressing DEK within the subject (e.g., macrophages).

The present invention also provides a composition comprising a pharmaceutically effective amount of an agent that inhibits DEK expression and/or activity, wherein the pharmaceutically effective amount is sufficient to inhibit DEK mediated chemotaxis (e.g., of neutrophils, CD8$^+$ T cells, and NK cells) in a subject.

The present invention also provides a method for detecting (e.g., diagnosing) autoimmune or chronic inflammatory disease, comprising: providing a sample from a subject suspected of having an autoimmune disease; and detecting the presence or absence of DEK in the sample. In some embodiments, the presence of DEK in the sample is indicative of active autoimmune disease in the subject. In some embodiments, the autoimmune or chronic inflammatory disease is selected from the group comprising, but not limited to, rheumatoid arthritis (RA), juvenile rheumatoid arthritis (JRA), juvenile idiopathic arthritis (JIA), atherosclerosis, congestive heart failure, and Crohn's disease. In some embodiments, the sample is selected from the group consisting of serum, plasma, blood, and urine.

The present invention also provides a kit for characterizing autoimmune or chronic inflammatory disease in a subject, comprising: a reagent that specifically detects (e.g. a reagent or reagents sufficient to detect) the presence or absence of expression of DEK; and/or instructions for using the kit for characterizing autoimmune or chronic inflammatory disease in the subject. In some embodiments, the reagent comprises an antibody that specifically binds to DEK (e.g., the antibody specifically binds to DEK protein with low background binding). In yet other embodiments, the antibody binds to human and mouse DEK. In some embodiments, the antibody is a monoclonal antibody. In some embodiments, the kit further comprises instructions. In some embodiments, the instructions comprise instructions required by the United States Food and Drug Administration for use in in vitro diagnostic products.

The present invention additionally provides a method for characterizing a sample (e.g., a blood, plasma or tissue sample) in a subject, comprising providing a sample from a subject (e.g., wherein the sample is blood, plasma or a tissue sample); and detecting the presence or absence of DEK in the sample, thereby characterizing the sample. In some embodiments, the tissue is biopsy tissue. In some embodiments, detecting DEK comprises detecting the presence of DEK mRNA. In some embodiments, detecting the presence of DEK mRNA comprises exposing the DEK mRNA to a nucleic acid probe complementary to at least a portion of the DEK mRNA. In some embodiments, detecting the presence of DEK mRNA comprises a detection assay selected from the group consisting of a Northern blot, in situ hybridization, reverse-transcriptase polymerase chain reaction, and microarray analysis.

In other embodiments, detecting the presence of DEK comprises detecting the presence of a DEK polypeptide. In some embodiments, detecting the presence of a DEK polypeptide comprises exposing the DEK polypeptide to an antibody that specifically binds to DEK and detecting the binding of the antibody to the DEK polypeptide. In some embodiments, the antibody is a monoclonal antibody. In some embodiments, the sample is a post-surgical tissue.

The present invention also provides a method of screening compounds, comprising providing a cell sample; and one or more test compounds; and contacting the cell sample with the test compound; and detecting a change in DEK expression in the cell sample in the presence of the test compound relative to the absence of the test compound. In some embodiments, the cell sample is a monocyte derived macrophage. In some embodiments, detecting comprises detecting DEK mRNA. In other embodiments, detecting comprises detecting a DEK polypeptide. In some embodiments, the cell is in vitro. In other embodiments, the cell is in vivo. In some embodiments, the test compound comprises an antisense compound. In some embodiments, the test compound is a small molecule. In other embodiments, the test compound comprises a drug. In some embodiments, the drug is an antibody. In other embodiments, the drug specifically binds to DEK.

The present invention provides the use of DEK as a marker to identify autoimmune or chronic inflammatory disease in a subject. The present invention additionally provides the use of an antibody (e.g., monoclonal anti-DEK antibody) that specifically binds to DEK that can be used in diagnostic assays (e.g., ELISA assays) of the invention.

DEFINITIONS

Figure 1:
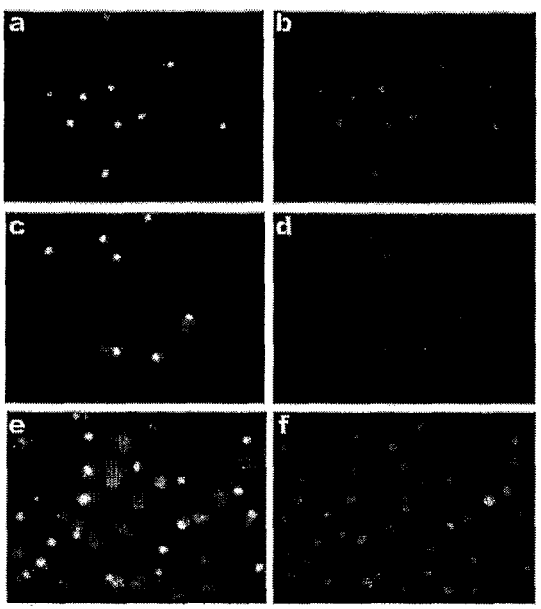
FIG. 1 shows intracellular DEK is not an exclusively nuclear protein. (A) Day 3 MDM (panel a), day 5 MDM (panel c), or day 12 MDM (panel e) incubated with DEK polyclonal antiserum and stained with FITC-conjugated goat anti-rabbit antibody for immunodetection by confocal microscopy. Nuclear staining with DAPI is shown in panels b, d, and f (Magnification 40×). (B) Day 13 human MDM transiently transfected with a plasmid expressing DEK-GFP, and were maintained at 37° C. during image collection by an Olympus IMT-2 inverted light microscope. The distribution of DEK-GFP is shown as nuclear, peri-nuclear, and membranous (panels a, c, and e, respectively). Bright field images of the cells are shown in panels b, d, and f (Magnification 60×).
Figure 1:
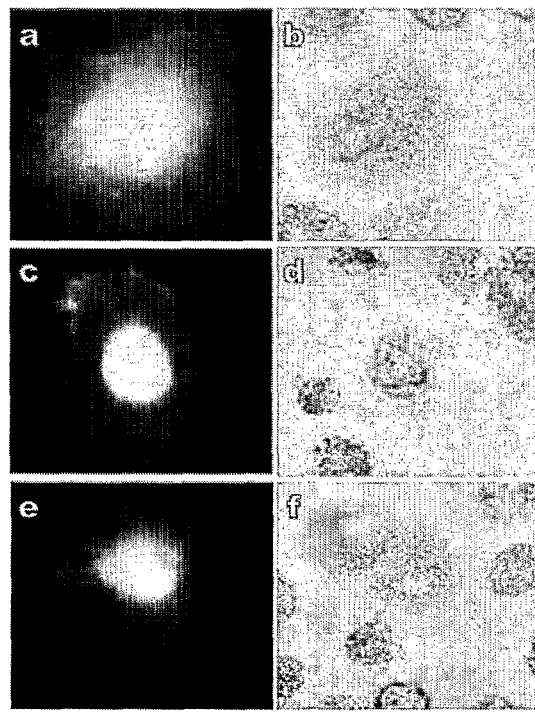

As used herein, the term "autoimmune disease" refers generally to diseases which are characterized as having a component of self-recognition. Examples of autoimmune diseases include, but are not limited to, autoimmune hepatitis, multiple sclerosis (MS), systemic lupus erythematosus (SLE), myasthenia gravis, type I diabetes, rheumatoid arthritis (RA), juvenile rheumatoid arthritis (JRA), juvenile idiopathic arthritis (JIA), psoriasis, Hashimoto's thyroiditis, Grave's disease, ankylosing spondylitis, Sjogrens disease, CREST syndrome, scleroderma and many more. Most autoimmune diseases are also chronic inflammatory diseases. This is defined as a disease process associated with long-term (e.g., greater than 6 months) activation of inflammatory cells (leukocytes). The chronic inflammation leads to damage of patient organs or tissues. Many diseases are chronic inflammatory disorders, but are not know to have an autoimmune basis. For example, atherosclerosis, congestive heart failure, Crohn's disease, ulcerative colitis, polyarteritis nodosa, Whipple's disease, primary sclerosing cholangitis and many more.

The clinical manifestations of these diseases range from mild to severe. For example, mild disease encompasses symptoms that may be function-altering and/or comfort-altering, but are neither immediately organ-threatening nor life-threatening. Severe disease might entail organ-threatening and/or life-threatening symptoms. For example, severe autoimmune disease is often associated with clinical manifestations such as nephritis, vasculitis, central nervous system disease, premature atherosclerosis or lung disease, or combinations thereof, that require aggressive treatment and may be associated with premature death. Anti-phospholipid antibody syndrome is often associated with arterial or venous thrombosis. Any statistically significant correlation that is found to exist between autoimmune or chronic inflammatory disease markers (e.g., DEK) and any clinical parameters of an autoimmune or inflammatory disease enables the use of an autoimmune or chronic inflammatory disease marker (e.g., DEK) assay as part of a diagnostic battery for that disease or group of diseases.

Diseases can exhibit ranges of activities. As used herein, disease activity (e.g., "active juvenile rheumatoid arthritis") refers to whether the pathological manifestations of the disease are fulminant, quiescent, or in a state between these two extremes. For example, a patient suffering from SLE having active disease could be diagnosed or monitored through detecting expression and/or activity of an autoimmune or chronic inflammatory disease marker (e.g., DEK) described in the present invention, whereas a patient having inactive disease may manifest comparatively lower or normal levels of autoimmune or chronic inflammatory disease marker (e.g., DEK) expression and/or activity.

As used herein, the term "chemotaxis" refers to the movement of cells in response to a stimulus (e.g., chemokines). Multiple types of cells have been documented to migrate (e.g., via chemotaxis) into sites (e.g., of inflammation and/or injury) including, but not limited to, neutrophils, $CD8^+$ T cells and natural killer cells.

As used herein, the term "leukotaxis" refers to the chemotaxis of leukocytes. In particular, the term refers to the tendency of leukocytes to accumulate in regions of injury and inflammation.

The term "epitope" as used herein refers to that portion of an antigen that makes contact with a particular antibody.

When a protein or fragment of a protein is used to immunize a host animal, numerous regions of the protein may induce the production of antibodies that bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather than a particular structure such as an epitope).

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject, unless indicated otherwise.

As used herein, the term "subject suspected of having autoimmune or chronic inflammatory disease" refers to a subject that presents one or more symptoms indicative of an autoimmune or chronic inflammatory disease (e.g., hives or joint pain) or is being screened for an autoimmune or chronic inflammatory disease (e.g., during a routine physical). A subject suspected of having an autoimmune or chronic inflammatory disease may also have one or more risk factors. A subject suspected of having an autoimmune or chronic inflammatory disease has generally not been tested for autoimmune or chronic inflammatory disease. However, a "subject suspected of having autoimmune or chronic inflammatory disease" encompasses an individual who has received an initial diagnosis but for whom the severity of the autoimmune or chronic inflammatory disease is not known. The term further includes people who once had autoimmune or chronic inflammatory disease but whose symptoms have ameliorated.

As used herein, the term "subject at risk for autoimmune or chronic inflammatory disease" refers to a subject with one or more risk factors for developing an autoimmune or chronic inflammatory disease. Risk factors include, but are not limited to, gender, age, genetic predisposition, environmental exposure, previous incidents of autoimmune or chronic inflammatory disease, preexisting non-autoimmune or chronic inflammatory diseases, and lifestyle.

As used herein, the term "characterizing autoimmune or chronic inflammatory disease in subject" refers to the identification of one or more properties of a sample in a subject, including but not limited to, the presence of calcified tissue and the subject's prognosis. Autoimmune or chronic inflammatory disease may be characterized by the identification of the expression of one or more autoimmune or chronic inflammatory disease marker genes, including but not limited to, the autoimmune or chronic inflammatory disease markers disclosed herein.

As used herein, the term "autoimmune or chronic inflammatory disease marker genes" refers to a gene whose expression level, or other characteristic, alone or in combination with other genes, is correlated with autoimmune or chronic inflammatory disease or prognosis of autoimmune or chronic inflammatory disease. The correlation may relate to either an increased or decreased expression of the gene. For example, the expression (e.g., as compared to normal, healthy controls) of the gene may be indicative of autoimmune or chronic inflammatory disease, and may be correlated with poor prognosis in an autoimmune or chronic inflammatory disease patient. Autoimmune or chronic inflammatory disease marker expression status may be characterized using any suitable method, including but not limited to, those described in illustrative Examples 1-7 below.

As used herein, the terms "subject suspected of having juvenile rheumatoid arthritis" or "subject suspected of having juvenile arthritis" refer to a subject that presents one or more symptoms indicative of juvenile rheumatoid arthritis (e.g., joint pain) or is being screened for juvenile rheumatoid arthritis (e.g., during a routine physical). A subject suspected of having juvenile rheumatoid arthritis may also have one or more risk factors. A subject suspected of having juvenile rheumatoid arthritis has generally not been tested for juvenile rheumatoid arthritis. However, a "subject suspected of having juvenile rheumatoid arthritis" encompasses an individual who has received an initial diagnosis but for whom the severity of the juvenile rheumatoid arthritis is not known. The term further includes patients who once had juvenile rheumatoid arthritis but whose symptoms have ameliorated.

As used herein, the terms "subject at risk for juvenile rheumatoid arthritis" or "subject at risk for juvenile arthritis" refer to a subject with one or more risk factors for developing juvenile rheumatoid arthritis. Risk factors include, but are not limited to, gender, age, genetic predisposition, environmental exposure, previous incidents of juvenile rheumatoid arthritis, preexisting non-autoimmune or chronic inflammatory diseases, and lifestyle.

As used herein, the terms "characterizing juvenile rheumatoid arthritis in said subject" or "characterizing juvenile arthritis in said subject" refer to the identification of one or more properties of a sample in a subject including, but not limited to, the presence of calcified tissue and the subject's prognosis. Juvenile rheumatoid arthritis may be characterized by the identification of the expression of one or more juvenile rheumatoid arthritis marker genes, including but not limited to, the autoimmune or chronic inflammatory disease markers disclosed herein. Thus, as used herein, the term "detecting autoimmune or chronic inflammatory disease" refers the detection of the presence or absence (e.g., for diagnostic purposes) of a biomarker (e.g., DEK) associated with autoimmune and/or inflammatory disease of the present invention.

As used herein, the term "a reagent that specifically detects expression levels" refers to reagents used to detect the expression of one or more genes (e.g., including but not limited to, the autoimmune and chronic inflammatory disease markers of the present invention). Examples of suitable reagents include but are not limited to, nucleic acid probes capable of specifically hybridizing to the gene of interest, PCR primers capable of specifically amplifying the gene of interest, and antibodies capable of specifically binding to proteins expressed by the gene of interest. Other non-limiting examples can be found in the description and examples below.

As used herein, the term "detecting a decreased or increased expression relative to non-autoimmune or chronic inflammatory disease control" refers to measuring the level of expression of a gene (e.g., the level of mRNA or protein) relative to the level in a non-autoimmune or chronic inflammatory disease (e.g., juvenile rheumatoid arthritis) control sample. Gene expression can be measured using any suitable method, including but not limited to, those described herein.

As used herein, the term "detecting a change in gene expression (e.g., of DEK) in said autoimmune or chronic inflammatory disease sample in the presence of said test compound relative to the absence of said test compound" refers to measuring an altered level of expression (e.g., increased or decreased) in the presence of a test compound relative to the absence of the test compound. Gene expression can be measured using any suitable method, including but not limited to, those described in Examples 1-7 below.

As used herein, the term "instructions for using said kit for detecting autoimmune or chronic inflammatory disease in said subject" includes instructions for using the reagents contained in the kit for the detection and characterization of autoimmune or chronic inflammatory disease in a sample from a subject. In some embodiments, the instructions further comprise the statement of intended use required by the U.S. Food and Drug Administration (FDA) in labeling in vitro diagnostic products.

As used herein, the term "autoimmune or chronic inflammatory disease expression profile map" refers to a presentation of expression levels of genes in a particular type of autoimmune or chronic inflammatory disease. The map may be presented as a graphical representation (e.g., on paper or on a computer screen), a physical representation (e.g., a gel or array) or a digital representation stored in computer memory. In preferred embodiments, maps are generated from pooled samples comprising samples from a plurality of patients with the same type of autoimmune or chronic inflammatory disease.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the terms "processor" and "central processing unit" or "CPU" are used interchangeably and refer to a device that is able to read a program from a computer memory (e.g., ROM or other computer memory) and perform a set of steps according to the program.

As used herein, the term "providing a prognosis" refers to providing information regarding the impact of the presence of autoimmune or chronic inflammatory disease (e.g., as determined by the diagnostic methods of the present invention) on a subject's future health (e.g., expected morbidity or mortality).

As used herein, the term "subject diagnosed with an autoimmune or chronic inflammatory disease" refers to a subject who has been tested and found to have autoimmune or chronic inflammatory disease. The autoimmune or chronic inflammatory disease may be diagnosed using any suitable method, including but not limited to, biopsy, x-ray, blood test, and the diagnostic methods of the present invention.

As used herein, the term "initial diagnosis" refers to results of initial autoimmune or chronic inflammatory disease diagnosis (e.g. the presence or absence of autoimmune or chronic inflammatory disease). An initial diagnosis does not include information about the severity of the autoimmune or chronic inflammatory disease.

As used herein, the term "non-human animals" refers to all non-human animals including, but not limited to, vertebrates such as rodents, non-human primates, ovines, bovines, ruminants, lagomorphs, porcines, caprines, equines, canines, felines, aves, etc.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences."Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics, e.g., hypomethylation) when compared to the wild-type gene or gene product. It is noted that naturally occurring mutants can be isolated; these are identified by the fact that they have altered characteristics (including altered nucleic acid sequences) when compared to the wild-type gene or gene product.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41$ (% G+C), when a nucleic acid is in aqueous solution at 1 M NaCl (See e.g., Anderson and Young, Quantitative Filter Hybridization, in Nucleic Acid Hybridization (1985)). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under 'medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.1% SDS, 5×Denhardt's reagent (50×Denhardt's contains per 500 ml: 5 g Ficoll (Type 400, Pharmacia), 5 g BSA (Fraction V; Sigma)) and 100 µg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to at least a portion of another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "transgene" as used herein refers to a foreign gene that is placed into an organism by, for example, introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally occurring gene.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher (or greater) than that observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk$^-$ cell lines, the CAD gene that is used in conjunction with CAD-deficient cells and the mammalian hypoxanthine-guanine phosphoribosyl transferase (hprt) gene that is used in conjunction with hprt$^-$ cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp. 16.9-16.15.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., autoimmune and chronic inflammatory disease). Test compounds comprise both known and potential therapeutic compounds. A test compound can be determined to be therapeutic by screening using the screening methods of the present invention. In some embodiments of the present invention, test compounds include antisense compounds.

As used herein, the term "sample" is used in its broadest sense. In one sense, it is meant to include a specimen or culture obtained from any source, as well as biological and environmental samples. Biological samples may be obtained from animals (including humans) and refers to a biological material or compositions found therein, including, but not limited to, bone marrow, blood, serum, platelet, plasma, interstitial fluid, urine, cerebrospinal fluid, nucleic acid, DNA, tissue, and purified or filtered forms thereof. Environmental samples include environmental material such as surface matter, soil, water, crystals and industrial samples. Such examples are not however to be construed as limiting the sample types applicable to the present invention.

As used herein, the term "immunoglobulin" or "antibody" refer to proteins that bind a specific antigen. Immunoglobulins include, but are not limited to, polyclonal, monoclonal, chimeric, and humanized antibodies, Fab fragments, F(ab')$_2$ fragments, and includes immunoglobulins of the following classes: IgG, IgA, IgM, IgD, IbE, and secreted immunoglobulins (sIg). Immunoglobulins generally comprise two identical heavy chains and two light chains. However, the terms "antibody" and "immunoglobulin" also encompass single chain antibodies and two chain antibodies.

As used herein, the term "antigen binding protein" refers to proteins that bind to a specific antigen. "Antigen binding proteins" include, but are not limited to, immunoglobulins, including polyclonal, monoclonal, chimeric, and humanized antibodies; Fab fragments, F(ab')$_2$ fragments, and Fab expression libraries; and single chain antibodies.

The term "epitope" as used herein refers to that portion of an antigen that makes contact with a particular immunoglobulin.

When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "specifically binding to DEK with low background binding" refers to an antibody that binds specifically to DEK protein (e.g., in an immunohistochemistry assay) but not to other proteins (e.g., lack of non-specific binding).

As used herein, the term "effective amount" refers to the amount of a composition (e.g., inhibitor of DEK) sufficient to effect beneficial or desired results. An effective amount can be administered in one or more administrations, applications or dosages and is not intended to be limited to a particular formulation or administration route.

As used herein, the term "administration" refers to the act of giving a drug, prodrug, or other agent, or therapeutic treatment (e.g., compositions of the present invention) to a subject (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), oral mucosa (buccal), ear, rectal, by injection (e.g., intravenously, subcutaneously, intratumorally, intraperitoneally, etc.) and the like.

As used herein, the terms "co-administration" and "co-administer" refer to the administration of at least two agent(s) (e.g., DEK siRNAs or antibodies and one or more other agents—e.g., an anti-inflammatory agent) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s).

As used herein, the term "toxic" refers to any detrimental or harmful effects on a subject, a cell, or a tissue as compared to the same cell or tissue prior to the administration of the toxicant.

As used herein, the term "pharmaceutical composition" refers to the combination of an active agent (e.g., DEK siRNAs and/or antibodies) with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "topically" refers to application of the compositions of the present invention to the surface of the skin and mucosal cells and tissues (e.g., alveolar, buccal, lingual, masticatory, or nasal mucosa, and other tissues and cells that line hollow organs or body cavities).

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintigrants (e.g., potato starch or sodium starch glycolate), and the like. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. (1975), incorporated herein by reference).

As used herein, the term "pharmaceutically acceptable salt" refers to any salt (e.g., obtained by reaction with an acid or a base) of a compound of the present invention that is physiologically tolerated in the target subject (e.g., a mammalian subject, and/or in vivo or ex vivo, cells, tissues, or organs). "Salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

The term "siRNAs" refers to short interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "target RNA molecule" refers to an RNA molecule to which at least one strand of the short double-stranded region of an siRNA is homologous or complementary. Typically, when such homology or complementary is about 100%, the siRNA is able to silence or inhibit expression of the target RNA molecule. Although it is believed that processed mRNA is a target of siRNA, the present invention is not limited to any particular hypothesis, and such hypotheses are not necessary to practice the present invention. Thus, it is contemplated that other RNA molecules may also be targets of siRNA. Such targets include unprocessed mRNA, ribosomal RNA, and viral RNA genomes.

DETAILED DESCRIPTION OF THE INVENTION

The present invention relates to DEK protein compositions (e.g., antibodies, small molecule inhibitors, siRNAs) and methods of using the same. In particular, the present invention provides compositions and methods for treating autoimmune disease (e.g., juvenile rheumatoid arthritis, lupus, etc.) and for inhibiting inflammation (e.g., associated with autoimmune disease) and cellular chemotaxis (e.g., of neutrophils, NK cells and T cells). The present invention further provides a diagnostic marker (e.g., DEK antigen) for autoimmune disease.

DEK is a mammalian oncoprotein and putative autoantigen whose primary biologic function has not been previously elucidated, despite literature linking it to the regulation of transcription, altering chromatin architecture, and RNA processing (See, e.g., Adams et al., Arthritis Res Ther 5:R226-33, (2003); Alexiadis et al., Genes Devel 14:1308-12, (2000); Faulkner et al., J Biol Chem 276:25804-12, (2001); Fu et al., Proc Natl Acad Sci USA 94:1811-5, (1997); Fu and Markovitz, J Biol Chem 271:599-605, (1996); Hollenbach et al., Cell Sci 115:3319-30, (2002); McGarvey et al., J Cell Biol 150:309-20, (2000); Waldmann et al., J Biol Chem 277:24988-94, (2002); Waldmann et al., Gene 343:1-9, (2004)). DEK was first characterized as part of the protein product of the dek-can fusion oncogene, resulting from a t(6;9) translocation found in a subset of patients with acute myelogenous leukemia (AML) (See, e.g., von Lindern et al., Mol Cell Biol 12:1687-97, (1992)). The DEK protein is widely conserved among species and is transcribed at high levels, especially in hematopoietically derived cells (See, e.g., Fornerod et al., Oncogene 10, 1739-48, (1995); von Lindern et al., Mol Cell Biol 12:1687-97, (1992); von Lindern et al., Genes Chrom Cancer 5:227-34, (1992); von Lindern et al., Baillieres Clin Haematol 5:857-879, (1992)). DEK is overexpressed in several different malignancies, including melanoma, hepatocellular carcinoma, glioblastoma, bladder cancer, T cell large granular lymphocyte leukemia, and AML independent of the t(6;9) translocation (See, e.g., Daibata et al., Int J Cancer 108:845-51, (2004); Evans et al., Am J Pathol 164:285-93, (2004); Grottke et al., Int Cancer 88:535-46, (2000); Kondoh et al., Cancer Res 59:4990-6, (1999); Kroes et al., Cancer Lett 156:191-198, (2000); Fornerod et al., Oncogene 10, 1739-48, (1995); von Lindern et al., Mol Cell Biol 12:1687-97, (1992); von Lindern et al., Genes Chrom Cancer 5:227-34, (1992); von Lindern et al., Baillieres Clin Haematol 5:857-879, (1992)). Although DEK has previously been described as a strictly nuclear protein, DEK autoreactivity has been identified as a component of the autoantibody profile in patients with juvenile arthritis, and is also seen in patients with other autoimmune diseases (See, e.g., Dong et al., Arthritis Rheum 41:1505-1510, (1998); Dong et al., Arthritis Rheum 43:85, (2000); Haber et al., J Rheumatol 16:949-54, (1989); Murray et al., J Rheum 24:560-567, (1997); Sieralowska et al., Clin Exp Immunol 94:435-39, (1993); Szer et al., J Rheum 21:2136-42, (1994); Szer et al., Rheumatol 18:401-8, (1991)). However, whether DEK contributes directly to immune or autoimmune responses has heretofore remained unknown.

Chemotactic cytokines (chemokines) are a class of potent inflammatory mediators that have the potential to attract specific subsets of leukocytes to sites of inflammation. Chemokines are typically low-molecular-mass (7-9 kd) proteins that can be divided into four subfamilies (CCC or beta-subfamily, CXC or alpha-subfamily, $CX_3C$) and are categorized by their primary amino acid structure. The CXC subfamily is characterized by the two conserved cysteine (C) residues near the N-terminus and separated by an amino acid (X). Some of the CXC chemokines, of which IL-8 and GRO-alpha are representative, belong further to the $ELR^+$ subfamily (Glu-Leu-Arg) and are important in the recruitment and activation of neutrophils via the CXCR1 and CXCR2 receptors.

The interaction of chemokines with specific cell populations is mediated by G-protein-coupled seven-transmembrane receptors (7TMR). Chemokine receptors can be classified into four groups (CR, CCR, CXCR, $CX_3CR$) based upon their primary amino acid sequence. The CXCR1 receptor binds with high affinity to IL-8 and low affinity to NAP-2, ENA-78 (epithelial cell-derived neutrophil-activating factor), GRO-alpha, -beta, and -gamma, whereas, CXCR2 binds with high affinity to all of the mentioned CXC chemokines. Both CXCR1 and CXCR2 receptors are found primarily on neutrophils and a subset of T-cells. (See, e.g., Holmes et al., Science 253:1278 (1991); Murphy et al., Science 253:1280 (1991); Chuntharapai et al., J. Immunol. 153:5682 (1994); Xu et al., J. Leukocyte Biol. 57:335 (1995)).

CXCR1 and CXCR2 have been shown to mediate the responses to CXC chemokines in neutrophils (polymorphonuclear neutrophils; PMN) and are important in the acute inflammatory response. (See, e.g., Grob et al., J. Biol. Chem. 265:8311 (1990); Besemer et al., J. Biol. Chem. 264:17, 409 (1989); Samanta et al., J. Exp. Med. 169:1185 (1989); Holmes et al., Science 253:1280 (1991); Murphy et al., Science 253:1280 (1991)). Although both receptors are involved in neutrophil chemotaxis, in vitro studies using human neutrophils have shown inconclusively if chemotaxis is mediated by one or both receptors. IL-8 induced chemotaxis studies using anti-receptor monoclonal antibodies in CXCR1 and CXCR2 cell lines have led to conflicting reports. (See, e.g., Quan et al., Biochem. Biophys. Res. Commun. 219:405 (1996); Chuntharapai et al., J. Immunol. 155:2587 (1995); Hammond et al., J. Immunol. 155:1428 (1995)). There is also evidence to indicate that the transendothelial migration of $CLA^+$ T-cells is a CXCR2 mediated event. (See, e.g., Santamaria-Babi et al., Eur. J. Immuno. 26:2056 (1996)).

The role, in inflammatory disorders, of neutrophil chemotaxis mediated by the CXCR1 and CXCR2 receptors is generally accepted. It has also been demonstrated that CXCR1 functions as the single dominant CXC chemokine receptor for neutrophil chemotaxis in patients with sepsis. (See, e.g., Cummings, J. Immunol. 162:2341 (1999)).

High levels of IL-8 and tissue neutrophil infiltration have been observed in the synovial tissues of rheumatoid arthritis patients (See, e.g., Endo, Lymphokine Cytokine Res. 10:245 (1991)). Evidence has been presented that GRO-alpha and IL-8 are important mediators involved in the recruitment of neutrophils in the early and late phase of lipopolysaccharide-induced (LPS) rabbit arthritis. (See, e.g., Matsukawa et al., Lab. Invest. 79:591 (1999)). The murine CXCR2 receptor has also shown to be important for neutrophilic inflammation in a mouse model of gouty synovitis. (See, e.g., Terkeltaub et al., Arthritis. Rheum. 41:900 (1998)).

CXC chemokines have attracted attention as being important in the development of atherosclerosis (See, e.g., Terkeltaub et al., Curr. Opin. Lipidol. 9:397 (1998)). The role of CXCR1 and CXCR2 ligands on monocyte function in atherosclerosis in rabbits has been shown (See, e.g., Schwartz et al., J. Clin. Invest. 94:1968 (1994)). Knockout mice that lack CXC2 expression had diminished lesion size (See, e.g., Boisvert et al., J. Clin. Invest. 101:353 (1998)).

The involvement of the CXCR2 receptor in the pathological inflammatory response elicited by central nervous system (CNS) cells as related to Alzheimer's disease is also gaining significant attention (See, e.g., Xia et al., J. Neurovirol. 5:32 (1999)). Reports have focused on the upregulation of CXCR expression on dystrophic neurites of senile plaques (See, e.g., Xia et al., Am. J. Pathol. 150:1267 (1997); R. Horuk et al., J. Immunol. 158:2882 (1997)).

High levels of IL-8 and neutrophil infiltration have been observed in the pathogenesis of a number of other disease indications. These include ulcerative colitis (See, e.g., Mahida, Clin. Sci. 82:273 (1992); Izzo, Am. J. Gastroenterol 87:1447 (1992)) and psoriasis (See, e.g., Gillitzer et al., J. Invest. Dermatol. 107:778 (1996); Kojima, J. Invest. Dermatol 101:767 (1993)). CXCR1 and CXCR2 chemokines and their roles in tumor growth and metastasis have been reviewed (See, e.g., Wang, J. Immunol. Meth. 220:1 (1998)).

T cells and natural killer (NK) cells are distinguished by immunophenotype and molecular genetic studies although there is overlap in T-cell and NK-cell antigen expression, function, and patterns of disease. The ontogeny from naive to effector T-cell is largely obscure. Most T cells express the αβ TCR (T cell receptor) protein and have a helper (CD4+) or suppressor/cytotoxic (CD8+) phenotype. A small population of T cells expresses the γδ TCR and usually has a double negative (CD4−CD8−) phenotype, although some may express CD8 or more rarely, CD4. Normal γδ T cells are preferentially located at extranodal sites such as the splenic red pulp, gastrointestinal tract, and skin.

NK cells arise from a pluripotential stem cell and are related to T-cells, but at some point branch off to form a separate lineage (See, e.g., Spits et al., Blood. 1995; 85:2654-2670). NK cells are distinguished immunologically by the absence of TCR gene rearrangements and TCR protein and lack of surface CD3 (Leu 4) and usually CD5. NK cells and T cells can express CD2, CD7, and in paraffin sections cytoplasmic CD3 (the epsilon chain), CD45RO and CD43. NK cells usually express one or more "NK associated" antigens (CD16, CD56, CD57), but some populations of NK cells do not express these antigens and are identified by functional studies. A subset of cytotoxic T-cells also expresses NK associated antigens and have been called "NK-like" T-cells (See, e.g., Macon et al., Blood. 1996; 87:1474-1483).

The present invention demonstrates that DEK protein is secreted by monocytic cells (e.g., macrophages), accumulates in the joints and blood of subjects with autoimmune disease (e.g., juvenile rheumatoid arthritis), and is secreted in exosomes thereby facilitating its presentation as an autoantigen (See Examples 2-5). The present invention further demonstrates that DEK is a chemotactic factor that attracts neutrophils, CD8+ T cells and natural killer cells through its interactions with CXCR2 and CXCR1 (See Example 7). DEK is released from healthy cells that have not undergone necrosis or apoptosis, and a substantial amount of secreted DEK is found in exosomes. DEK secretion is stimulated by IL-8, and DEK expression is inhibited by immunosuppressants (e.g., cyclosporine and dexamethasone) (See Example 6). Hence, the present invention provides the first secreted nuclear protein, DEK, to be described that acts as a chemotactic factor for inflammatory cells. Thus, the present invention demonstrates that DEK plays a direct role in autoimmune disease and inflammation.

The present invention provides that apoptosis of T cells releases DEK into the cytoplasm (See Example 12). The present invention also provides that secreted DEK can be internalized by cells (See Example 11). The present invention also provides that DEK interacts with proteins involved with transcription (e.g., RNA export from the nucleus (e.g., ALY protein) See Example 13). The present invention also provides that it is possible to silence DEK expression in cells (e.g., using siRNA (e.g., a lentiviral vector encoding shRNA) (See Example 9) and that cells in which DEK expression has been reduced (e.g., via siRNA) display a less compact chromatin structure (See Example 14) and are more sensitive to DNA damage (See Example 15).

Figure 6:
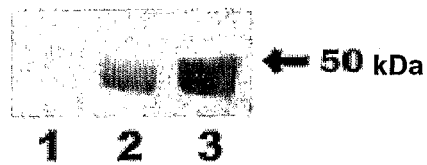
FIG. 6 shows DEK is present in the synovial fluids of patients with juvenile arthritis. (A). Synovial fluids obtained from patients with JRA were analyzed for the presence of DEK by Western blot after fluid was separated from cells by centrifugation. DEK was detected by Western blot using the mouse monoclonal DEK antibody. (B). Day 12 macrophages purified from synovial fluid of a patient with pauciarticular JRA were grown in 10% human serum. Exosomes were purified and analyzed by Western blot using polyclonal DEK antiserum. Lane 1: protein recovered from CD81-coated magnetic beads incubated with 500 μg of concentrated exosome-free supernatant as a negative control. Lane 2: protein recovered from the CD81-coated magnetic beads incubated with 45 μg of protein from the enriched exosomal supernatant fraction obtained by 70,000×g centrifugation. (Lane 2 contains approximately 10-fold less protein than was loaded in Lane 1.) Lane 3: intracellular DEK. (C). The level of DEK protein in normal serum (five individuals and human AB serum) was compared to the level in serum collected from patients with pauciarticular JRA and polyarticular JRA. The levels of DEK found in serum from patients with pauciarticular or polyarticular JRA is significantly higher than those found in serum from normal individuals (*p=0.0401 and **p=0.0002, respectively). The level of DEK protein is measured by ELISA.
Figure 6:
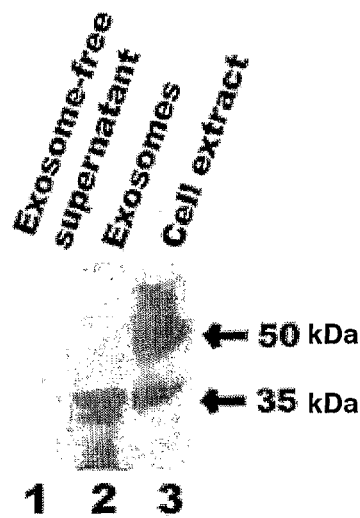
Figure 6:
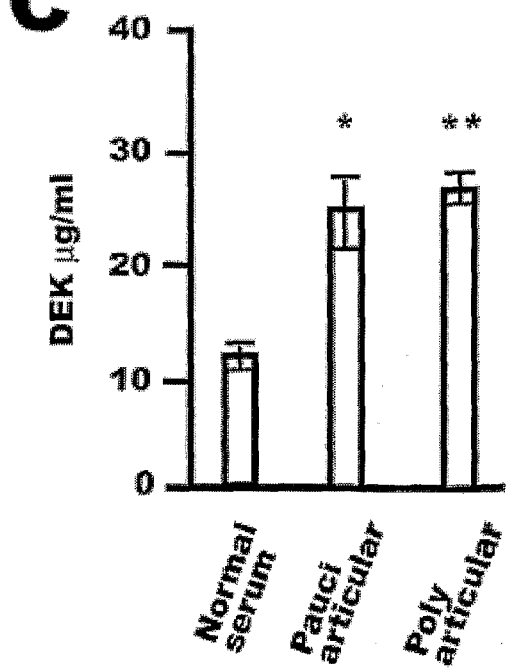

Markers for Autoimmune or Chronic Inflammatory Disease
Identification of Markers The present invention provides markers whose expression is specifically altered in autoimmune or chronic inflammatory disease (e.g., JRA). Specifically, experiments conducted during the development of the present invention resulted in the identification DEK whose expression level was altered (e.g., increased) in autoimmune and/or chronic inflammatory disease (See Example 5, FIG. 6). Such markers find use in the diagnosis and characterization of autoimmune or chronic inflammatory disease.

In some embodiments, the present invention provides a method for detection of expression of autoimmune or chronic inflammatory disease markers (e.g., DEK). In preferred embodiments, expression is measured directly (e.g., at the RNA or protein level). In some embodiments, expression is detected in tissue samples (e.g., biopsy tissue). In other embodiments, expression is detected in bodily fluids (e.g., including but not limited to, plasma, serum, whole blood, mucus, and urine).

For example, using the compositions and methods of the present invention, it was determined that treatment with immunosuppressive agents (e.g., cyclosporine or dexamethasone) inhibited DEK secretion (See Example 6). Thus, in some embodiments, the present invention provides methods of identifying or characterizing an autoimmune disease (e.g., JRA), or response thereof to therapy, based on the level of DEK expression (e.g., mRNA transcript levels or protein).

The present invention further provides panels and kits for the detection of markers. In preferred embodiments, the presence of an autoimmune or chronic inflammatory disease marker (e.g., DEK) is used to provide a prognosis to a subject. For example, the detection of high levels of DEK, as compared to controls, in a sample is indicative of an autoimmune or chronic inflammatory disease that is active. The information provided is also used to direct the course of treatment. For example, if a subject is found to have a marker indicative of a severe state of autoimmune or chronic inflammatory disease, additional therapies (e.g., anti-inflammatories and/or immunosuppressives) can be started at a earlier point when they are more likely to be effective. In addition, if a subject is found to have an autoimmune or chronic inflammatory disease that is not responsive to a specific therapy, the expense and inconvenience of such therapies can be avoided.

The present invention is not limited to the markers described above. Any suitable marker that correlates with autoimmune or chronic inflammatory disease or the progression such disease may be utilized, including but not limited to, those described in the illustrative examples below (e.g., DEK). Additional markers are also contemplated to be within the scope of the present invention. Any suitable method may be utilized to identify and characterize autoimmune or chronic inflammatory disease markers suitable for use in the methods of the present invention, including but not limited to, those described in illustrative Examples 1-8 below. For example, in some embodiments, markers identified as being up or down-regulated in autoimmune or chronic inflammatory disease using the cellular chemotaxis methods of the present invention are further characterized using tissue microarray, immunohistochemistry, Northern blot analysis, siRNA or antisense RNA inhibition, mutation analysis, investigation of expression with clinical outcome, as well as other methods disclosed herein.

In some embodiments, the present invention provides a panel for the analysis of a plurality of markers. The panel allows for the simultaneous analysis of multiple markers correlating with autoimmune or chronic inflammatory disease. For example, a panel may include markers identified as correlating with a chronic inflammatory disease but not an autoimmune disease, an autoimmune disease but not a chronic inflammatory disease, or both, in a subject that is/are likely or not likely to respond to a given treatment. Depending on the subject, panels may be analyzed alone or in combination in order to provide the best possible diagnosis and prognosis. Markers for inclusion on a panel are selected by screening for their predictive value using any suitable method, including but not limited to, those described in the illustrative examples below.

In other embodiments, the present invention provides an expression profile map comprising expression profiles of autoimmune or chronic inflammatory disease of various severity or prognoses. Such maps can be used for comparison with patient samples. Any suitable method may be utilized, including but not limited to, by computer comparison of digitized data. The comparison data is used to provide diagnoses and/or prognoses to patients.

Detection of RNA

In some preferred embodiments, detection of autoimmune or chronic inflammatory disease markers (e.g., including but not limited to, those disclosed herein) is detected by measuring the expression of corresponding mRNA in a tissue or other sample (e.g., a blood sample). mRNA expression may be measured by any suitable method, including but not limited to, those disclosed below.

In some embodiments, RNA is detection by Northern blot analysis. Northern blot analysis involves the separation of RNA and hybridization of a complementary labeled probe.

In still further embodiments, RNA (or corresponding cDNA) is detected by hybridization to an oligonucleotide probe. A variety of hybridization assays using a variety of technologies for hybridization and detection are available. For example, in some embodiments, TaqMan assay (PE Biosystems, Foster City, Calif.; See e.g., U.S. Pat. Nos. 5,962,233 and 5,538,848, each of which is herein incorporated by reference) is utilized. The assay is performed during a PCR reaction. The TaqMan assay exploits the 5'-3' exonuclease activity of the AMPLITAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In yet other embodiments, reverse-transcriptase PCR (RT-PCR) is used to detect the expression of RNA. In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

Detection of Protein

In other embodiments, gene expression of autoimmune or chronic inflammatory disease markers is detected by measuring the expression of the corresponding protein or polypeptide. Protein expression may be detected by any suitable method. In some embodiments, proteins are detected by immunohistochemistry method. In other embodiments, proteins are detected by their binding to an antibody raised against the protein. The generation of antibodies is described below.

Antibody binding is detected by techniques known in the art (e.g., radioimmunoassay, ELISA (enzyme-linked immunosorbant assay) (See Example 5), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a prognosis based on the presence or absence of a series of proteins corresponding to autoimmune or chronic inflammatory disease markers is utilized.

In other embodiments, the immunoassay described in U.S. Pat. Nos. 5,599,677 and 5,672,480; each of which is herein incorporated by reference.

In some embodiments, the present invention provides a DEK antigen ELISA (e.g., comprising monoclonal anti-DEK antibodies (See Example 5)) to detect and/or monitor autoimmune disease (e.g., JRA/JIA). The present invention demonstrates that DEK levels are significantly increased in subjects with autoimmune disease (e.g., JRA).

Data Analysis

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., likelihood of autoimmune or chronic inflammatory disease to respond to a specific therapy) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or severity of disease.

Kits

In yet other embodiments, the present invention provides kits for the detection and characterization of autoimmune or chronic inflammatory disease. In some embodiments, the kits contain antibodies (e.g., monoclonal anti-DEK antibodies) specific for an autoimmune or chronic inflammatory disease marker (e.g., DEK), in addition to detection reagents and buffers. In other embodiments, the kits contain reagents specific for the detection of mRNA or cDNA (e.g., oligonucleotide probes or primers). In preferred embodiments, the kits contain all of the components necessary to perform a detection assay, including all controls, directions for performing assays, and any necessary software for analysis and presentation of results.

In Vivo Imaging

In some embodiments, in vivo imaging techniques are used to visualize the expression of autoimmune or chronic inflammatory disease markers in an animal (e.g., a human or non-human mammal). For example, in some embodiments, autoimmune or chronic inflammatory disease marker mRNA or protein is labeled using a labeled antibody specific for the autoimmune or chronic inflammatory disease marker. A specifically bound and labeled antibody can be detected in an individual using an in vivo imaging method, including, but not limited to, radionuclide imaging, positron emission tomography, computerized axial tomography, X-ray or magnetic resonance imaging method, fluorescence detection, and chemiluminescent detection. Methods for generating antibodies to the autoimmune or chronic inflammatory disease markers of the present invention are described below.

The in vivo imaging methods of the present invention are useful in the diagnosis and characterization (e.g., response to treatment) of autoimmune or chronic inflammatory disease that express the autoimmune or chronic inflammatory disease markers of the present invention (e.g., SLE or RA). In vivo imaging is used to visualize the presence of a marker indicative of the autoimmune or chronic inflammatory disease. Such techniques allow for diagnosis without the use of an unpleasant biopsy. The in vivo imaging methods of the present invention are also useful for providing prognoses to autoimmune or chronic inflammatory disease patients. For example, the presence of a marker indicative of autoimmune or chronic inflammatory disease likely to respond to therapy can be detected. The in vivo imaging methods of the present invention can further be used to detect sites of inflammation in multiple parts of the body.

In some embodiments, reagents (e.g., antibodies) specific for the autoimmune or chronic inflammatory disease markers of the present invention are fluorescently labeled. The labeled antibodies are introduced into a subject (e.g., orally or parenterally). Fluorescently labeled antibodies are detected using any suitable method (e.g., using the apparatus described in U.S. Pat. No. 6,198,107, herein incorporated by reference).

In some embodiments, the present invention provides compositions (e.g., monoclonal anti-DEK antibodies) and methods of monitoring relapsing-remitting (RR) multiple sclerosis (MS), as conventional magnetic resonance (MR) imaging (MRI) has proved to be a valuable tool to assess the lesion burden and activity over time (See, e.g., Rovaris and Fillipi, J Rehab Res Dev, Volume 39,243 (2002)). In some embodiments, the present invention provides methods of in vivo assessment of lung inflammatory cell activity in patients with COPD or asthma (See, Eur Respir J April; 21(4):567 (2003). The compositions and methods of the present invention are not limited to any particular autoimmune or chronic inflammatory disease. Indeed, the compositions and methods of the present invention find use in identifying, monitoring and/or treating a variety of autoimmune or chronic inflammatory diseases including, but are not limited to, autoimmune hepatitis, multiple sclerosis (MS), systemic lupus erythematosus (SLE), myasthenia gravis, type I diabetes, rheumatoid arthritis (RA), juvenile rheumatoid arthritis (JRA), juvenile idiopathic arthritis (JIA), psoriasis, Hashimoto's thyroiditis, Grave's disease, ankylosing spondylitis, Sjogrens disease, CREST syndrome, scleroderma and many more.

In other embodiments, antibodies are radioactively labeled. The use of antibodies for in vivo diagnosis is well known in the art. Sumerdon et al., (Nucl. Med. Biol 17:247-254 (1990)) have described an optimized antibody-chelator for the radioimmunoscintographic imaging of tumors using Indium-111 as the label. Griffin et al., (J Clin One 9:631-640 (1991)) have described the use of this agent in detecting tumors in patients suspected of having recurrent colorectal cancer. The use of similar agents with paramagnetic ions as labels for magnetic resonance imaging is known in the art (Lauffer, Magnetic Resonance in Medicine 22:339-342 (1991)). The label used will depend on the imaging modality chosen. Radioactive labels such as Indium-111, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used.

Radioactive metals with half-lives ranging from 1 hour to 3.5 days are available for conjugation to antibodies, such as scandium-47 (3.5 days) gallium-67 (2.8 days), gallium-68 (68 minutes), technetium-99m (6 hours), and indium-11 (3.2 days), of which gallium-67, technetium-99m, and indium-11 are preferable for gamma camera imaging, gallium-68 is preferable for positron emission tomography.

A useful method of labeling antibodies with such radiometals is by means of a bifunctional chelating agent, such as diethylenetriaminepentaacetic acid (DTPA), as described, for example, by Khaw et al. (Science 209:295 (1980)) for In-111 and Tc-99m, and by Scheinberg et al. (Science 215:1511 (1982)). Other chelating agents may also be used, but the 1-(p-carboxymethoxybenzyl) EDTA and the carboxycarbonic anhydride of DTPA are advantageous because their use permits conjugation without affecting the antibody's immunoreactivity substantially.

Another method for coupling DTPA to proteins is by use of the cyclic anhydride of DTPA, as described by Hnatowich et al. (Int. J. Appl. Radiat. Isot. 33:327 (1982)) for labeling of albumin with In-111, but which can be adapted for labeling of antibodies. A suitable method of labeling antibodies with Tc-99m which does not use chelation with DTPA is the pretinning method of Crockford et al., (U.S. Pat. No. 4,323,546, herein incorporated by reference).

A preferred method of labeling immunoglobulins with Tc-99m is that described by Wong et al. (Int. J. Appl. Radiat. Isot., 29:251 (1978)) for plasma protein, and recently applied successfully by Wong et al. (J. Nucl. Med., 23:229 (1981)) for labeling antibodies.

In the case of the radiometals conjugated to the specific antibody, it is likewise desirable to introduce as high a proportion of the radiolabel as possible into the antibody molecule without destroying its immunospecificity. A further improvement may be achieved by effecting radiolabeling in the presence of the specific autoimmune or chronic inflammatory disease marker of the present invention, to insure that the antigen binding site on the antibody will be protected. The antigen is separated after labeling.

In still further embodiments, in vivo biophotonic imaging (Xenogen, Almeda, Calif.) is utilized for in vivo imaging. This real-time in vivo imaging utilizes luciferase. The luciferase gene is incorporated into cells, microorganisms, and animals (e.g., as a fusion protein with a autoimmune and chronic inflammatory disease marker of the present invention). When active, it leads to a reaction that emits light. A CCD camera and software is used to capture the image and analyze it.

Antibodies

The present invention provides isolated antibodies. In preferred embodiments, the present invention provides monoclonal antibodies that specifically bind to an isolated polypeptide comprised of at least five amino acid residues of the autoimmune or chronic inflammatory disease marker described herein (e.g., DEK) (See Example 5). These antibodies find use in the diagnostic methods described herein.

An antibody against an autoimmune or chronic inflammatory disease protein of the present invention may be any monoclonal or polyclonal antibody, as long as it can recognize the protein. Antibodies can be produced by using a protein of the present invention as the antigen according to a conventional antibody or antiserum preparation process.

The present invention contemplates the use of both monoclonal and polyclonal antibodies. Any suitable method may be used to generate the antibodies used in the methods and compositions of the present invention, including but not limited to, those disclosed herein. For example, for preparation of a monoclonal antibody, protein, as such, or together with a suitable carrier or diluent is administered to an animal (e.g., a mammal) under conditions that permit the production of antibodies. For enhancing the antibody production capability, complete or incomplete Freund's adjuvant may be administered. Normally, the protein is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a rabbit or mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter and antiserum and then measuring the activity of the labeling agent bound to the antibody. The cell fusion can be carried out according to known methods, for example, the method described by Koehler and Milstein (Nature 256:495 (1975)). As a fusion promoter, for example, polyethylene glycol (PEG) or Sendai virus (HVJ), preferably PEG is used.

Examples of myeloma cells include NS-1, P3U1, SP2/0, AP-1 and the like. The proportion of the number of antibody producer cells (spleen cells) and the number of myeloma cells to be used is preferably about 1:1 to about 20:1. PEG (preferably PEG 1000-PEG 6000) is preferably added in concentration of about 10% to about 80%. Cell fusion can be carried out efficiently by incubating a mixture of both cells at about 20° C. to about 40° C., preferably about 30° C. to about 37° C. for about 1 minute to 10 minutes.

Various methods may be used for screening for a hybridoma producing the antibody (e.g., against a autoimmune or chronic inflammatory disease protein or autoantibody of the present invention). For example, where a supernatant of the hybridoma is added to a solid phase (e.g., microplate) to which antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20% fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., preferably 37° C. for about 5 days to 3 weeks, preferably 1 week to 2 weeks under about 5% $CO_2$ gas. The antibody titer of the supernatant of a hybridoma culture can be measured according to the same manner as described above with respect to the antibody titer of the anti-protein in the antiserum.

Separation and purification of a monoclonal antibody (e.g., against an autoimmune or chronic inflammatory disease marker of the present invention) can be carried out according to the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

Polyclonal antibodies may be prepared by any known method or modifications of these methods including obtaining antibodies from patients. For example, a complex of an immunogen (an antigen against the protein) and a carrier protein is prepared and an animal is immunized by the complex according to the same manner as that described with respect to the above monoclonal antibody preparation. A material containing the antibody against is recovered from the immunized animal and the antibody is separated and purified.

As to the complex of the immunogen and the carrier protein to be used for immunization of an animal, any carrier protein and any mixing proportion of the carrier and a hapten can be employed as long as an antibody against the hapten, which is crosslinked on the carrier and used for immunization, is produced efficiently. For example, bovine serum albumin, bovine cycloglobulin, keyhole limpet hemocyanin, etc. may be coupled to an hapten in a weight ratio of about 0.1 part to about 20 parts, preferably, about 1 part to about 5 parts per 1 part of the hapten.

In addition, various condensing agents can be used for coupling of a hapten and a carrier. For example, glutaraldehyde, carbodiimide, maleimide activated ester, activated ester reagents containing thiol group or dithiopyridyl group, and the like find use with the present invention. The condensation product as such or together with a suitable carrier or diluent is administered to a site of an animal that permits the antibody production. For enhancing the antibody production capability, complete or incomplete Freund's adjuvant may be administered. Normally, the protein is administered once every 2 weeks to 6 weeks, in total, about 3 times to about 10 times.

The polyclonal antibody is recovered from blood, ascites and the like, of an animal immunized by the above method. The antibody titer in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The protein used herein as the immunogen is not limited to any particular type of immunogen. For example, an autoimmune or chronic inflammatory disease marker of the present invention (further including a gene having a nucleotide sequence partly altered) can be used as the immunogen. Further, fragments of the protein may be used. Fragments may be obtained by any methods including, but not limited to expressing a fragment of the gene, enzymatic processing of the protein, chemical synthesis, and the like.

Drug Screening

In some embodiments, the present invention provides drug screening assays (e.g., to screen for anti-autoimmune or anti-chronic inflammatory disease drugs). The screening methods of the present invention utilize autoimmune or chronic inflammatory disease markers identified using the methods of the present invention (e.g., including but not limited to, DEK). For example, in some embodiments, the present invention provides methods of screening for compound that alter (e.g., increase or decrease) the expression of autoimmune or chronic inflammatory disease marker genes. In some embodiments, candidate compounds are antisense agents (e.g., oligonucleotides) directed against autoimmune or chronic inflammatory disease markers. See below for a discussion of antisense therapy. In other embodiments, candidate compounds are antibodies that specifically bind to an autoimmune or chronic inflammatory disease marker of the present invention.

In one screening method, candidate compounds are evaluated for their ability to alter autoimmune or chronic inflammatory disease marker expression by contacting a compound with a cell expressing a autoimmune or chronic inflammatory disease marker and then assaying for the effect of the candidate compounds on expression. In some embodiments, the effect of candidate compounds on expression of an autoimmune or chronic inflammatory disease marker gene is assayed for by detecting the level of autoimmune or chronic inflammatory disease marker mRNA expressed by the cell. mRNA expression can be detected by any suitable method. In other embodiments, the effect of candidate compounds on expression of autoimmune or chronic inflammatory disease marker genes is assayed by measuring the level of polypeptide encoded by the autoimmune or chronic inflammatory disease markers (See, e.g., Example 5). The level of polypeptide expressed can be measured using any suitable method, including but not limited to, those disclosed herein.

Specifically, the present invention provides screening methods for identifying modulators, i.e., candidate or test compounds or agents (e.g., proteins, peptides, peptidomimetics, peptoids, small molecules or other drugs) which bind to autoimmune or chronic inflammatory disease markers (e.g., DEK) of the present invention, have an inhibitory (or stimulatory) effect on, for example, autoimmune or chronic inflammatory disease marker expression or autoimmune or chronic inflammatory disease markers activity, or have a stimulatory or inhibitory effect on, for example, the expression or activity of an autoimmune or chronic inflammatory disease marker substrate. Compounds thus identified can be used to modulate the activity of target gene products (e.g., autoimmune or chronic inflammatory disease marker genes) either directly or indirectly in a therapeutic protocol, to elaborate the biological function of the target gene product, or to identify compounds that disrupt normal target gene interactions. Compounds which inhibit the activity or expression of autoimmune or chronic inflammatory disease markers are useful in the treatment of autoimmune or chronic inflammatory disease (e.g., JRA, etc.)

In one embodiment, the invention provides assays for screening candidate or test compounds that are substrates of an autoimmune or chronic inflammatory disease marker protein or polypeptide or a biologically active portion thereof. In another embodiment, the invention provides assays for screening candidate or test compounds that bind to or modulate the activity of an autoimmune or chronic inflammatory disease marker protein or polypeptide or a biologically active portion thereof.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 (1994)); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 (1993); Erb et al., Proc. Nad. Acad. Sci. USA 91:11422 (1994); Zuckermann et al., J. Med. Chem. 37:2678 (1994); Cho et al., Science 261:1303 (1993); Carrell et al., Angew. Chem. Int. Ed. Engl. 33.2059 (1994); Carell et al., Angew. Chem. Int. Ed. Engl. 33:2061 (1994); and Gallop et al., J. Med. Chem. 37:1233 (1994).

Libraries of compounds may be presented in solution (e.g., Houghten, Biotechniques 13:412-421 (1992)), or on beads (Lam, Nature 354:82-84 (1991)), chips (Fodor, Nature 364: 555-556 (1993)), bacteria or spores (U.S. Pat. No. 5,223,409; herein incorporated by reference), plasmids (Cull et al., Proc. Nad. Acad. Sci. USA 89:18651869 (1992)) or on phage (Scott and Smith, Science 249:386-390 (1990); Devlin Science 249: 404-406 (1990); Cwirla et al., Proc. Natl. Acad. Sci. 87:6378-6382 (1990); Felici, J. Mol. Biol. 222:301 (1991)).

In one embodiment, an assay is a cell-based assay in which a cell that expresses an autoimmune or chronic inflammatory disease marker protein or biologically active portion thereof is contacted with a test compound, and the ability of the test compound to modulate the autoimmune or chronic inflammatory disease marker's activity is determined. Determining the ability of the test compound to modulate autoimmune or chronic inflammatory disease marker activity can be accomplished by monitoring, for example, B cell stimulation, changes in enzymatic activity, or chromatin structure (e.g., supercoiling of DNA). The cell, for example, can be of mammalian origin. In some embodiments, the interaction of DEK with other proteins can be characterized in the presence or absence of a test compound. For example, in some embodiments, the interaction of DEK with ALY can be characterized (e.g., by detecting direct interaction between the proteins or by characterizing chromatin structure) in the absence of a test compound and in the presence of a test compound.

The ability of the test compound to modulate autoimmune or chronic inflammatory disease marker binding to a compound, e.g., an autoimmune or chronic inflammatory disease marker substrate, can also be evaluated. This can be accomplished, for example, by coupling the compound, e.g., the substrate, with a radioisotope or enzymatic label such that binding of the compound, e.g., the substrate, to an autoimmune or chronic inflammatory disease marker can be determined by detecting the labeled compound, e.g., substrate, in a complex.

Alternatively, the autoimmune or chronic inflammatory disease marker is coupled with a radioisotope or enzymatic label to monitor the ability of a test compound to modulate autoimmune or chronic inflammatory disease marker binding to an autoimmune or chronic inflammatory disease markers substrate in a complex. For example, compounds (e.g., substrates) can be labeled with $^{125}I$, $^{35}S$ $^{14}C$ or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., an autoimmune or chronic inflammatory disease marker substrate) to interact with an autoimmune or chronic inflammatory disease marker with or without the labeling of any of the interactants can be evaluated. For example, a microphysiometer can be used to detect the interaction of a compound with an autoimmune or chronic inflammatory disease marker without the labeling of either the compound or the autoimmune or chronic inflammatory disease marker (McConnell et al. Science 257:1906-1912 (1992)). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and autoimmune or chronic inflammatory disease markers.

In yet another embodiment, a cell-free assay is provided in which an autoimmune or chronic inflammatory disease marker protein or biologically active portion thereof is contacted with a test compound and the ability of the test compound to bind to the autoimmune or chronic inflammatory disease marker protein or biologically active portion thereof is evaluated. Preferred biologically active portions of the autoimmune or chronic inflammatory disease markers proteins to be used in assays of the present invention include fragments that participate in interactions with substrates or other proteins, e.g., fragments with high surface probability scores.

Cell-free assays involve preparing a reaction mixture of the autoimmune or chronic inflammatory disease target gene protein and the test compound under conditions and for a time sufficient to allow the two components to interact and bind, thus forming a complex that can be removed and/or detected.

The interaction between two molecules can also be detected, e.g., using fluorescence energy transfer (FRET) (see, for example, Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule may simply utilize the natural fluorescent energy of tryptophan residues.

Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in 1 5 the assay should be maximal. An FRET binding event can be conveniently measured through standard fluorometric detection means well known in the art (e.g., using a fluorimeter).

In another embodiment, determining the ability of the autoimmune or chronic inflammatory disease marker proteins to bind to a target molecule can be accomplished using real-time Biomolecular Interaction Analysis (BIA) (see, e.g., Sjolander and Urbaniczky, Anal. Chem. 63:2338-2345 (1991) and Szabo et al. Curr. Opin. Struct. Biol. 5:699-705 (1995)). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize autoimmune or chronic inflammatory disease markers, an anti-autoimmune or anti-chronic inflammatory disease marker antibody or its target molecule to facilitate separation of complexed from non-complexed forms of one or both of the proteins, as well as to accommodate automation of the assay. Binding of a test compound to an autoimmune or chronic inflammatory disease marker protein, or interaction of an autoimmune or chronic inflammatory disease marker protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase-autoimmune or chronic inflammatory disease marker fusion proteins or glutathione-S-transferase/target fusion proteins can be adsorbed onto glutathione Sepharose beads (Sigma Chemical, St. Louis, Mo.) or glutathione-derivatized microtiter plates, which are then combined with the test compound or the test compound and either the non-adsorbed target protein or autoimmune or chronic inflammatory disease marker protein, and the mixture incubated under conditions conducive for complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of autoimmune or chronic inflammatory disease markers binding or activity determined using standard techniques. Other techniques for immobilizing either autoimmune or chronic inflammatory disease marker proteins or a target molecule on matrices include using conjugation of biotin and streptavidin. Biotinylated autoimmune or chronic inflammatory disease marker protein or target molecules can be prepared from biotin-NHS (N-hydroxy-succinimide) using techniques known in the art (e.g., biotinylation kit, Pierce Chemicals, Rockford, EL), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-IgG antibody).

This assay is performed utilizing antibodies reactive with autoimmune or chronic inflammatory disease marker protein or target molecules but which do not interfere with binding of the autoimmune or chronic inflammatory disease marker proteins to its target molecule. Such antibodies can be derivatized to the wells of the plate, and unbound target or autoimmune or chronic inflammatory disease marker proteins trapped in the wells by antibody conjugation. Methods for detecting such complexes, in addition to those described above for the GST-immobilized complexes, include immunodetection of complexes using antibodies reactive with the autoimmune or chronic inflammatory disease marker protein or target molecule, as well as enzyme-linked assays which rely on detecting an enzymatic activity associated with the autoimmune or chronic inflammatory disease marker protein or target molecule.

Alternatively, cell free assays can be conducted in a liquid phase. In such an assay, the reaction products are separated from unreacted components, by any of a number of standard techniques, including, but not limited to: differential centrifugation (See, e.g., Rivas and Minton, Trends Biochem Sci 18:284-7 (1993)); chromatography (gel filtration chromatography, ion-exchange chromatography); electrophoresis (See, e.g., Ausubel et al., eds. Current Protocols in Molecular Biology 1999, J. Wiley: New York); and immunoprecipitation (See, e.g., for example, Ausubel et al., eds. Current Protocols in Molecular Biology 1999, J. Wiley: New York). Such resins and chromatographic techniques are known to one skilled in the art (See e.g., Heegaard J. Mol. Recognit. 11:141-8 (1998); Hageand Tweed J. Chromatogr. Biomed. Sci. Appl 699:499-525 (1997)). Further, fluorescence energy transfer may also be conveniently utilized, as described herein, to detect binding without further purification of the complex from solution.

The assay can include contacting the autoimmune or chronic inflammatory disease marker protein or biologically active portion thereof with a known compound that binds the autoimmune or chronic inflammatory disease marker to form an assay mixture, contacting the assay mixture with a test compound, and determining the ability of the test compound to interact with an autoimmune or chronic inflammatory disease marker protein, wherein determining the ability of the test compound to interact with an autoimmune or chronic inflammatory disease marker protein includes determining the ability of the test compound to preferentially bind to autoimmune or chronic inflammatory disease markers or biologically active portion thereof, or to modulate the activity of a target molecule, as compared to the known compound.

To the extent that autoimmune or chronic inflammatory disease markers can, in vivo, interact with one or more cellular or extracellular macromolecules, such as proteins, inhibitors of such an interaction are useful. A homogeneous assay can be used can be used to identify inhibitors.

For example, a preformed complex of the target gene product and the interactive cellular or extracellular binding partner product is prepared such that either the target gene products or their binding partners are labeled, but the signal generated by the label is quenched due to complex formation (see, e.g., U.S. Pat. No. 4,109,496, herein incorporated by reference, that utilizes this approach for immunoassays). The addition of a test substance that competes with and displaces one of the species from the preformed complex will result in the generation of a signal above background. In this way, test substances that disrupt target gene product-binding partner interaction can be identified. Alternatively, autoimmune or chronic inflammatory disease marker protein can be used as a "bait protein" in a two-hybrid assay or three-hybrid assay (see, e.g., U.S. Pat. No. 5,283,317; Zervos et al., Cell 72:223-232 (1993); Madura et al., J. Biol. Chem. 268.12046-12054 (1993); Bartel et al., Biotechniques 14:920-924 (1993); Iwabuchi et al., Oncogene 8:1693-1696 (1993); and Brent WO 94/10300; each of which is herein incorporated by reference), to identify other proteins, that bind to or interact with autoimmune or chronic inflammatory disease marker ("autoimmune disease- or chronic inflammatory disease-binding proteins") and are involved in autoimmune or chronic inflammatory disease marker activity. Such autoimmune or chronic inflammatory disease marker-binding proteins can be activators or inhibitors of signals by the autoimmune or chronic inflammatory disease marker proteins or targets as, for example, downstream elements of an autoimmune or chronic inflammatory disease markers-mediated signaling pathway.

Modulators of autoimmune or chronic inflammatory disease marker expression can also be identified. For example, a cell or cell free mixture is contacted with a candidate compound and the expression of autoimmune or chronic inflammatory disease marker mRNA or protein evaluated relative to the level of expression of autoimmune or chronic inflammatory disease marker mRNA or protein in the absence of the candidate compound. When expression of autoimmune or chronic inflammatory disease marker mRNA or protein is greater in the presence of the candidate compound than in its absence, the candidate compound is identified as a stimulator of autoimmune or chronic inflammatory disease marker mRNA or protein expression (e.g., IL-8, See Example 6). Alternatively, when expression of autoimmune or chronic inflammatory disease marker mRNA or protein is less (i.e., statistically significantly less) in the presence of the candidate compound than in its absence, the candidate compound is identified as an inhibitor of autoimmune or chronic inflammatory disease marker mRNA or protein expression. The level of autoimmune or chronic inflammatory disease marker mRNA or protein expression can be determined by methods described herein for detecting autoimmune or chronic inflammatory disease markers mRNA or protein.

A modulating agent can be identified using a cell-based or a cell free assay, and the ability of the agent to modulate the activity of an autoimmune or chronic inflammatory disease marker protein can be confirmed in vivo, e.g., in an animal such as an animal model for a disease (e.g., an animal with lupus or arthritis) or T cells from an autoimmune or chronic inflammatory disease subject, or cells from an autoimmune or chronic inflammatory disease cell line.

This invention further pertains to novel agents identified by the above-described screening assays (See e.g., below description of autoimmune or chronic inflammatory disease therapies). Accordingly, it is within the scope of this invention to further use an agent identified as described herein (e.g., an autoimmune or chronic inflammatory disease marker modulating agent, an antisense autoimmune or chronic inflammatory disease marker nucleic acid molecule, a siRNA molecule, an autoimmune or chronic inflammatory disease marker specific antibody, or an autoimmune or chronic inflammatory disease marker-binding partner) in an appropriate animal model (such as those described herein) to determine the efficacy, toxicity, side effects, or mechanism of action, of treatment with such an agent. Furthermore, novel agents identified by the above-described screening assays can be used for treatments, for example, as described herein.

Autoimmune and/or Chronic Inflammatory Disease Therapies

In some embodiments, the present invention provides therapies for autoimmune or chronic inflammatory disease (e.g., JRA). In some embodiments, therapies target an autoimmune or chronic inflammatory disease marker (e.g., DEK).

Antisense Therapies

Figure 12:
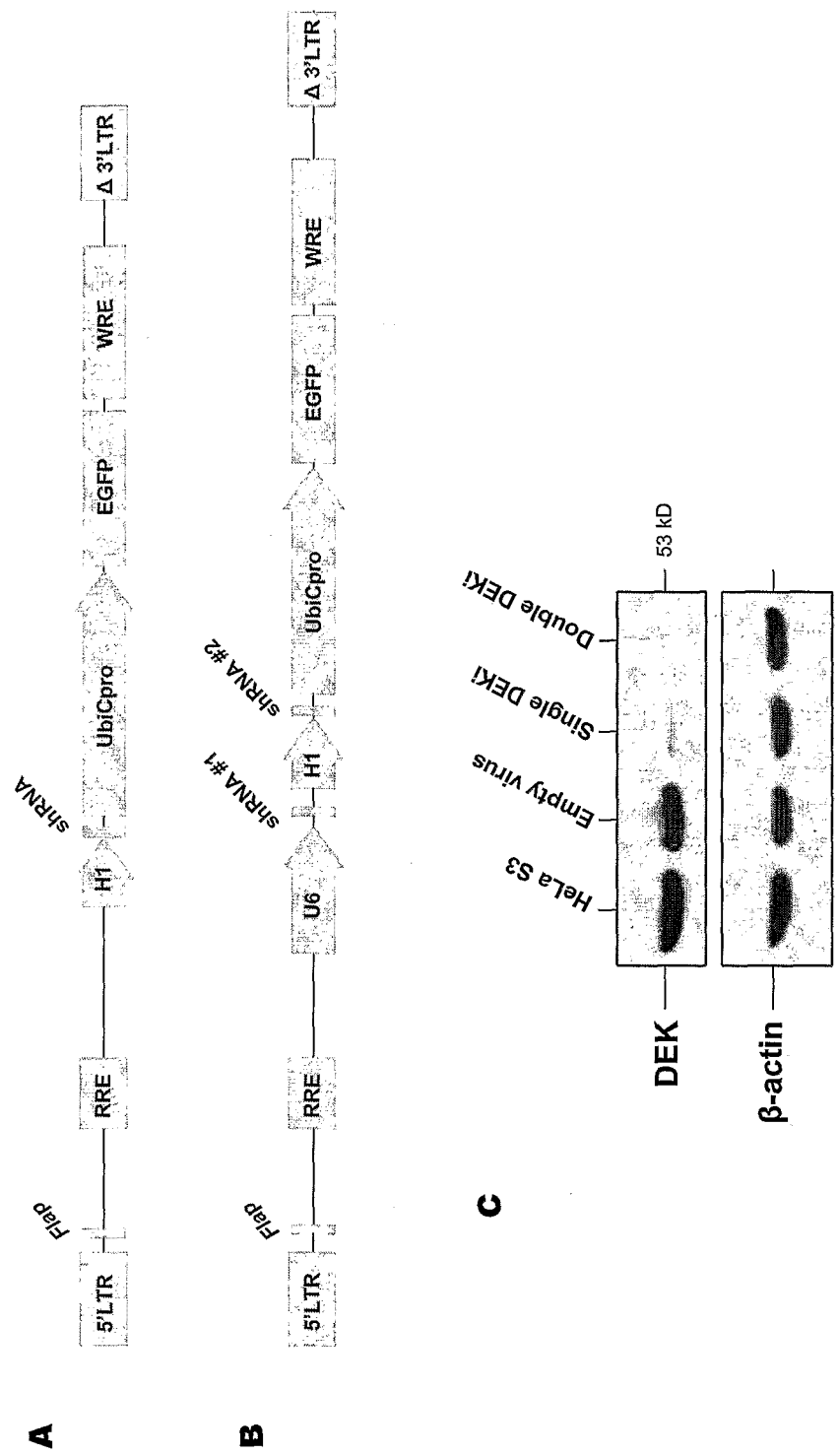
FIG. 12. shows lentiviral shRNA-mediated knockdown of DEK.

In some embodiments, the present invention targets the expression of an autoimmune or chronic inflammatory disease marker. For example, in some embodiments, the present invention employs compositions comprising oligomeric antisense compounds, particularly oligonucleotides (e.g., those identified in the drug screening methods described above), for use in modulating the function of nucleic acid molecules encoding an autoimmune or chronic inflammatory disease marker of the present invention, ultimately modulating the amount of autoimmune or chronic inflammatory disease marker expressed (See, e.g., FIG. 12, and Example 9 herein). This is accomplished by providing antisense compounds that specifically hybridize with one or more nucleic acids encoding an autoimmune or chronic inflammatory disease marker of the present invention. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription (e.g., via transcription factor decoys). The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is modulation of the expression of autoimmune or chronic inflammatory disease markers of the present invention. In the context of the present invention, "modulation" means either an increase (stimulation) or a decrease (inhibition) in the expression of a gene. For example, expression may be inhibited to potentially prevent inflammation or autoimmune disease (e.g., JRA) or autoimmune disease symptoms (e.g., swelling, joint pain, etc.). For example, any means may be used to for modulation including RNAi (See, e.g., U.S. Pat. No. 6,897,069, and U.S. patent application Ser. No. 10/397,943, filed Mar. 26, 2003, herein incorporated by reference in their entireties for all purposes). In some embodiments, inhibiting DEK gene expression (e.g., using RNAi) inhibits interaction of DEK with other proteins (e.g., ALY) due to a decrease in the presence of DEK protein.

It is preferred to target specific nucleic acids for antisense. "Targeting" an antisense compound to a particular nucleic acid, in the context of the present invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding an autoimmune or chronic inflammatory disease marker of the present invention (e.g., DEK). The targeting process also includes determination of a site or sites within this gene for the antisense interaction to occur such that the desired effect (e.g., detection or modulation of expression of the protein) will result. Within the context of the present invention, a preferred intragenic site is the region encompassing the translation initiation or termination codon of the open reading frame (ORF) of the gene. Since the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the present invention, "start codon" and "translation initiation codon" refer to the codon or codons that are used in vivo to initiate translation of an mRNA molecule transcribed from a gene encoding a tumor antigen of the present invention, regardless of the sequence(s) of such codons.

Translation termination codon (or "stop codon") of a gene may have one of three sequences (i.e., 5'-UAA, 5'-UAG and 5'-UGA; the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which refers to the region between the translation initiation codon and the translation termination codon, is also a region that may be targeted effectively. Other target regions include the 5' untranslated region (5' UTR), referring to the portion of an mRNA in the 5' direction from the translation initiation codon, and thus including nucleotides between the 5' cap site and the translation initiation codon of an mRNA or corresponding nucleotides on the gene, and the 3' untranslated region (3' UTR), referring to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The cap region may also be a preferred target region.

Although some eukaryotic mRNA transcripts are directly translated, many contain one or more regions, known as "introns," that are excised from a transcript before it is translated. The remaining (and therefore translated) regions are known as "exons" and are spliced together to form a continuous mRNA sequence. mRNA splice sites (i.e., intron-exon junctions) may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

In some embodiments, target sites for antisense inhibition are identified using commercially available software programs (e.g., Biognostik, Gottingen, Germany; SysArris Software, Bangalore, India; Antisense Research Group, University of Liverpool, Liverpool, England; GeneTrove, Carlsbad, Calif.). In other embodiments, target sites for antisense inhibition are identified using the accessible site method described in U.S. Patent WO0198537A2, herein incorporated by reference.

Once one or more target sites have been identified, oligonucleotides are chosen that are sufficiently complementary to the target (i.e., hybridize sufficiently well and with sufficient specificity) to give the desired effect. For example, in preferred embodiments of the present invention, antisense oligonucleotides are targeted to or near the start codon.

In the context of this invention, "hybridization," with respect to antisense compositions and methods, means hydrogen bonding, which may be Watson-Crick, Hoogsteen or reversed Hoogsteen hydrogen bonding, between complementary nucleoside or nucleotide bases. For example, adenine and thymine are complementary nucleobases that pair through the formation of hydrogen bonds. It is understood that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired (i.e., under physiological conditions in the case of in vivo assays or therapeutic treatment, and in the case of in vitro assays, under conditions in which the assays are performed).

Antisense compounds are commonly used as research reagents and diagnostics. For example, antisense oligonucleotides, which are able to inhibit gene expression with specificity, can be used to elucidate the function of particular genes. Antisense compounds are also used, for example, to distinguish between functions of various members of a biological pathway.

The specificity and sensitivity of antisense is also applied for therapeutic uses. For example, antisense oligonucleotides have been employed as therapeutic moieties in the treatment of disease states in animals and humans. Antisense oligonucleotides have been safely and effectively administered to humans and numerous clinical trials are presently underway. It is thus established that oligonucleotides are useful therapeutic modalities that can be configured to be useful in treatment regimes for treatment of cells, tissues, and animals, especially humans.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 30 nucleobases (i.e., from about 8 to about 30 linked bases), although both longer and shorter sequences may find use with the present invention. Particularly preferred antisense compounds are antisense oligonucleotides, even more preferably those comprising from about 12 to about 25 nucleobases.

Specific examples of preferred antisense compounds useful with the present invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In other preferred oligonucleotide mimetics, both the sugar and the internucleoside linkage (i.e., the backbone) of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference.

Further teaching of PNA compounds can be found in Nielsen et al., Science 254:1497 (1991).

Most preferred embodiments of the invention are oligonucleotides with phosphorothioate backbones and oligonucleosides with heteroatom backbones, and in particular —$CH_2$—, —NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$—, and —O—N($CH_3$)—$CH_2$—$CH_2$— (wherein the native phosphodiester backbone is represented as —O—P—O—$CH_2$—) of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O(($CH_2$)$_n$O)$_m$$CH_3$, O($CH_2$)$_n$O$CH_3$, O($CH_2$)$_n$$NH_2$, O($CH_2$)$_n$$CH_3$, O($CH_2$)$_n$$ONH_2$, and O($CH_2$)$_n$ON(($CH_2$)$_n$$CH_3$))$_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, S$CH_3$, OCN, Cl, Br, CN, $CF_3$, O$CF_3$, SO$CH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al, Helv. Chim. Acta 78:486 (1995)) i.e., an alkoxyalkoxy group. A further preferred modification includes 2'-dimethylaminooxyethoxy (i.e., a O($CH_2$)$_2$ON($CH_3$)$_2$ group), also known as 2'-DMAOE, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$.

Other preferred modifications include 2'-methoxy(2'-O—$CH_3$), 2'-aminopropoxy(2'-O$CH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2. degree ° C. and are presently preferred base substitutions, even more particularly when combined with 2'-O-methoxyethyl sugar modifications.

Another modification of the oligonucleotides of the present invention involves chemically linking to the oligonucleotide one or more moieties or conjugates that enhance the activity, cellular distribution or cellular uptake of the oligonucleotide. Such moieties include but are not limited to lipid moieties such as a cholesterol moiety, cholic acid, a thioether, (e.g., hexyl-5-tritylthiol), a thiocholesterol, an aliphatic chain, (e.g., dodecandiol or undecyl residues), a phospholipid, (e.g., di-hexadecyl-rac-glycerol or triethylammonium 1,2-di-O-hexadecyl-rac-glycero-3-H-phosphonate), a polyamine or a polyethylene glycol chain or adamantane acetic acid, a palmityl moiety, or an octadecylamine or hexylamino-carbonyl-oxycholesterol moiety.

One skilled in the relevant art knows well how to generate oligonucleotides containing the above-described modifications. The present invention is not limited to the antisense oligonucleotides described above. Any suitable modification or substitution may be utilized.

It is not necessary for all positions in a given compound to be uniformly modified, and in fact more than one of the aforementioned modifications may be incorporated in a single compound or even at a single nucleoside within an oligonucleotide. The present invention also includes antisense compounds that are chimeric compounds. "Chimeric" antisense compounds or "chimeras," in the context of the present invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNaseH is a cellular endonuclease that cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the present invention may be formed as composite structures of two or more oligonucleotides, modified oligonucleotides, oligonucleosides and/or oligonucleotide mimetics as described above.

The present invention also includes pharmaceutical compositions and formulations that include the antisense compounds of the present invention as described below.

Genetic Therapies

The present invention contemplates the use of any genetic manipulation for use in modulating the expression of autoimmune or chronic inflammatory disease markers of the present invention. Examples of genetic manipulation include, but are not limited to, gene knockout (e.g., removing the autoimmune and chronic inflammatory disease marker gene from the chromosome using, for example, recombination), expression of antisense constructs with or without inducible promoters, and the like (See, e.g., Example 9). Delivery of nucleic acid construct to cells in vitro or in vivo may be conducted using any suitable method. A suitable method is one that introduces the nucleic acid construct into the cell such that the desired event occurs (e.g., expression of an antisense construct).

Introduction of molecules carrying genetic information into cells is achieved by any of various methods including, but not limited to, directed injection of naked DNA constructs, bombardment with gold particles loaded with said constructs, and macromolecule mediated gene transfer using, for example, liposomes, biopolymers, and the like. Preferred methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo. Examples of adenoviral vectors and methods for gene transfer are described in PCT publications WO 00/12738 and WO 00/09675 and U.S. Pat. Nos. 6,033,908, 6,019,978, 6,001,557, 5,994,132, 5,994,128, 5,994,106, 5,981,225, 5,885,808, 5,872,154, 5,830,730, and 5,824,544, each of which is herein incorporated by reference in its entirety.

Vectors may be administered to subject in a variety of ways. For example, in some embodiments, administration is via the blood or lymphatic circulation (See e.g., PCT publication 99/02685 herein incorporated by reference in its entirety). Exemplary dose levels of adenoviral vector are preferably $10^8$ to $10^{11}$ vector particles added to the perfusate.

Antibody Therapy

In some embodiments, the present invention provides antibodies that target cells that express an autoimmune or chronic inflammatory disease marker of the present invention (e.g., DEK) (See Examples 1 and 5). Any suitable antibody (e.g., monoclonal, polyclonal, or synthetic) may be utilized in the therapeutic methods disclosed herein. In preferred embodiments, the antibodies used for autoimmune or chronic inflammatory disease therapy are humanized antibodies. Methods for humanizing antibodies are well known in the art (See e.g., U.S. Pat. Nos. 6,180,370, 5,585,089, 6,054,297, and 5,565,332; each of which is herein incorporated by reference).

In some embodiments, the therapeutic antibodies comprise an antibody generated against an autoimmune or chronic inflammatory disease marker of the present invention, wherein the antibody is conjugated to a cytotoxic agent. In some embodiments, an autoimmune or chronic inflammatory disease specific therapeutic agent is generated that does not target normal cells, thus reducing many of the detrimental side effects of traditional chemotherapy. For certain applications, it is envisioned that the therapeutic agents will be pharmacologic agents that will serve as useful agents for attachment to antibodies, particularly cytotoxic or otherwise anticellular agents having the ability to kill or suppress the growth or cell division of autoreactive cells (e.g., autoreactive macrophages, or T and B cells). The present invention contemplates the use of any pharmacologic agent that can be conjugated to an antibody, and delivered in active form. Exemplary anticellular agents include chemotherapeutic agents, radioisotopes, and cytotoxins. The therapeutic antibodies of the present invention may include a variety of cytotoxic moieties, including but not limited to, radioactive isotopes (e.g., iodine-131, iodine-123, technetium-99m, indium-111, rhenium-188, rhenium-186, gallium-67, copper-67, yttrium-90, iodine-125 or astatine-211), hormones such as a steroid, antimetabolites such as cytosines (e.g., arabinoside, fluorouracil, methotrexate or aminopterin; an anthracycline; mitomycin C), vinca alkaloids (e.g., demecolcine; etoposide; mithramycin), and antitumor alkylating agent such as chlorambucil or melphalan. Other embodiments may include agents such as a coagulant, a cytokine, growth factor, bacterial endotoxin or the lipid A moiety of bacterial endotoxin. For example, in some embodiments, therapeutic agents will include plant-, fungus- or bacteria-derived toxin, such as an A chain toxins, a ribosome inactivating protein, α-sarcin, aspergillin, restrictocin, a ribonuclease, diphtheria toxin or pseudomonas exotoxin, to mention just a few examples. In some preferred embodiments, deglycosylated ricin A chain is utilized.

In any event, it is proposed that agents such as these may, if desired, be successfully conjugated to an antibody, in a manner that will allow their targeting, internalization, release or presentation to blood components at the site of the targeted autoimmune or chronic inflammatory diseased cells as required using known conjugation technology (See, e.g., Ghose et al., Methods Enzymol., 93:280 (1983)).

For example, in some embodiments the present invention provides immunotoxins targeting an autoimmune or chronic inflammatory disease marker of the present invention (e.g., DEK). Immunotoxins are conjugates of a specific targeting agent typically a tumor-directed antibody or fragment, with a cytotoxic agent, such as a toxin moiety. The targeting agent directs the toxin to, and thereby selectively kills, cells carrying the targeted antigen. In some embodiments, therapeutic antibodies employ crosslinkers that provide high in vivo stability (Thorpe et al., Cancer Res., 48:6396 (1988)).

In preferred embodiments, antibody based therapeutics are formulated as pharmaceutical compositions as described below. In preferred embodiments, administration of an antibody composition of the present invention results in a measurable decrease in autoimmune or chronic inflammatory disease (e.g., decrease or elimination T cell autoreactivity).

Pharmaceutical Compositions

The present invention further provides pharmaceutical compositions (e.g., comprising the antisense or antibody compounds described above). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Dosing is dependent on severity and responsiveness of the autoimmune or chronic inflammatory disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models or based on the examples described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide is administered in maintenance doses, ranging from 0.01 µg to 100 g per kg of body weight, once or more daily, to once every 20 years.

Reducing Chemotaxis and Inflammation

The present invention provides a method for reducing inflammation in a tissue in a subject (e.g., a subject with autoimmune disease), comprising: a) providing: i) a tissue; and ii) an agent (e.g., an anti-DEK antibody or siRNA) that inhibits DEK expression (e.g., nucleic acid and/or protein) and/or DEK activity (e.g., ability to recruit neutrophils, $CD8^+$ T cells and/or NK cells); and b) administering the agent to the tissue such that inflammation in the tissue is reduced in the presence of the agent compared to in the absence of the agent.

The present invention also provides a method of inhibiting chemotaxis of cells (e.g., neutrophils, $CD8^+$ T cells and/or NK cells) into an inflammatory site (e.g., a joint) comprising: a) providing: i) a subject; and ii) an agent (e.g., an anti-DEK antibody or siRNA) that inhibits DEK expression (e.g., nucleic acid and/or protein) and/or DEK activity (e.g., ability to recruit neutrophils, $CD8^+$ T cells and/or NK cells); and b) administering the agent to the subject such that chemotaxis of cells into an inflammatory site in the subject is reduced in the presence of the agent compared to in the absence of the agent. In some embodiments, the agent is co-administered with one or more other agents (e.g., an immunosuppressive or anti-inflammatory agent).

Accordingly, the present invention also provides methods involving co-administration of compounds comprising DEK inhibitors (e.g., anti-DEK antibodies, siRNAs, and the like) with one or more additional active agents (e.g., an immunosuppressive or anti-inflammatory agent, etc.). Indeed, it is a further aspect of this invention to provide methods for enhancing prior art therapies and/or pharmaceutical compositions by co-administering a composition comprising a DEK inhibitor of this invention. In co-administration procedures, the agents may be administered concurrently or sequentially. In one embodiment, the compounds described herein are administered prior to the other active agent(s). The pharmaceutical formulations and modes of administration may be any of those described above. In addition, the two or more co-administered agents may each be administered using different modes or different formulations. The agent or agents to be co-administered depends on the type of condition being treated. For example, when the condition being treated is inflammation (e.g., associated with an inflammatory disease), the additional agent can be an anti-inflammatory agent (e.g., including, but not limited to, prednisone; dexamethasone; cyclooxygenase inhibitors including COX-1 and COX-2 inhibitors, aspirin, indomethacin, ibuprofen, piroxicam, Naproxen, CELEBREX and VIOXX; CTLA4-Ig agonists and antagonists; CD40 ligand antagonists; IMPDH inhibitors including mycophenolate; integrin antagonists; alpha-4 beta-7 integrin antagonists; cell adhesion inhibitors; interferon gamma antagonists; ICAM-1; tumor necrosis factor antagonists selected from infliximab, OR1384, TNF-alpha inhibitors including tenidap, anti-TNF antibodies or soluble TNF receptors including etanercept; rapamycin selected from sirolimus and Rapamune; eflunomide; prostaglandin synthesis inhibitors; budesonide; clofazimine; CNI-1493; CD4 antagonists including priliximab; p38 mitogen-activated protein kinase inhibitors; protein tyrosine kinase inhibitors; IKK inhibitors, cyclosporins; cyclosporin A; anti-IL-2 receptor; anti-CD45RB; anti-CD2; anti-CD3 (OKT-3); anti-CD4; anti-CD80; anti-CD86; monoclonal antibody OKT3; agents blocking the interaction between CD40 and gp39; antibodies specific for CD40 and/or gp39; CD154; fusion proteins constructed from CD40 and gp39; CD40Ig; CD8gp39; nuclear translocation inhibitors of NF-kappa B function; deoxyspergualin; gold compounds; antiproliferative agents selected from methotrexate, FK506, tacrolimus, Prograf and mycophenolate mofetil; cytotoxic drugs selected from azathiprine and cyclophosphamide; anticytokines selected from antiIL-4 or IL-4 receptor fusion proteins; PDE 4 inhibitors including Ariflo and PTK inhibitors. The additional agents to be co-administered, such as anti-inflammatories or immunosuppressives, can be any of the well-known agents in the art, including, but not limited to, those that are currently in clinical use.

Treatment of the various diseases and disorders described herein are often generally limited by the following two major factors: (1) the development of drug resistance and (2) the toxicity of known therapeutic agents. Some therapeutic agents have deleterious side effects, including non-specific lymphotoxicity and renal toxicity.

The methods described herein address both these problems. Drug resistance, where increasing dosages are required to achieve therapeutic benefit, is overcome by co-administering the compounds comprising a DEK inhibitor (e.g., antibody or siRNA) described herein with the known agent. In some embodiments, the compounds described herein sensitize target cells to known agents (and vice versa) and, accordingly, less of these agents are needed to achieve a therapeutic benefit.

The sensitizing function of the claimed compounds also addresses the problems associated with toxic effects of known therapeutics. In instances where the known agent is toxic, it is desirable to limit the dosages administered in all cases, and particularly in those cases where drug resistance has increased the requisite dosage. Thus, in some embodiments, when the claimed compounds are co-administered with the known agent, they reduce the dosage required which, in turn, reduces the deleterious effects. Further, because the claimed compounds are themselves both effective and non-toxic in moderate doses, co-administration of proportionally more of these compounds than known toxic therapeutics will achieve the desired effects while minimizing toxic effects.

Figure 11:
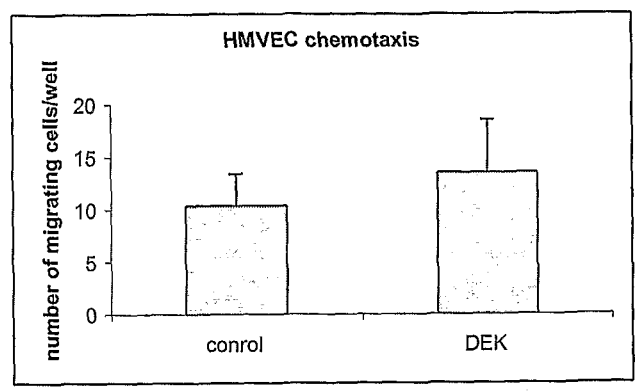
FIG. 11 shows human microvascular endothelial cell (HM-VEC) chemotaxis in response to DEK. Cell migration assay (See, e.g., Koch et al., Arthritis & Rheumatism 44: 31-40, (2001)) was performed with either 3.5 μg of purified, recombinant DEK diluted in PBS, or with just the purification buffer diluted in PBS (control). Nine high-power fields were assayed per sample, and results expressed as the number of cells migrating per well. Error bars show the mean deviation of two separate experiments (*p=0.0249).

Using compositions and methods of the present invention, it was demonstrated that DEK stimulates the chemotaxis of neutrophils (e.g. via its interaction with CXCR2 and CXCR1) (See Example 7). Thus, it was postulated that this interaction was likely mediated by the interaction of DEK's ELR motif with these chemokine receptors, as is the case for the ELR$^+$ chemokines IL-8 and GRO-α. Engagement of these ELR$^+$ chemokines with CXCR1 and CXCR2 is also known to induce chemotaxis of endothelial cells, and thus to be pro-angiogenic (See, e.g., Strieter et al., J Bio Chem 270:27348-27357, (1995)). As angiogenesis is a very important part of inflammatory arthritis, as well as being key to the pathogenesis of several of the malignancies characterized by increased expression of DEK, it was determined whether DEK might be pro-angiogenic, using recombinant DEK in migration assays with Human Microvascular Endothelial Cells (HMVEC). As shown in FIG. 11, DEK attracts endothelial cells, and thus possesses pro-angiogenic potential.

Accordingly, the present invention also provides a method of inhibiting angiogenesis in a subject comprising: a) providing: i) a subject; and ii) an agent (e.g., an anti-DEK antibody or siRNA) that inhibits DEK expression (e.g., nucleic acid and/or protein) and/or DEK activity (e.g., ability to recruit neutrophils, CD 8$^+$ T cells and/or NK cells); and b) administering the agent to the subject such that angiogenesis (e.g., associated with chronic inflammatory disease or autoimmune disease) in the subject is reduced in the presence of the agent compared to in the absence of the agent. The term "reducing" when used in reference to a disease (such as inflammation or autoimmune disease) means diminish, delay, or eliminate (objectively and/or subjectively) the level of one or more undesirable symptoms that are associated with the disease. As used herein, the term "diminishing symptoms" refers to decreasing the levels of one or more symptoms. The term "delaying symptoms" refers to increasing the time period between exposure to an immunogen and the onset of one or more symptoms. The term "eliminating" symptoms refers to completely "reducing" and/or completely "delaying" one or more symptoms.

The present invention further describes cellular secretion of DEK as well as the ability of non-DEK secreting cells to internalize the secreted DEK (See, e.g., Examples 3-5, 10-11). As described herein, secretion of DEK has biological consequences (e.g., acts to attract cells (e.g., neutrophils and/or T cells) to a site (e.g., a site of inflammation)). Thus, the present invention also provides the ability to alter biological activity associated with DEK by inhibiting DEK activity. In some embodiments, an antibody can be used to bind to DEK (e.g., extracellular DEK) thereby inhibiting DEK activity (e.g. the recruitment of cells to a site of inflammation). In some embodiments, DEK expression is inhibited (e.g., as described herein using RNAi) to inhibit DEK activity. In some embodiments, nucleic acid sequences can be utilized (e.g., administered to a subject) to bind to DEK (e.g., extracellular DEK and/or intracellular DEK) thereby inhibiting DEK activity. In some embodiments, a combination of agents (e.g., nucleic acid sequence, antibodies, small molecules and/or other agents (e.g., identified using assays with test compounds described herein) are utilized to inhibit DEK activity (e.g., extracellular activity (e.g., recruitment of cells to a site (e.g., a site of inflammation), or, intracellular activity (e.g., binding to DNA and/or binding to co-factors or other proteins (e.g., ALY)). In some embodiments, altering the biological activity of DEK sensitizes cells to therapeutic treatment (e.g., See Example 15).

EXPERIMENTAL

The following examples are provided in order to demonstrate and further illustrate certain preferred embodiments and aspects of the present invention and are not to be construed as limiting the scope thereof.

Example 1

Materials and Methods

Cell Preparation.

MDM were prepared as described (See, e.g., Lane et al., J Immunol 163, 3653-61. (1999)). Briefly, heparinized venous blood was collected from healthy volunteers, and peripheral blood mononuclear cells (PBMC) were separated by Ficoll-Hypaque (Amersham Pharmacia Biotech AB, Uppsala, Sweden) density gradient centrifugation. MDM were purified by adherence to plastic for 2 h at 37° C. at a concentration of 5×10$^5$/ml. Adherent cells were consistently >90% monocytes (See, e.g., Lane et al., J Immunol 163, 3653-61. (1999)). Adherence-purified human monocytes were cultured in X-Vivo medium supplemented with 40% human AB serum (Bio-Whittaker, Walkersville, Md.) and 100 units of penicillin and 50 units of streptomycin per ml (See, e.g., Punturieri et al., J Exp Med 192, 789-99. (2000)).

Synovial fluids (SF) were previously obtained from the Pediatric Rheumatology Tissue Repository, Cincinnati Children's Hospital Medical Center. They were originally collected from 45 children undergoing therapeutic intra-articular injections for inflammatory arthritis, and from 10 children undergoing diagnostic arthroscopy for presumed non-inflammatory joint pain. SF were diluted (1:1) in phosphate buffered saline (PBS) and centrifuged at 200×g for 30 min to separate cells from the fluid prior to freezing at −70° C. Some fluids were centrifuged through Ficoll at 900×g for 25 minutes. Fluids were stored by the Pediatric Rheumatology Tissue Repository, Cincinnati Children's Hospital Medical Center.

Antibodies.

Rabbit polyclonal antiserum against an N-terminally truncated DEK protein (amino acid 68-375) was kindly provided by Gerard Grosveld (St. Jude Children's Research Hospital, Memphis, Tenn.). Affinity purified, goat polyclonal DEK antibody, raised against a peptide from the carboxy terminus of DEK, was purchased from Santa Cruz (Santa Cruz, Calif.). Monoclonal antibody and goat polyclonal antibody to CD81 were also purchased from Santa Cruz (Santa Cruz, Calif.). A monoclonal antibody (mAb) was raised against the full-length DEK protein, which was overexpressed in Spodoptera frugiperda SF-9 insect cells infected with recombinant baculovirus (Clontech, Palo Alto, Calif.). DEK protein from baculovirus-infected SF-9 cells was isolated using His-Trap columns for purification of histidine-tagged proteins (Amersham Pharmacia Biotech) with further purification by SDS-PAGE and electroelution. Cell fusion, hybridoma cell line development, and ascites production were all performed by the hybridoma core facility at the University of Michigan and the hybridoma development service at the Saint Louis University Health Sciences Center. CD56-PE, CD19-FITC, CD4-FITC, CD8-PE and mouse IgG1 isotype control antibodies for flow cytometry were purchased from BD Pharmingen (San Diego, Calif.).

Immunohistochemistry.

Human monocytes and MDM were cultured using a glass chamber slide system (Nalge Nunc International, Naperville, Ill.). Cells were washed with PBS and fixed for 10 min at 4° C. with PBS containing 4% paraformaldehyde. Cells were washed with PBS, and nonspecific binding sites were blocked by incubation for 1 h with 0.2% BSA in PBS. Slides were incubated with polyclonal anti-DEK antibody diluted 1:100 in PBS with 0.1% saponin (to permeabilize cells) for 1 h.

Slides were washed thoroughly with 0.1% saponin in PBS, and were blocked a second time by incubation with normal goat serum for 1 h, then washed and incubated with 10 µg/ml ALEXA FLUOR 488 conjugated to goat anti-rabbit antibody (Molecular Probes, Eugene, Oreg.). The slides were washed with distilled water, dried, and mounted with SlowFade Antifade Kit (Molecular Probes). Fluorescence was viewed with a Leitz Orthoplan microscope or Bio-Rad MRC-600 laser scanning confocal microscope. Photographs were taken with a Sony DKC5000 3CCD RGB camera.

For live imaging of DEK-GFP, MDM were washed and maintained in serum-free media during and after transfection. Cells were maintained at 37° C. during image collection by Olympus IMT-2 inverted light microscope beginning sixteen hours following transfection with lipofectamine 2000 (Invitrogen, Carlsbad, Calif.).

GFP Constructs.

Primers with EcoRV (5') and EcoRI (3') sites were designed for PCR-based subcloning of specific segments of the dek coding region. Products were cloned into pGEMT Easy, excised with EcoRV and EcoRI, and ligated into pGNVL3 mammalian GFP vector (gift of T. Glaser, University of Michigan).

Western Blots.

MDMs were maintained for 12 h in serum-free conditioned media with added dexamethasone, (0.5 µM or 1 µM) (Sigma St. Louis, Mo.), cyclosporin A (CsA, 1 µg/ml) (Sigma St. Louis, Mo.), carbonyl cyanide chlorophenyl hydrazone (CCCP) (10 µM) (Sigma St. Louis, Mo.), IL-8 (10 ng/ml) (R&D Systems, Minneapolis, Minn.) or TBB (See, e.g., Sarno et al., Pharmacol Ther 93, 159-68 (2002)) for 3 hours. Following 3 washes with PBS, serum-free media was added for 3 to 12 h before harvest. The viability of the cells incubated in serum-free medium with or without added drugs was >95% at 48 h as measured by MTT-based colorimetric assay (Boehringer Mannheim, Indianapolis, Ind.) and by LDH release as previously described (See, e.g., Punturieri et al., J Exp Med 192, 789-99. (2000)). Supernatants were collected and centrifuged for 20 min at 200×g to remove cell debris, then concentrated by a centrifugal filter device (Millipore) in the presence of a protease inhibitor cocktail (Boehringer Mannheim, Indianapolis, Ind.). Equal amounts of protein (20 µg) were loaded under reducing conditions and proteins were separated by 10% SDS-PAGE. The proteins were subsequently transferred to nitrocellulose and probed with mouse monoclonal anti-DEK or rabbit or goat polyclonal anti-DEK antibodies. The bound primary antibody was then detected with horseradish peroxidase-conjugated goat anti-mouse or anti-rabbit secondary antibody using the Super Signal West Pico system (Pierce Chemical Co, Rockford, Ill.).

Isolation of Exosomes.

Exosomes were isolated by differential centrifugation as described (See, e.g., Escola et al., J Biol Chem 273, 20121-7. (1998)). Fourteen day MDM were washed and incubated in serum-free media for 48 h, and supernatant (12 ml) from $2.5\times10^7$ cells was collected and centrifuged for 10 min at 200×g. The supernatant was removed, re-centrifuged for 10 min at 500×g, and was then sequentially centrifuged at 2,000×g for 30 min, 10,000×g for 30 min using an SS-34 rotor (Sorvall), and 70,000×g for 60 min using a TY-65 rotor (Beckman Instruments, Inc., Fullerton, Calif.). All pellet fractions were solubilized under reducing conditions using standard SDS-PAGE loading buffer, and then incubated for 5 min at 95° C. The samples from each pellet and the final supernatant were analyzed by SDS-PAGE and Western blotting.

Proteinase K Protection Assay.

The 70,000×g exosome fraction was divided into three 35 µl aliquots, and then was either left untreated or treated with 200 ng proteinase K (Boehringer Mannheim/Roche, Indianapolis, Ind.) in the presence or absence of Triton X-100. The samples were incubated for 3 hours at 37° C. and the reaction was terminated with PMSF (5 mM final concentration). Immediately after addition of PMSF, SDS loading buffer was added and the sample was heated at 95° C. for 5 min and analyzed by SDS-PAGE and Western blotting (See, e.g., Al-Qahtani et al., Biochem J 331 (Pt 2), 521-9 (1998); Fevrier et al., Proc Natl Acad Sci USA 101, 9683-8 (2004)).

Preparation of Anti-CD81 Antibody-Labeled Magnetic Beads.

Dynabeads M-500 (Dynal, Lake Success, N.Y.) coated with anti-CD81 antibody were used to isolate exosomes as described (See, e.g., Sexton and Cenedella, Biochem Biophys Res Commun 295, 1027-31 (2002)). As recommended by the manufacturer, Dynabeads (supplied in suspension at $4\times10^8$ beads/ml) were incubated overnight in 0.1 M borate (pH 9.5) with unconjugated mouse IgG1 anti-goat linker antibody (Sigma, Saint Louis, Mo.) at a concentration of 10 µg antibody/$2\times10^7$ beads. For this and all subsequent steps, beads were isolated using the MPC magnetic device provided by the manufacturer. Beads were washed thoroughly with PBS, pH 7.4 containing 0.1% (w/v) BSA (PBS/BSA) followed by a 24 h incubation in 0.2 M Tris, pH 8.5, 0.1% (w/v) BSA, with rotation at 4° C. to block remaining free tosyl groups on the surface of the beads. Linker-coated Dynabeads were then incubated overnight at 4° C. with goat anti-CD81 antibody (Santa Cruz Biotechnology, Inc., Santa Cruz, Calif.) at a concentration of 10 µg/$1\times10^7$ beads, after which beads were again washed thoroughly with PBS/BSA. Purified 70,000×g exosome fraction was added to coated beads (100 µg protein per $1\times10^7$ coated beads) in Dynal buffer A (PBS, pH 7.4, 2 mM EDTA, 5% BSA) and incubated overnight at 4° C. with rotation. After thorough washing in PBS, beads were isolated, and purified proteins were solubilized in SDS sample buffer for subsequent analysis by Western blot.

ELISA.

Serum samples from healthy volunteers or JRA patients were diluted 1:50 in dilution buffer (1×PBS with 0.05% Tween-20 and 2% FBS). Synovial fluids from JRA patients or patients undergoing arthroscopic surgery were diluted 1:200 with PBS and dilution buffer. Patient sera were obtained at the Children's Hospital Medical Center, Cincinnati, Ohio. Synovial fluids were obtained at the Children's Hospital Medical Center, Cincinnati, Ohio and at the University of Michigan. The wells of microtiter plates were coated with samples (50 µl) overnight at 4° C., followed by three washes with 1×PBS+ 0.1% Tween-20, and two washes with PBS alone. Plates were blocked with 100 µl/well of 1×PBS+2% bovine serum albumin overnight at 4° C. or at 20° C. for 3-4 hr, followed by five washes as above. Anti-DEK monoclonal antibody (BD Bioscience, San Diego, Calif.) (100 µl/well) was added at a dilution of 1:3200 in dilution buffer for one hour at 20° C., followed by five washes as above. Goat anti-mouse biotinylated secondary antibody (BD Bioscience, San Diego, Calif.) at $1:1\times10^4$ in dilution buffer was added (100 µl/well) for one hour at 20° C., again followed by five washes. Streptavidin (1:300 dilution in dilution buffer) (100 µl/well) was added for 35 min at 20° C., followed by five washes. TMB substrate (100 µl/well) was added to develop the plate for 5-15 minutes prior to stopping the reaction by addition of 1 N $H_2SO_4$ (50 µl/well). Optical density was read within 20 minutes at 450 nm. A standard curve was generated from full length recombinant DEK protein overexpressed in *Spodoptera frugiperda*

SF-9 insect cells infected with recombinant DEK, and isolated over His-trap nickel-chelating columns (Pharmacia/Pfizer, New York, N.Y.) for histidine-tagged proteins.

In Vitro Migration Assay.

White blood cells were isolated from venous blood from healthy donors as described above, and were depleted of monocytes by adherence to plastic for 2 h as described in the Cell Preparation section. Monocyte-depleted white blood cells ($1\times10^6$ cells/ml) were fluorescently labeled with 20 μM of 2',7'-bis-(2-carboxyethyl)-5-carboxyfluorescein acetoxymethyl (BCECF AM, Molecular Probes, Eugene, Oreg.) according to the manufacturer's directions. The cells were washed and resuspended at $1\times10^6$ cells/ml in serum-free RPMI medium, and $1\times10^5$ labeled cells in 100 μl were added to the upper chamber of a 24-well Transwell chemotaxis insert with pore size of 3 μm or 5 μm (Corning, N.Y.). The lower chambers contained serum-free RPMI medium alone, recombinant DEK made in baculovirus, or a deletion mutant of the β form of human GLI-2 (See, e.g., Smith et al., J Virol 75, 2301-13 (2001)) produced in baculovirus as the control protein. After 30 min to 1 h, the number of fluorescently labeled migrating cells in the lower chamber was determined at 485 nM/535 μM wavelength using a Tecan GENios plate-reader (Phenix, Austria). The results were expressed as the average fold increase of the number of cells migrating toward lower chambers containing DEK divided by the number of cells migrating toward the control wells (medium alone).

Neutrophil Purification.

Forty ml of venous blood was collected from healthy volunteers into a 50 ml sterile syringe containing a mixture of 7 ml 0.25 M Citrate (0.17 M NA Citrate and 0.083 M Citric Acid) and 6% Dextran in PBS buffer. The blood was incubated for 30 min at room temperature and the upper phase was collected and further separated by Ficoll as described above. The neutrophil fraction was collected and washed with HBSS buffer and then pelleted again. The remaining red blood cells were further lysed in 9 ml cold distilled water for 30 sec and the reaction was stopped by 1 ml of cold 10×PBS buffer. Cells were washed again with HBSS and resuspended in RPMI 1640 as described above for the migration assay.

Flow Cytometry.

Cells migrating to the lower chambers ($\sim10^6$) collected from a 5 μm pore size transwell chemotaxis insert were transferred into a FACS tube. Cells were washed three times with FACS buffer (DPBS, 3% FBS and 0.09% $NaN_3$), then incubated on ice with antibodies in 100 μl of FACS buffer for 60 min, wrapped to protect them from light. Cells were washed again three times in FACS buffer, fixed in 1 ml of 1% PFA/PBS overnight at 4° C., and washed three times with FACS buffer and analyzed by EPICS XL Flow Cytometer System II software (Coulter, Miami, Fla.).

FAS-L Induced Apoptosis Assays.

Jurkat cells were washed with serum-free RPMI medium and incubated with 3% FAS-L without or with the broad-spectrum caspase inhibitor zVAD for 180 min. Cells were fractionated and the cytoplasm was separated by SDS-PAGE followed by immunoblotting with DEK specific antibodies (mouse monoclonal, BD Bioscience). As a loading control the same blot was reprobed with specific antibodies to beta-actin.

Time Course of Caspase 3/7 Activation and Chromatin Condensation in Fas-L (CD95 L)-Treated Jurkat Cells.

Jurkat cells were washed with serum-free RPMI medium and incubated with 3% FAS-L without or with the broad-spectrum caspase inhibitor zVAD for the indicated time points. Caspase activation was detected using the bisubstituted caspase-3 target sequence: aspartate-glutamate-valine-aspartate, (z-DEVD)2 peptide derivative of the fluorophore cresyl violet. For scoring of chromatin condensation cells were stained with Hoechst and investigated by fluorescence microscopy.

In Vivo Pulse Labeling of Apoptosing Jurkat Cells.

Jurkat cells were washed with serum-free RPMI medium and incubated for the indicated time points with 200 mCi 32Pi (carrier free; ICN) in the absence or presence of 3% Fas-L. Cells were harvested and subjected to cell fractionation. In the upper panels the extracts were analyzed for the presence of DEK and PARP (poly ADP ribose polymerase) as input control. Ongoing apoptosis is indicated by cleavage of PARP. The cytosol/nucleosol and the chromatin-bound fraction of the individual samples were subjected to immunoprecipitation with DEK-specific antibodies (rabbit polyclonal, affinity purified). The resulting immunocomplexes were separated by SDS-PAGE and analyzed by autoradiography (32P) and immunoblotting with DEK-specific antibodies (mouse monoclonal, BD Bioscience).

ADP-Ribosylation of DEK In Vitro.

Increasing amounts of recombinant His-DEK (100, 200, 500 ng) were incubated with recombinant PARP, ADP and EcoRI linker for 15 min at 37° C. The reaction was stopped by addition of SDS-containing loading buffer. Individual samples were separated by SDS-PAGE and analyzed by immunoblotting with DEK-specific antibodies (rabbit polyclonal, affinity purified). The same blot was subsequently incubated with mouse monoclonal DEK-specific antibodies. As a negative control, 500 ng of recombinant HIS-DEK was treated as above but without addition of PARP.

Aggregation assay with ADP-ribosylated DEK. Recombinant HIS-DEK (25, 50, 100, 200, 400 ng) was used either untreated (HIS-DEK) or in its ADP-ribosylated form.

Topology assay with ADP-ribosylated DEK. Recombinant HIS-DEK was used either untreated (HIS-DEK) or in the ADP-ribosylated form.

ALY-DEK Interaction.

GST-pull down. 10 ml of 35S-labeled in vitro translated DEK protein was incubated with GST vector protein or GST-ALY coated glutathione agarose beads for 1 hour at room temperature. After extensive wash, the retained in vitro translated proteins were separated on SDS-PAGE gel and visualized by autoradiography.

Aggregation Assay.

One ng of a radiolabeled equimolar mixture of MAR (MII) and non-MAR DNA pUC18) was incubated in the absence or presence of either 200 ng BSA, 200 ng GST, or 25, 50 or 100 ng of HIS-DEK or GST-ALY or with 25 ng of HIS-DEK and 25, 50, or 100 ng GST-ALY. Lane 1 is without protein. After incubation in reaction buffer for 30 min in a total volume of 30 ml, the individual samples were pelleted for 15 min at 14,000 rpm. The pellet was resolved in SDS-containing loading buffer and separation of samples was performed by agarose gel electrophoresis followed by analysis using autoradiography. The position of MAR (MII) and pUC18 DNA is indicated.

EMSA with Purified HIS-DEK and GST-ALY.

175 ng (0.05 pmol) of SV-40 DNA (5243 bp) was incubated with 2, 5, or 10 pmol dephosphorylated HIS-DEK or GST-ALY respectively, or without protein for one hour at 37° C. HIS-DEK (2 pmol, 5 pmol, and 10 pmol) was incubated with increasing amounts of GST-ALY (2, 5 and 10 pmol). As a control, GST (2, 5 and 10 pmol) alone, or together with either 2 pmols of HIS-DEK or 2 pmol GST-ALY were incubated in the same way. The nucleoprotein complexes were separated on a 0.6% agarose gel for 16 h at 2V/cm in 0.5×TBE and analyzed by ethidium bromide staining.

Topology Assay with his-DEK and GST-ALY.

10 ng (0.003 pmol) of circular SV-40 DNA was incubated with 2, 4 or 8 pmol of HIS-DEK (DEK) or GST-ALY (ALY) or either 2 or 4 pmol HIS-DEK and 2, 4 or 8 pmol GST-ALY in the presence of 1 U topoisomerase I. As a control for the functionality of topoisomerase I, SV-40 DNA was incubated either with or without topo I in the absence of GST-ALY and DEK. After 1 h at 37° C., the samples were treated with Proteinase K, and the DNA was purified and analyzed by agarose gel electrophoresis (0.8% at 2V/cm) and SybrGold staining.

Lentiviral shRNA-Mediated Knockdown of DEK.

Two shRNA-delivering lentiviral vectors were created to knockdown DEK expression. An shRNA targeting a sequence in the 3' UTR of DEK was inserted downstream of an H1 promoter. A second vector was created by the addition of a murine U6 promoter and a second shRNA targeting a sequence in the coding region of DEK. HeLa S3 cells were transduced with either an empty vector, a vector containing one shRNA, or a vector containing both shRNAs. Knockdown was determined by western blotting and detected by affinity-purified polyclonal anti-DEK antibodies.

Micrococcal Nuclease Analysis.

Control HeLa cells (stably-transfected with empty lentivirus) and DEK knock-down HeLa cells (stably-transfected with a double DEK shRNA lentivirus) were harvested and the nuclei purified. The suspension was adjusted to 500 mg DNA/ml and supplemented with 2 mM CaCl2. The samples were incubated at 14° C. for 10 min. 10 U of MNase was added per 50 mg of DNA and incubated for the indicated time points. Reaction was stopped by addition of 8 mM EDTA and incubation on ice. Released chromatin was separated from insoluble material by centrifugation and analyzed by agarose gel electrophoresis and staining by ethidium bromide.

Samples were analyzed fluorimetrically for their DNA content. Values were expressed as the ratio of released DNA versus insoluble DNA in comparison to the starting material.

Immunofluorescence Microscopy of Control and DEK Knock-Down HeLa Cells.

HeLa cells were fixed with paraformaldehyde and incubated with Histone H3 K9 trimethylated specific antibodies (a marker for transcriptionally inactive heterochromatin). DNA was visualized by DAPI staining.

DEK Knock-Down and DNA Damage Assays.

Jurkat and HeLa S3 cells were transduced with either an empty lentiviral vector, or a vector containing two DEK-specific shRNAs. Control and DEK-knockdown Jurkat cells were exposed to increasing doses of UVC radiation. Twenty-four hours after irradiation, the percentage of apoptotic cells was determined by staining with Annexin-V and analysis by flow cytometry. HeLa S3 control and DEK-knockdown cells were similarly treated with increasing doses of UVC radiation. Cells were fixed, permeabilized, and stained with R-phycoerythrin labeled antibodies against the active form of caspase-3 twenty-four hours after irradiation. The percentage of cells expressing the active form of caspase-3 was determined by flow cytometry. Jurkat control and DEK-knockdown transduced cells were treated with either etoposide or cisplatin at increasing doses and 24 hours later the percentage of apoptotic cells was determined by staining with Annexin-V.

Example 2

DEK is Present in the Cytoplasm of MDM

DEK has previously been considered to be an exclusively nuclear protein (See, e.g., Fu and Markovitz, J Biol Chem 271, 19599-605. (1996); Fu et al., Proc Natl Acad Sci USA 94, 1811-5. (1997); Adams et al., Arthritis Res Ther 5, R226-33 (2003); Alexiadis et al., Genes Dev 14, 1308-12. (2000); Waldmann et al., J Biol Chem 277, 24988-94 (2002); von Lindern et al., Mol Cell Biol 12, 1687-97 (1992); von Lindern et al., Genes Chromosomes Cancer 5, 227-34 (1992); von Lindern et al., Baillieres Clin Haematol 5, 857-79 (1992); Fornerod et al., Oncogene 10, 1739-48 (1995)). Initially, DEK's subnuclear localization was determined by immunofluorescence and confocal microscopy. For this purpose, the well-characterized model of monocyte-derived macrophages (MDM) was employed in which human monocytes differentiate into macrophages with incubation in 40% human serum. The MDM produced in this way are large and multinucleated; in addition, they display a phenotype similar to that of macrophages exposed to inflammatory stimuli, acquiring a number of functional properties such as increased phagocytic and secretory activity. After seven to ten days of serum-induced differentiation, MDM secrete large amounts of tissue-destructive cathepsin proteinases and develop the ability to degrade elastin (See, e.g., Reddy et al., Proc Natl Acad Sci USA 92, 3849-53. (1995); Punturieri et al., J Exp Med 192, 789-99. (2000)).

Using immunofluorescence staining, the subcellular distribution of DEK in monocytes was observed to be exclusively nuclear on day 1 (See FIG. 1A, panel a), as previously described (See, e.g., Fornerod et al., Oncogene 10, 1739-48 (1995)). However, with serum-induced differentiation, a progressive disappearance of DEK from the nuclei and a time-dependent increase in DEK's presence throughout the cytoplasm was noted at days 3, 5 and 12 (See FIG. 1A, panels a, c, and e). DEK's cytoplasmic location was further confirmed by using an enhanced green fluorescent protein hybrid construct (DEK-EGFP) in transiently transfected MDM. Live cell microscopy images of selected cells shown in FIG. 1B (panels a, c, and e) demonstrate the distribution of DEK-EGFP in 13 day MDM as primarily nuclear, but they also reveal DEK in peri-nuclear, cytoplasmic and membrane locations.

Example 3

DEK is Secreted by MDM, a Process Dependent on Protein Kinase CK2

Figure 2:
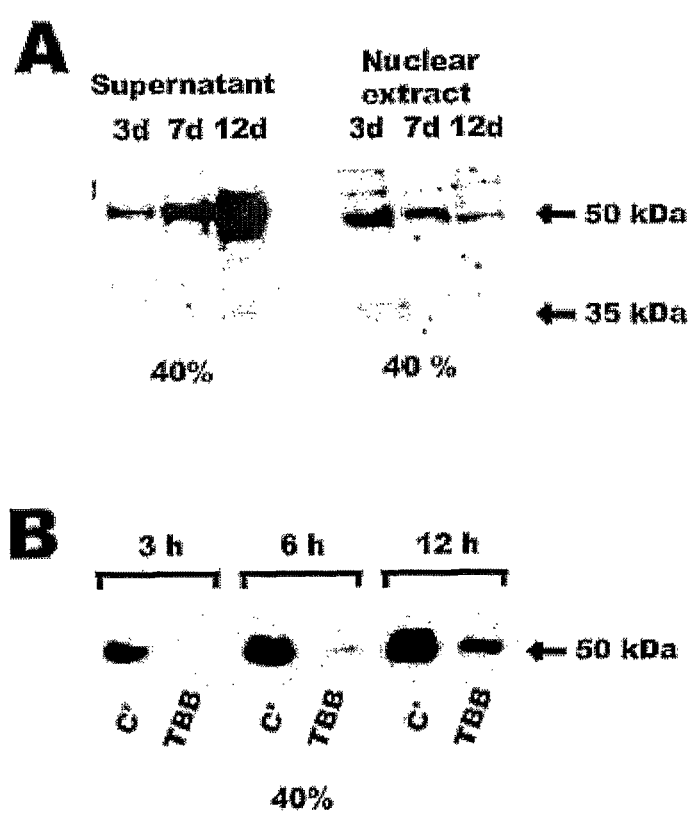
FIG. 2 shows DEK is secreted in a CK2-dependent manner as monocytes differentiate into MDM. Monocytes incubated in 40% human serum for 3, 7 and 12 days were washed and maintained in serum-free medium for 12 h prior to collection of cell supernatants. A total of 30 µg of protein was subjected to Western blot analysis using anti-DEK monoclonal antibody. Arrows in A and B indicate the 50 and 35 kDa forms of DEK. (A) Supernatants (left panel) and nuclear extracts (right panel). (B) Day 8 MDM treated with 50 µM of the highly-specific CK2 blocker TBB or with DMSO control for 3 h were washed and maintained in serum-free media for the indicated time. Supernatants were collected and analyzed by Western blot.
Figure 3:
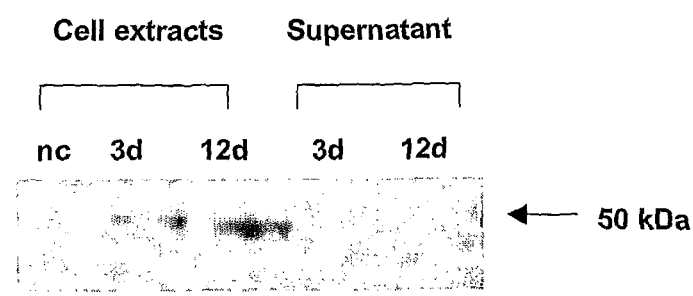
FIG. 3 shows FLAG-tagged DEK is found in supernatants of MDM infected with DEK-encoding adenovirus. Day 3 and day 12 MDM incubated in 40% human serum were infected with replication-incompetent DEK-encoding adenovirus at >100 MOI. Cells were washed after 12 h and maintained in serum-free media for another 24 h before collection of supernatants. FLAG-tagged DEK was immunoprecipitated from supernatants and total cell extracts from day 3 or day 12 MDM using the FLAG-tag immunoprecipitation kit. FLAG-tagged DEK was detected by Western blot analysis using polyclonal anti-DEK antibody. The first lane shows immunoprecipitation results from uninfected cells, using anti-FLAG-tag antibodies as a negative control.

Because serum-differentiated inflammatory MDM secrete a variety of proteins (See, e.g., Reddy et al., Proc Natl Acad Sci USA 92, 3849-53. (1995); Punturieri et al., J Exp Med 192, 789-99. (2000)) it was determined whether DEK's disappearance from the nucleus and movement into the cytoplasm was followed by its secretion. Cell-free supernatants from day 3 to day 12 MDM were analyzed for the presence of extracellular DEK. Starting at day 3 and continuing through day 12 as monocytes differentiated into MDM, it was possible to identify increasing amounts of the 50 kDa and 35 kDa forms of DEK (See, e.g., Sierakowska et al., Clin Exp Immunol 94, 435-9 (1993)) in cell-free supernatants by Western blot analysis using a DEK-specific monoclonal antibody (See FIG. 2A, left panel). A corresponding reduction of the amount of nuclear DEK was detected in the same time frame (See FIG. 2A, right panel). Overall, the presence of extracellular DEK in the supernatants of differentiated MDM was demonstrated using three separate monoclonal and three separate polyclonal antibodies to DEK. Secretion was further verified by infecting day 12 cells with a recombinant adenoviral vector expressing FLAG-tagged DEK. DEK was again detected in the supernatant by Western blot analysis using anti-FLAG-tag antibody (See FIG. 3).

Although macrophages are known to be resistant to many apoptotic stimuli, it was verified that the presence of DEK in the supernatants of activated MDM was not a consequence of cell damage or demise. Four different methods were used to confirm that DEK is secreted, rather than simply leaked, into the extracellular compartment. First, using measurements of extracellular LDH and other indicators (See, e.g., Reddy et al., Proc Natl Acad Sci USA 92, 3849-53. (1995); Punturieri et al., J Exp Med 192, 789-99. (2000)), unaltered cell viability and a lack of cellular necrosis or apoptosis through day 12 and beyond has been demonstrated in this model. Second, the cell viability of 12 day MDM was examined by MTT assay after 12, 24, and 48 hours in serum-free medium, and found no decline in viability over this period (See Table 1, below, showing the cell viability of day

| MTT assay(absorbance $A_{570}$-$A_{650}$ ± SD) | |
|---|---|
| Control | 1.19 ± 0.37 |
| 12 h | 1.12 ± 0.25 |
| 24 h | 1.00 ± 0.26 |
| 48 h | 1.31 ± 0.29 |

12 MDM assayed by MTT-based colorimetric assay after 12, 24, and 48 hours in serum-free medium, compared to day 12 MDM in serum-containing medium (control)).

As a third method for verifying that DEK is not released into the extracellular compartment by damaged or dying cells in this model, MDM supernatants were also analyzed for the presence of the high mobility group B-1 (HMGB-1) protein. HMGB-1 is a nuclear protein that is released from necrotic cells or by monocytes in response to lipopolysaccharide, IL-1 or TNF-α (See, e.g., Bonaldi et al., Embo J 22, 5551-60 (2003); Wang et al., Science 285, 248-51. (1999)). Under serum-free cell culture conditions, Western blot analysis of the supernatants showed no evidence of HMGB-1. Further, treatment of MDM with the proapoptotic energy blocker carbonyl cyanide chlorophenylhydrazone (CCCP) actively blocks DEK secretion (See FIG. 7A). Finally, complete inhibition of DEK secretion was demonstrated when 12-day MDM were treated with 4,5,6,7-tetrabromobenzotriazole (TBB), a specific inhibitor of CK2 that is also proapoptotic (See, e.g., Loizou et al., Cell 117, 17-28 (2004); Sarno et al., FEBS Lett 496, 44-8 (2001); Sarno et al., J Biol Chem 277, 22509-14 (2002)). CK2 is the primary kinase involved in DEK phosphorylation (See, e.g., Kappes et al., Mol Cell Biol 24, 6011-20 (2004)). After a three-hour treatment of 8-day MDM with TBB, DEK was noted to be absent in supernatants collected during the first 3 hours of incubation in serum free media (See FIG. 2B). Beginning six hours after removal of TBB, its inhibitory effect gradually declines. Even 12 hours after removal of TBB, however, the amount of extracellular DEK from TBB-treated cells is still significantly lower than that from untreated cells, indicating that DEK is actively secreted by viable MDM, and that this secretion requires CK2-mediated phosphorylation.

Example 4

DEK is Secreted Via Exosomes

Like several other secreted mammalian proteins, including IL-1α and IL-1β, basic fibroblast growth factor, and HMGB-1 (See, e.g., Bonaldi et al., Embo J 22, 5551-60 (2003); Mehul et al., J Cell Sci 110, 1169-78. (1997)), DEK lacks an identifiable signal sequence. Furthermore, DEK does not appear to utilize the classical Golgi pathway for secretion (e.g., as observed via treatment of MDM with Golgi inhibitors such as Brefeldin A and monensin that does not alter the amount of DEK found in culture supernatants, in contrast to the Golgi-dependent secretion of vimentin by MDM, See, e.g., Mor-Vaknin et al., Nat Cell Biol 5, 59-63 (2003)). Although secretion through the Golgi apparatus traditionally requires proteins to be glycosylated and DEK does have several potential glycosylation sites, DEK secretion was not inhibited by treatment of MDM with tunicamycin (which inhibits N-glycosylation). Treatment of DEK protein with PNGase F (which enzymatically removes the N-linked oligosaccharides), or with NaNase II or O-glycosidase DS (which enzymatically remove all Ser/Thr linked Gal (b1,3) GalNAc(a1)) also failed to demonstrate glycosylation of DEK.

As a critical component of their biological function, macrophages and other cells of the hematopoietic lineage use secretory lysosomes or prelysosomal multivesicular compartments to deliver proteins to the plasma membrane (See, e.g., Punturieri et al., J Exp Med 192, 789-99. (2000); Stinchcombe and Griffiths, J Cell Biol 147, 1-6. (1999)). Internal and membrane proteins are released from multivesicular compartments into the extracellular environment in small membrane vesicles called exosomes, the product of fusion of multivesicular late endosomes with the plasma membrane (See, e.g., Thery et al., J Immunol 166, 7309-18. (2001)). In order to determine if DEK is secreted in this manner, the exosomal fraction was isolated from the supernatants of day 13-15 MDM by serial centrifugation (See, e.g., Raposo et al., J Exp Med 183, 1161-72. (1996); Escola et al., J Biol Chem 273, 20121-7. (1998)), and the presence or absence of DEK determined. As shown in FIG. 3A, following 70,000×g centrifugation DEK is found in the pellet, the fraction known to be highly enriched in exosomes (See, e.g., Raposo et al., J Exp Med 183, 1161-72. (1996) Escola et al., J Biol Chem 273, 20121-7. (1998)). DEK is detected in this fraction in its 50 kDa and 35 kDa forms, running slightly higher than intracellular DEK (FIG. 4A, cell extract), probably due to differences in phosphorylation state. Intracellular DEK itself can be detected in multiple forms, especially in primary cells (See FIG. 2A), likely due to heavy posttranslational phosphorylation, acetylation, and dimerization (See, e.g., Fu and Markovitz, J Biol Chem 271, 19599-605. (1996); Fu et al., Proc Natl Acad Sci USA 94, 1811-5. (1997); Kappes et al., Mol Cell Biol 24, 6011-20 (2004); Kappes et al., Mol Cell Biol 24, 6000-10 (2004); Waldmann et al., Gene 343, 1-9 (2004); Cleary et al., J Biol Chem 280, 31760-7 (2005)), and often runs at 43-45 kDa (See, e.g., Fu and Markovitz, J Biol Chem 271, 19599-605. (1996); Fu et al., Proc Natl Acad Sci USA 94, 1811-5. (1997)).

Figure 4:
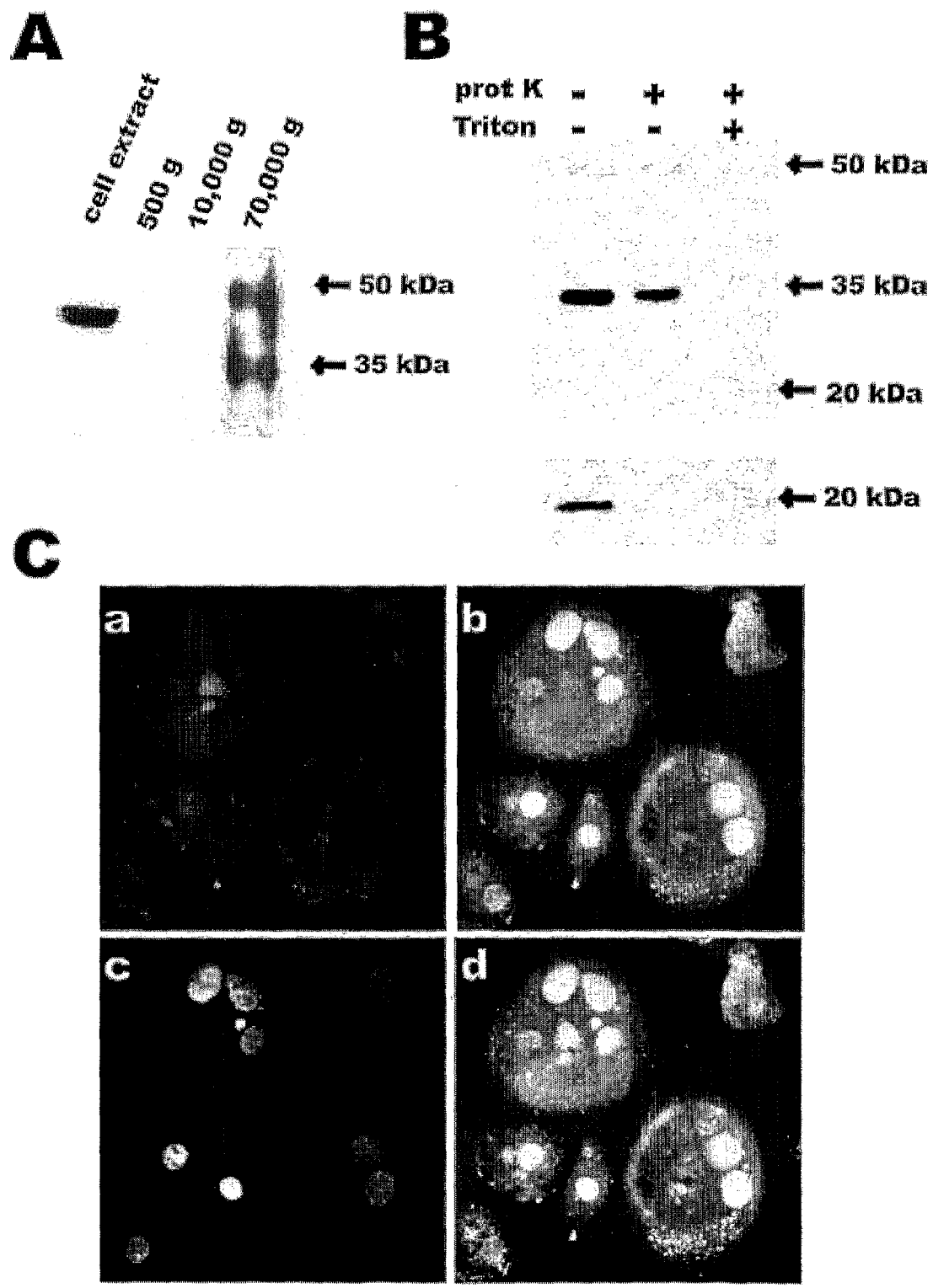
FIG. 4 shows DEK is secreted in exosomes from differentiated MDM. Human peripheral blood monocytes were isolated and maintained in 40% serum for 15 days. (A). Western blot analysis of exosomes in supernatants from day 15 MDM. Supernatants from day 15 serum-activated MDM were centrifuged at 500×g, 10,000×g and 70,000×g as described in the Experimental section. The pellets from specific fractions were solubilized in sample buffer for Western blot analysis. (B). The 70,000×g fraction was used in a proteinase K protection assay. The sample in lane 1 was untreated, that in lane 2 was treated with proteinase K alone, and that in lane 3 was treated with proteinase K and Triton X. Samples were analyzed for the presence of DEK (upper panel) and CD81 (lower panel) under reducing conditions by Western blot analysis, using specific goat polyclonal anti-DEK antibody or anti-CD81 antiserum. DEK is detected at 50 kDa and 35 kDa, and CD81 at 20 kDa. (C). Colocalization of DEK and the exosomal marker CD81 by confocal microscopy. Day 13 MDM cultured in glass chamber slides were incubated with mouse anti-CD81 antibody and stained with an Alexa Fluor-conjugated rabbit anti-mouse antibody to detect CD81 panel a), or incubated with goat polyclonal DEK antiserum and stained with a FITC-conjugated rabbit anti-goat antibody to detect DEK (panel b). Colocalization of DEK and CD81 (shown in yellow) was detected in vesicular structures throughout the cells (panel d). Cell nuclei were stained with DAPI (blue) (panel c). (Magnification 60×).
Figure 5:
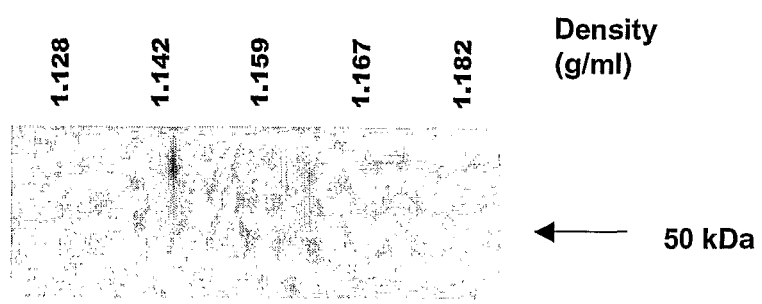
FIG. 5 depicts a sucrose gradient showing that DEK is secreted in exosomes from differentiated MDM. Cells were incubated for 48 h in serum-free media prior to collection of culture supernatants. The enriched exosomal (70,000×g) fraction from serial centrifugation of day 15 serum-differentiated MDM supernatant was floated onto a linear sucrose gradient. The indicated gradient fractions were collected and analyzed for the presence of DEK under reducing conditions by Western blot analysis using polyclonal DEK antiserum.

When the 70,000×g fraction was layered onto a linear sucrose density gradient, DEK was found in fractions corresponding to densities of 1.142 g/ml and 1.159 g/ml (See FIG. 5), the exosome-containing fractions (See, e.g., Raposo et al., J Exp Med 183, 1161-72. (1996)). A proteinase K (PK) protection assay was subsequently performed to determine whether DEK is located on the surface of the exosome or within it. As shown in FIG. 4B, DEK from the 70,000×g fraction was protected from digestion by PK (See FIG. 4B, top panel), whereas the surface membrane protein CD81, known to be on the exosome membrane, was completely digested (See FIG. 4B, bottom panel). When the exosomes were permeabilized with a detergent, however, DEK was completely degraded by PK, indicating that DEK is located inside the exosome and is not on the surface membrane. Well-defined vesicular structures were also observed in the cytoplasm of day 13 MDM that had been immunohistochemically stained with polyclonal DEK antibody (See FIG. 4C, panel b), further suggesting that DEK movement into the extracellular space may occur via secretory vesicles. No chromosomal material was detected in these structures, differentiating them from the nuclei (See FIG. 4C, panel c). In addition, immunofluorescence staining revealed that DEK and CD81 colocalized to these vesicular structures (See FIG. 3C, panel d), suggesting that these structures may represent secretory vesicle exosomal precursors. Although the 35 kDa form of DEK appears to be the predominant form in the exosomal fraction, the 50 kDa DEK species has also been observed (See FIG. 4B). As the 50 kDa form of DEK is dominant in the supernatants of activated MDM (See FIG. 2A), a separate non-classical secretion pathway may exist for this form of DEK.

Example 5

DEK Protein is Present in Synovial Fluids and Sera from JRA Patients

The predominance of macrophages and macrophage-like synoviocytes in inflamed joints provides an experimental model of serum-differentiated monocyte-derived macrophages appropriate for studying the role of DEK in juvenile arthritis. Several clinical studies have shown that approximately 40-60% of all JRA patients have circulating antibodies to DEK and other nuclear proteins, and that DEK reactivity is present in a much higher proportion of children with pauciarticular onset JRA, and is nearly omnipresent in children with JRA-associated iridocyclitis (See, e.g., Szer et al., J Rheumatol 21, 2136-42 (1994); Murray et al., J Rheumatol 24, 560-7 (1997); Sierakowska et al., Clin Exp Immunol 94, 435-9 (1993)). The observation that DEK is secreted by serum-differentiated MDM made during the development of the present invention suggested a possible mechanism by which DEK might be secreted by inflammatory cells within the inflamed joint compartment, and thereby provokes immune reactivity. Thus, in order to determine if DEK is secreted into the joint space of subjects (e.g., children) with active inflammatory arthritis, monoclonal anti-DEK antibodies were used to probe Western blots of synovial fluids from a childhood arthritis tissue repository. As shown in FIG. 6A, a DEK-specific monoclonal antibody identified a strong DEK band in synovial fluid samples from 36 of 45 juvenile arthritis patients (See FIG. 6A, lanes 2 and 3), whereas low levels of DEK were seen in the thick, clear, non-inflammatory joint fluid aspirated from a Baker's cyst in a patient whose polyarticular juvenile arthritis was in remission (See FIG. 6A, lane 1). Low levels of DEK (or no DEK) were detected in 3 of 10 synovial fluid samples from children undergoing arthroscopic surgery for presumed non-inflammatory causes of joint effusion. Statistical analysis proved the difference in detectable synovial fluid DEK (36/45 vs 3/10) to be highly significant (p<0.003 by Fisher's exact test). A DEK antigen ELISA also confirmed this result. Thus, the present invention demonstrates that DEK exists in synovial fluid from JRA patients, thereby indicating that DEK is present in inflammatory joint effusions.

To further establish the clinical relevance of this observation, macrophages were purified from the synovial fluid of a patient with active, anti-nuclear antibody-positive JRA and placed in culture for 12 days. Exosomes were purified from the cell supernatant using magnetic beads coated with antibodies to the CD81 exosomal marker, and the recovered fraction was examined by Western blot for reactivity with polyclonal DEK antiserum (See FIG. 6B). The exosomal fraction (See FIG. 6B, lane 2) contains ~50 kDa and 35 kDa proteins corresponding to different forms of DEK (See, e.g., Faulkner et al., J Biol Chem 276, 25804-12. (2001); McGarvey et al., J Cell Biol 150, 309-20. (2000), Fornerod et al., Oncogene 10, 1739-48 (1995); Sierakowska et al., Clin Exp Immunol 94, 435-9 (1993); Dong et al., Arthritis Rheum 41, 1505-10 (1998)). The 35 kDa form is a breakdown product lacking the N-terminus. The same bands are seen in the electrophoretic pattern of DEK in exosomes from the supernatant of purified, activated MDM (See FIG. 4A). DEK antibody does not recognize proteins in the exosome-free supernatant control (e.g., CD81-coated magnetic beads incubated with 500 µg of concentrated exosome-depleted supernatant, FIG. 4A, lane 1). As noted above, both the 50 kDa and the 35 kDa forms of DEK are physically associated with exosomes in synovial fluid macrophages from a child with JRA.

Having found DEK in the synovial fluids of JRA patients, it was then investigated whether DEK was released into the sera of patients with inflammatory arthritis. Serum concentrations of DEK in five healthy individuals and in pooled human AB serum were determined by a DEK antigen ELISA, and compared to DEK levels in JRA patient sera from a childhood arthritis repository (See FIG. 6C). DEK levels were found to be significantly higher in the sera from patients with JRA than in the serum from healthy volunteers, indicating that DEK is released into the circulation of patients with an ongoing autoimmune process.

Example 6

Modulation of DEK Secretion by Pro- and Anti-Inflammatory Factors

Figure 7:
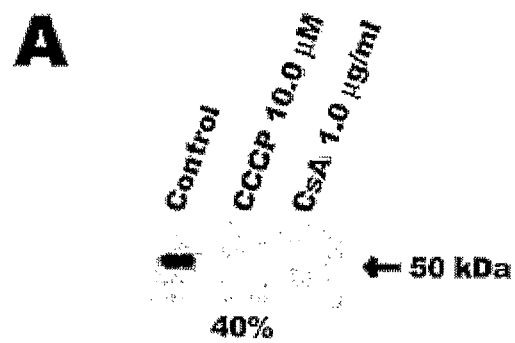
FIG. 7 shows DEK secretion by serum-differentiated MDM can be blocked by the immunosuppressive agents cyclosporin A and dexamethasone. (A). Day 12 serum-differentiated MDM were incubated in serum-free media alone for 12 h or in the presence of 10 μM carbonyl cyanide chlorophenyl hydrazone (CCCP) or 1 μg/ml cyclosporin A (CsA). (B). Day 11 serum-activated MDM were incubated in serum-free media for 12 h alone or in the presence of 0.5 μM or 1 μM dexamethasone. In A and B, secreted DEK was detected in the supernatant by Western blot using DEK-specific monoclonal antibody.
Figure 7:
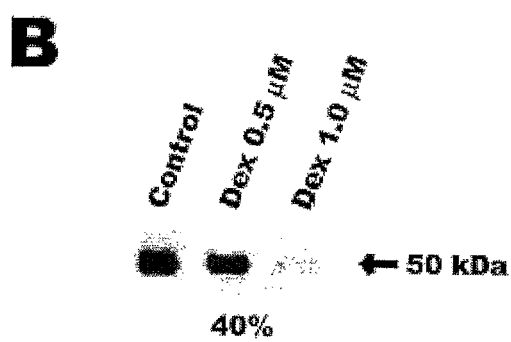

It was next determined whether DEK plays a direct role in inducing inflammation (e.g., if DEK is involved, immunosuppressive agents could be used to inhibit its secretion). As shown in FIG. 7A, secretion of DEK by day 12 serum-differentiated MDM can be blocked by CCCP, an inhibitor of mitochondrial respiration and inducer of apoptosis, and by cyclosporin A (CsA), a powerful immunosuppressive agent. Dexamethasone also inhibits DEK secretion in a dose-dependent fashion (See FIG. 7B) and causes DEK to accumulate inside the cell, indicating that clinically-employed immunosuppressive agents can be used to block the secretion of DEK.

The relatively constant timing of the onset of DEK secretion in relation to MDM development, in addition to the inhibition of DEK secretion by anti-inflammatory agents (e.g., dexamethasone and CsA) suggests that DEK secretion occurs in response to sequential effects of early and late inflammatory mediators. Thus, it was determined whether DEK may itself act as a pro-inflammatory molecule. To investigate this, an attempt was made to reproduce the cytokine/chemokine cascade that induces DEK's release from cultured macrophages. In order to assess the pro-secretion effect of cytokines, day 10 MDM growing in 10% human serum were used, rather than grown in 40% human serum, as the latter already maximally secrete DEK. MDM were treated with inflammatory mediators that are implicated in activation of monocytes, macrophages, and synovial macrophage-like cells, including TNF-α (5-100 ng/ml), IFN-γ (10-100 ng/ml), MCP-1 (monocyte chemoattractant protein-1) (10-100 ng/ml), and bioactive molecules such as lipopolysaccharide (LPS) (500-1000 ng/ml) alone and in combination with IFN-γ

Figure 8:
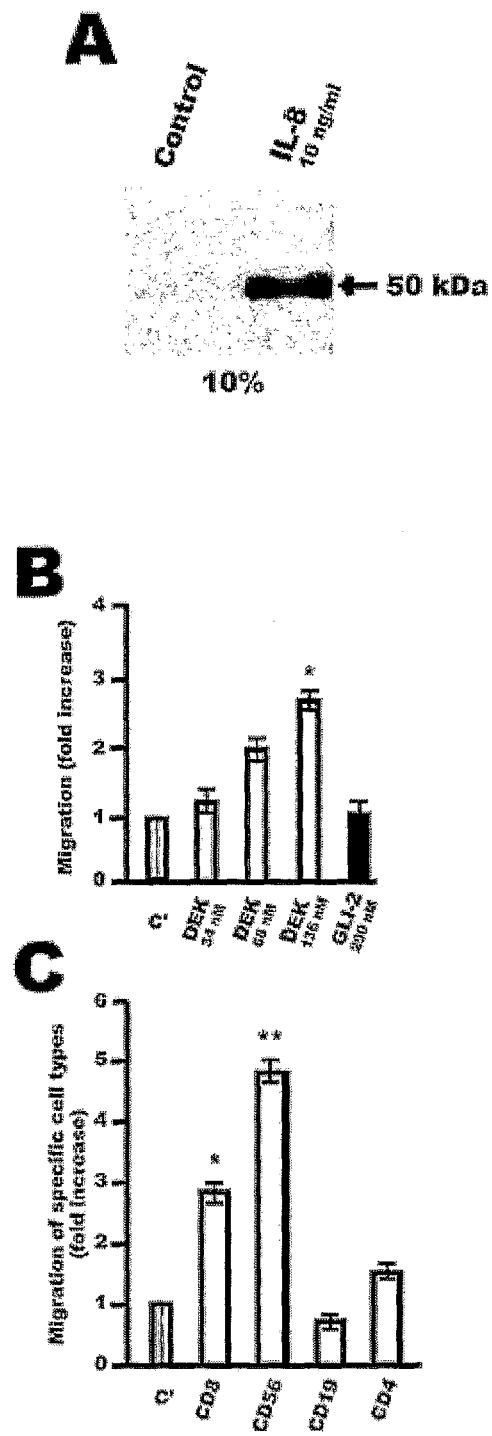
FIG. 8 shows DEK is a chemoattractant for monocyte-depleted peripheral white blood cells. (A). IL-8 induces the secretion of DEK from MDM. Day 12 MDM grown in 10% serum were maintained for 12 h in serum-free conditioned media alone or with 10 ng/ml of recombinant IL-8. Supernatants were harvested, and secreted DEK detected in the supernatant by Western blot using DEK-specific monoclonal antibody. (B). DEK is a chemoattractant. Monocyte-depleted peripheral white blood cells were prepared. $1 \times 10^5$ cells in 100 μl RPMI were placed in the upper chambers of a 24-well chemotaxis microchamber plate with pore size of 3 μM. Lower chambers contained RPMI medium with various concentrations of recombinant DEK (made in baculovirus), recombinant GLI-2 control protein (also made in baculovirus), or no protein control (C'). After 1 h, the number of fluorescently labeled migrating cells in the lower chamber was determined at 485 nM/535 nM wavelengths by Tecan GENios (Phenix, Austria). The results are expressed as the average fold increase of the number of cells migrating toward DEK or GLI-2 compared to control wells containing medium only. Data shown using 34 nM and 68 nM DEK are the average of three different donors, while data using 136 nM DEK are the average of six different donors. The increase in the migration of monocyte-depleted peripheral white blood cells toward 136 nM DEK vs. GLI-2 or no protein control is statistically significant (p=0.006). (C). DEK attracts $CD8^+$ T-cells and $CD56^+$ natural killer cells. Monocyte-depleted peripheral white blood cells were placed in the upper chamber of a 24-well chemotaxis microchamber plate with 5 μM pore size. Lower chambers contain either 79 nM of DEK in RPMI media or media alone. Cells were collected 1 hour after migration and double stained with immunofluorescent antibodies to $CD8^+$ (PE) and $CD4^+$ (FITC) or CD56 (PE) and CD19 (FITC). Fluorescence profiles were recorded by FACS analysis. The results are expressed as the average fold increase of the percentage of cells migrating toward DEK vs. control wells containing medium only. Migration of $CD8^+$ cells and $CD56^+$ cells towards DEK is statistically significant (*p=0.034 and **p=0.0028, respectively).

(See, e.g., Hayashida et al., Arthritis Res 3, 118-26 (2001); Gardella et al., EMBO Rep 3, 995-1001 (2002)). None of the inflammatory mediators listed above reproducibly stimulated DEK secretion by MDM. In contrast, IL-8 (10 ng/ml) was effective in stimulating vigorous secretion of DEK from day 12 MDM grown in 10% human serum (See FIG. 8A). As one of the major chemokines produced by synovial stromal cells, IL-8 plays an important role in attracting neutrophils and peripheral blood monocytes into the inflamed synovium (See, e.g., Hayashida et al., Arthritis Res 3, 118-26 (2001); Peichl et al., Scand J Immunol 34, 333-9 (1991); Verburgh et al., Clin Rheumatol 12, 494-9 (1993); Troughton et al., Br J Rheumatol 35, 1244-51 (1996)) providing an important link between DEK secretion and inflammatory joint disease.

Example 7

DEK Attracts Neutrophils Through Interactions with CXCR2/CXCR1

Figure 9:
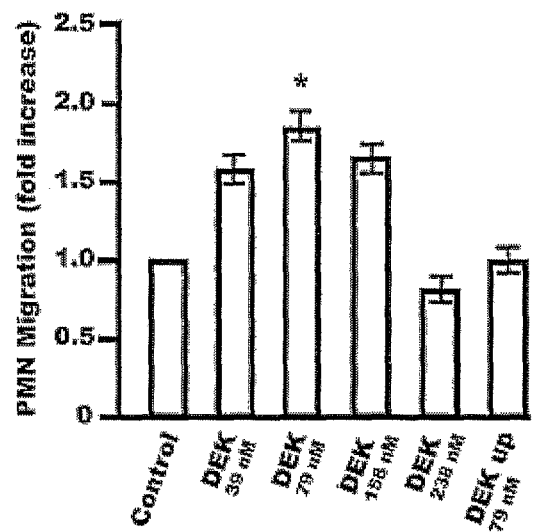
FIG. 9 shows DEK is a chemoattractant for neutrophils. (A). Purified neutrophils were placed in the upper chambers of a 24-well chemotaxis microchamber plate with pore size of 3 μM or 5 μM. Lower chambers contained RPMI medium with various concentrations of recombinant DEK, as indicated. The bar labeled "control" contained only media in the lower chamber. The bar labeled "DEK up" had DEK in the upper chamber and media in the lower chamber. The increase in neutrophil migration toward 79 nM DEK protein vs. control is statistically significant (p=0.0067). (B). Groups of mice received intraperitoneal injections of either PBS or 50 μg of either LPS, recombinant DEK, or a recombinant protein control prepared in parallel to DEK in baculovirus (an isoform of human GLI-2). Twenty mice were tested in each of the four groups. Half of the mice in each group were sacrificed after 4 hours (white bars), and the other half at 8 hours (black bars) after intraperitoneal injection, and then subjected to peritoneal lavage. The bars represent the average number of neutrophils migrating into the peritoneum of each group of mice. DEK significantly increased the infiltration of neutrophils as compared to the control protein human GLI-2 (p=0.011).
Figure 9:
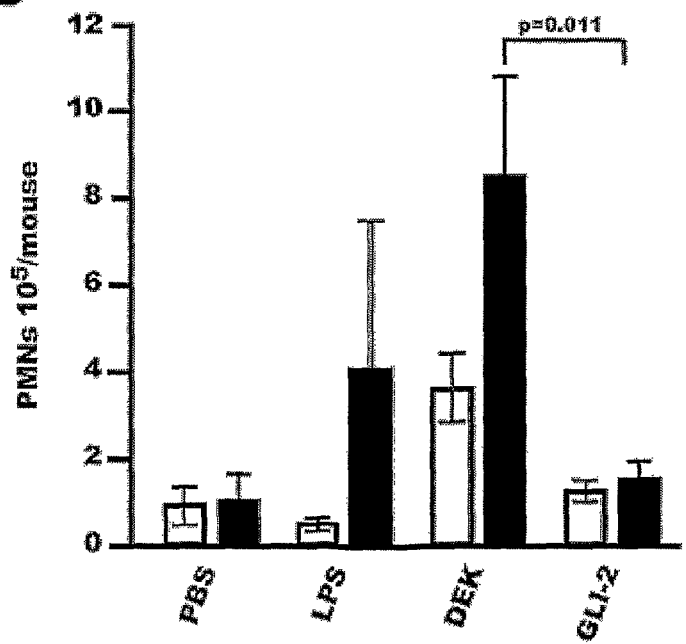

The ability of IL-8 to stimulate DEK secretion provoked the determination of whether DEK itself may have proinflammatory or chemotactic activity. Accordingly, full-length recombinant DEK protein produced in baculovirus was tested for its ability to attract Ficoll-purified peripheral white blood cells. Migration of these white blood cells toward DEK was observed to increase in a dose-dependent fashion (See FIG. 8B), reaching statistical significance (p<0.01) when migration toward the highest concentration of DEK (136 nM) is compared with migration toward control protein (a recombinant form of human GLI-2, See, e.g., Smith et al., J Virol 75, 2301-13 (2001)) or toward media alone. Similar results were seen with FLAG-tagged DEK protein purified from mammalian cells. Flow cytometry analysis identified $CD8^+$ T cells and $CD56^+$ natural killer cells migrating towards DEK (See FIG. 8C). Because DEK secretion can be stimulated by IL-8, a neutrophil chemoattractant, and because some of the migrating white blood cells also appeared morphologically to be neutrophils, it was determined whether DEK is also capable of attracting neutrophils. We found that purified fresh human neutrophils specifically migrate toward DEK in a dose-dependent manner, with a bell-shaped dose-response curve similar to that of IL-8 (See, e.g., Tani et al., Eur J Immunol 28, 502-7 (1998)) (See FIG. 9A).

In order to confirm that DEK is a chemoattractant, an in vivo murine model was used. Four groups of twenty 4-6 week old male C57BL6 mice were injected intraperitoneally with 50 µg of DEK, 50 µg of a recombinant control protein also prepared in baculovirus (GLI-2) (See, e.g., Smith et al., J Virol 75, 2301-13 (2001)), 50 µg of LPS, or PBS alone. In comparison to GLI-2 and PBS controls, differential white blood cell counts done on peritoneal lavage fluids showed that DEK significantly induces neutrophil migration into the peritoneum at 8 h following injection (p=0.011 in comparison to the GLI-2 control; See FIG. 9B). These results demonstrate that DEK acts as pro-inflammatory chemotactic factor similar to IL-8.

Figure 10:
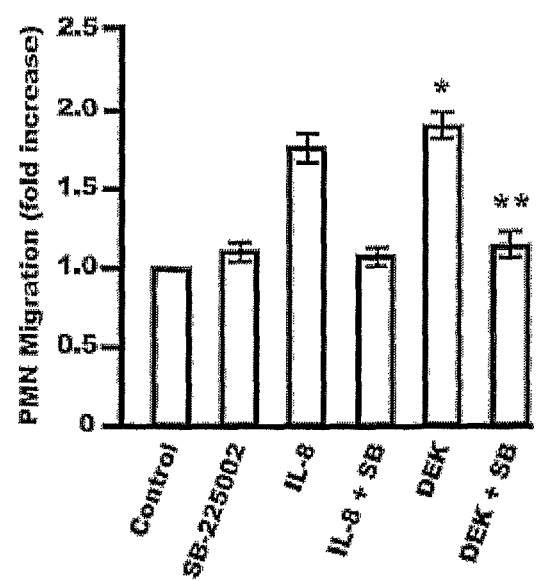
FIG. 10 shows that the CXCR2 receptor mediates DEK-induced neutrophil chemotaxis. Purified neutrophils (PMN) were treated with IL-8 (50 nM), the CXCR2 small molecule inhibitor SB225002 (3 μM), DEK (79 nM), IL-8 plus SB225002, or DEK plus SB225002 for 5 min at room temperature before and then during the migration assay. After 1 h, the number of fluorescently labeled migrating cells in the lower chamber was determined at 485 nM/535 nM wavelengths by Tecan GENios (Phenix, Austria). Migration of neutrophils towards DEK was again significantly increased in comparison to the control (*p=0.0067). SB225002 significantly blocked the migration of cells toward IL-8 and DEK. The migration toward DEK plus SB225002 vs. DEK alone is significantly lower (**p=0.0217). The results are expressed as the average fold increase in the number of cells migrating toward DEK compared to control wells containing medium only.

Although DEK has always been identified as a nuclear protein, an inspection of its amino acid sequence revealed an "ELR" (Glu-Leu-Arg) motif, an amino acid sequence found in specific CXC chemokines that are involved in chemotaxis and angiogenesis, for example, IL-8 and Gro-α (See, e.g., Strieter et al., J Biol Chem 270, 27348-57 (1995)). The ELR motif is important for the engagement and triggering of CXCR1 and CXCR2 receptors. Neutrophils, $CD8^+$ T cells, and natural killer cells all express CXCR1 and CXCR2 on their surface (See, e.g., Takata et al., J Immunol 173, 2231-5 (2004)), suggesting that DEK may bind to the same receptors. To determine if DEK binds to these receptors, the migration of neutrophils toward DEK in the presence of SB225002 (a small molecule that inhibits CXCR2 from binding to IL-8, See, e.g., White et al., J Biol Chem 273, 10095-8 (1998); Lane et al., J Virol 75, 8195-202 (2001)). was examined. Treatment with SB225002 results in virtually complete inhibition of neutrophil migration toward DEK and IL-8 (FIG. 10). Although SB225002 is selective for CXCR2 at low concentrations (See, e.g., White et al., J Biol Chem 273, 10095-8 (1998)), the concentration of SB225002 required to inhibit migration toward DEK is high enough that it may cause inhibition of CXCR1 as well as CXCR2. Taken together, these observations demonstrate that secreted DEK engages CXCR2/CXCR1, and thus attract lymphocytes, natural killer cells, and neutrophils to the synovial space, where they can propagate and/or amplify the inflammatory response.

Example 8

DEK Promotes Chemotaxis of Endothelial Cells Associated with Angiogenesis

DEK stimulates the chemotaxis of neutrophils via its interaction with CXCR2 and CXCR1 (See Example 7, above). It was hypothesized that this interaction is mediated by the interaction of DEK's ELR motif with these chemokine receptors, as is the case for the $ELR^+$ chemokines IL-8 and GRO-A. Engagement of these $ELR^+$ chemokines with CXCR1 and CXCR2 is known to induce chemotaxis of endothelial cells, and thus to be pro-angiogenic (See, e.g., Strieter et al., J Bio Chem 270:27348-27357, (1995)). As angiogenesis is a very important part of inflammatory arthritis, as well as being key to the pathogenesis of several of the malignancies characterized by increased expression of DEK, it was determined whether DEK is pro-angiogenic (See Example 8). Recombinant DEK was used in migration assays with Human Microvascular Endothelial Cells (HMVEC) in order to answer this query. As seen in FIG. 11, DEK does attract endothelial cells and thus possesses pro-angiogenic potential.

Example 9

A Lentiviral Vector Encoding Short Hairpin RNA (shRNA) Decreases DEK Expression

In order to further characterize DEK, a lentiviral vector system was constructed for the delivery short hairpin RNAs (shRNAs) designed to reduce DEK expression. One shRNA construct (See FIG. 12A) targeted only the 3' untranslated portion of DEK (e.g., thereby enabling the expression of DEK mutants encoded by a cDNA in cells as this shRNA does not degrade cDNAs). The lentiviral construct was developed using a described system (See, e.g., Li and Rossi, Methods in Enzymology 392: 218-226, 2005; Stewart et al., RNA 9:493-501, 2003). The shRNA-expressing vector was used to infect several different cell lines, and transduced cells were selected by GFP expression and analyzed for DEK expression using anti-DEK antibodies. The construct of FIG. 12A led to a >90% decrease in DEK expression (See FIG. 12C). A second construct was designed (See FIG. 12B) in which the initial shRNA of FIG. 12A was expressed, as well as another shRNA that targeted the coding region of DEK. As shown in FIG. 12C, this shRNA significantly decreased expression of DEK in multiple cell lines (e.g., estimated by microarray analysis to reduce DEK expression by approximately 99%). DEK expression measured by commercially available monoclonal antibody to DEK (BD Biosciences Pharmingen) showed complete elimination of DEK expression). However, probing with the polyclonal antibody to DEK as in FIG. 12C, showed that a small amount of DEK expression remained. Although an understanding of the mechanism is not necessary to practice the present invention and the present invention is not limited to any particular mechanism of action, in some embodiments, this quantitative difference is observed because the polyclonal antibody recognizes essentially all forms of DEK, whereas the monoclonal recognizes only the phosphorylated form of DEK. As the shRNA construct is in a lentivirus, it can be transduced into primary cells as well as cell lines (See, e.g., Stewart et al., RNA 9:493-501, 2003).

Example 10

DEK is Secreted in Cell Culture Supernatants from Retinoblastoma Cell Lines

Figure 13:
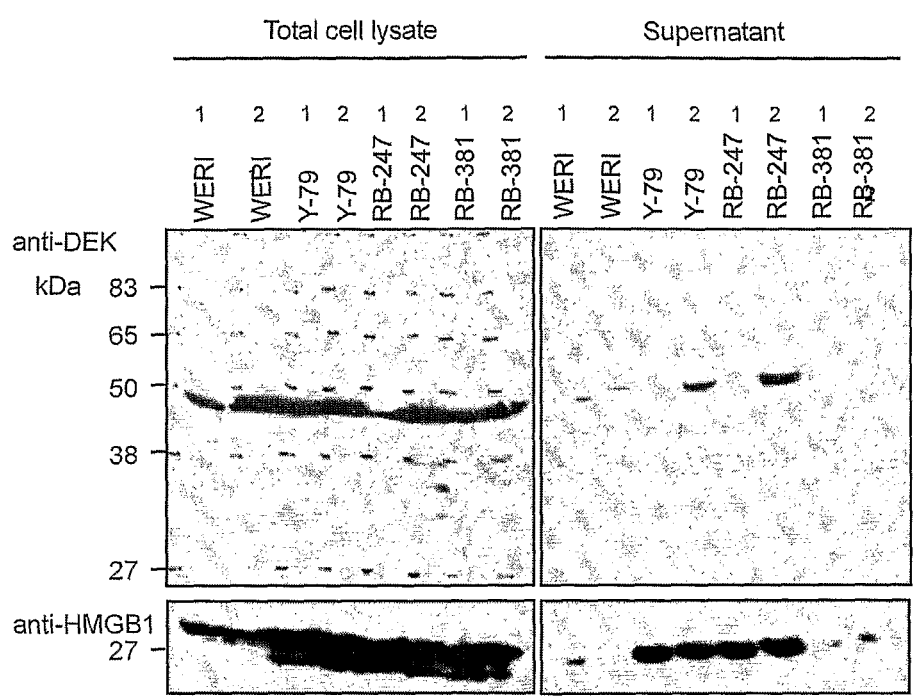
FIG. 13 shows Western blots from retinoblastoma cells and cell culture supernatants. Cell culture supernatants from different retinoblastoma cell lines analyzed for the presence of DEK show that DEK is found in supernatants of all investigated cell lines, with variation in amounts. HMGB1 is also present in the supernatants, but no vimentin, clearly showing that the observed DEK amounts are not due to necrotic cells.

Samples (total cell lysates and cell culture supernatants) representing $1 \times 10^6$ cells from different retinoblastoma cell lines (WERI, Y-79, RB247, RB381) were separated by SDS-PAGE and blotted onto nitrocellulose membranes. All samples were run in duplicates and were cut into stripes after the transfer. Individual stripes were incubated with two different DEK specific antibodies (1: monoclonal mouse, BD Bioscience and 2: a polyclonal rabbit antibody (K-877)). The same stripes were re-probed with a polyclonal antibody against HMGB1, and a monoclonal antibody against vimentin. As shown in FIG. 13, DEK is found in the supernatants of all cell lines, is predominantly present in the cell lines Y-79 and RB247, and is best recognized by polyclonal antibody. N-terminal degradation products of DEK were only visible with the polyclonal DEK antibody, because the monoclonal antibody only recognizes N-terminal parts of DEK. Also HMGB1 is present in high amounts in the supernatants of Y-79 and RB247. However no vimentin was detected in the supernatants of any investigated cells.

Example 11

Free DEK can be Taken Up by Cells

Figure 14:
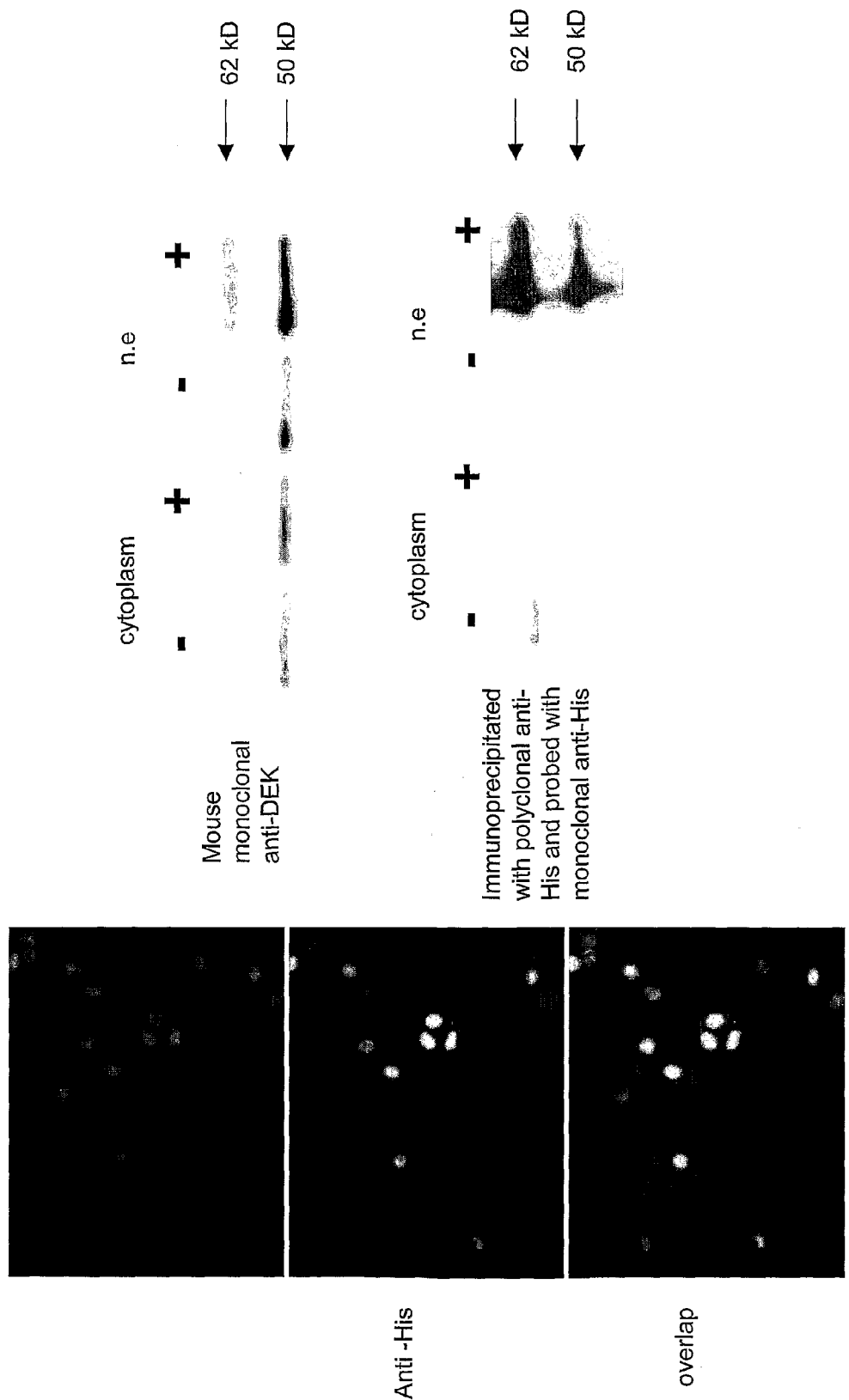
FIG. 14 shows that recombinant baculovirus His-tagged DEK protein is taken up by 12-day human MDM.

It was determined whether, similar to proteins like Tat of HIV, DEK might be taken up by cells and then act intracellularly. DEK possesses a signature five amino acid sequence (RKAKR) thought to be associated with the ability of a protein to be taken up/internalized by cells (See Crisanti, A; PCT/GB02/03027; United States Patent Office; Nov. 25, 2004, hereby incorporated by reference in its entirety). It was observed that recombinant DEK can be taken up by MDM (See FIG. 14) and HeLa cells.

Example 12

Figure 15:
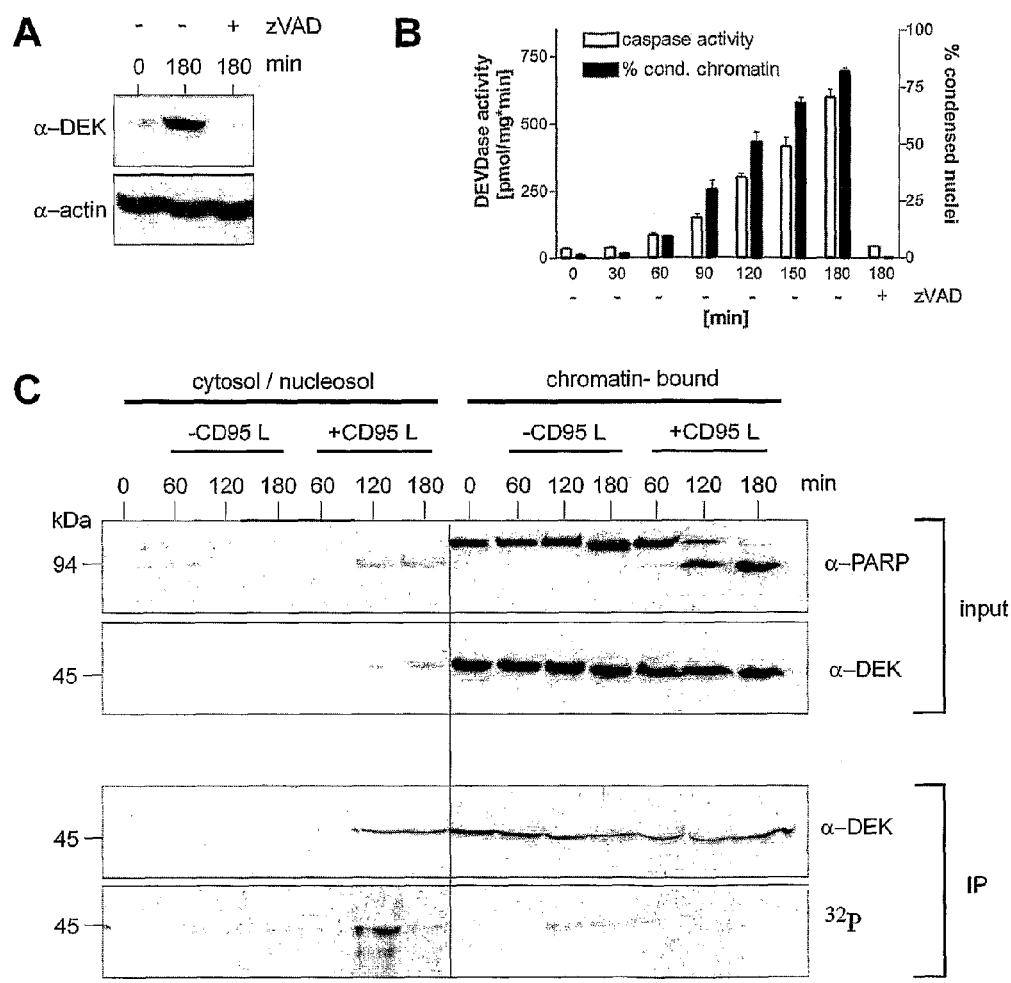
FIG. 15 shows that DEK is released from the nucleus in Fas-L (CD95 L) induced apoptosis in a highly phosphorylated manner in vivo.

Apoptosis of T Cells Releases a Highly Phosphorylated, Ubiquitinated, and Polyribosylated Form of DEK into the Cytoplasm As described herein, DEK can be released from the nucleus and into the cytoplasm, and even secreted, in MDM. This process did not involve apoptosis. However, the present invention also provides that in Jurkat T cells DEK can also be released into the cytoplasm as the result of Fas Ligand-mediated apoptosis (See FIG. 15). The caspase inhibitor ZVAD blocks release of DEK into the cytoplasm, confirming that it is apoptosis that is responsible for this release (See FIGS. 15A and 15B). The fraction of DEK that is released is highly phosphorylated (See FIG. 15C). The "smear" seen in the band containing the cytoplasmic DEK suggested ubiquitination of DEK, and Western blots and co-immunoprecipitation of ubiquitin and DEK further demonstrated that DEK is a target for ubiquitination. Thus, the present invention provides that DEK, that contains 67 lysines, is a target for both acetylation and ubiquitination.

Figure 16:
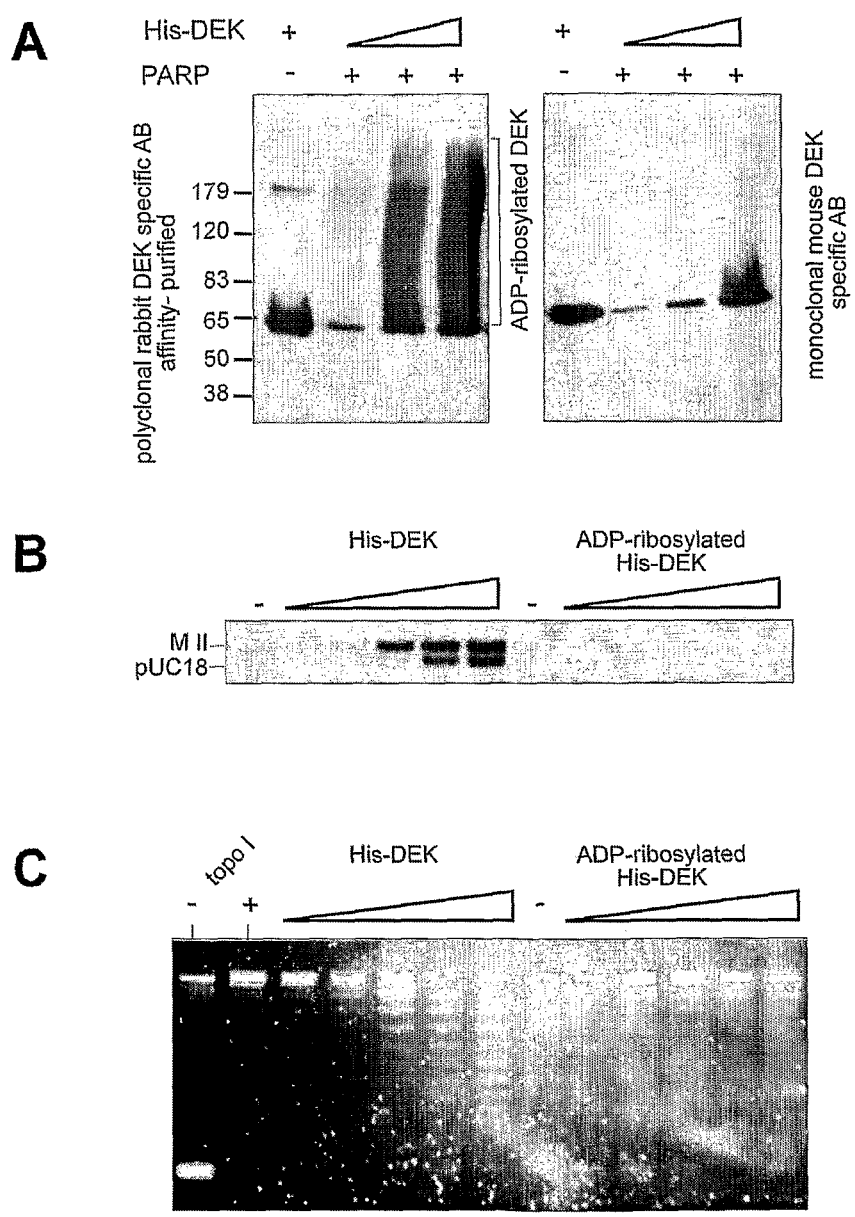
FIG. 16 shows (A) ADP-ribosylation of DEK in vitro; (B) aggregation assay with ADP-ribosylated DEK; and (C) topology assay with ADP-ribosylated DEK.

Polyribosylation is another significant post-translational modification that would produce a smear as seen in FIG. 15C, left-hand panel. Polyribosylation also takes place on lysines, as well as on glutamic and aspartic acid residues. Interestingly, polyribosylation is known to affect DNA replication, an important function of DEK. As shown in FIG. 16, the fraction of DEK released into the cytoplasm of Jurkat cells following apoptosis is polyribosylated. Further, polyribosylation of DEK inhibits its ability to bind to DNA and alter chromatin structure (See FIG. 16), signifying that this post-translational modification is functionally significant.

Example 13

ALY Interacts with DEK

Figure 17:
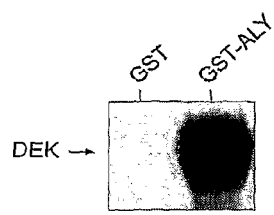
FIG. 17 shows ALY-DEK interaction (A) GST-pull down; (B) aggregation assay; and (C) EMSA with purified HIS-DEK and GST-ALY.
Figure 17:
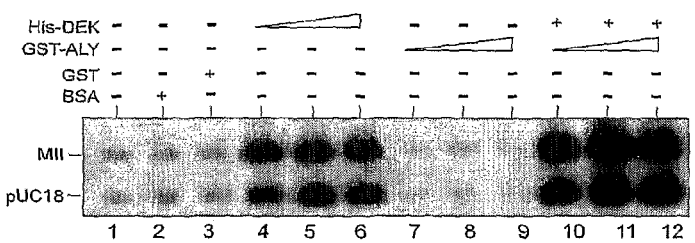
Figure 17:
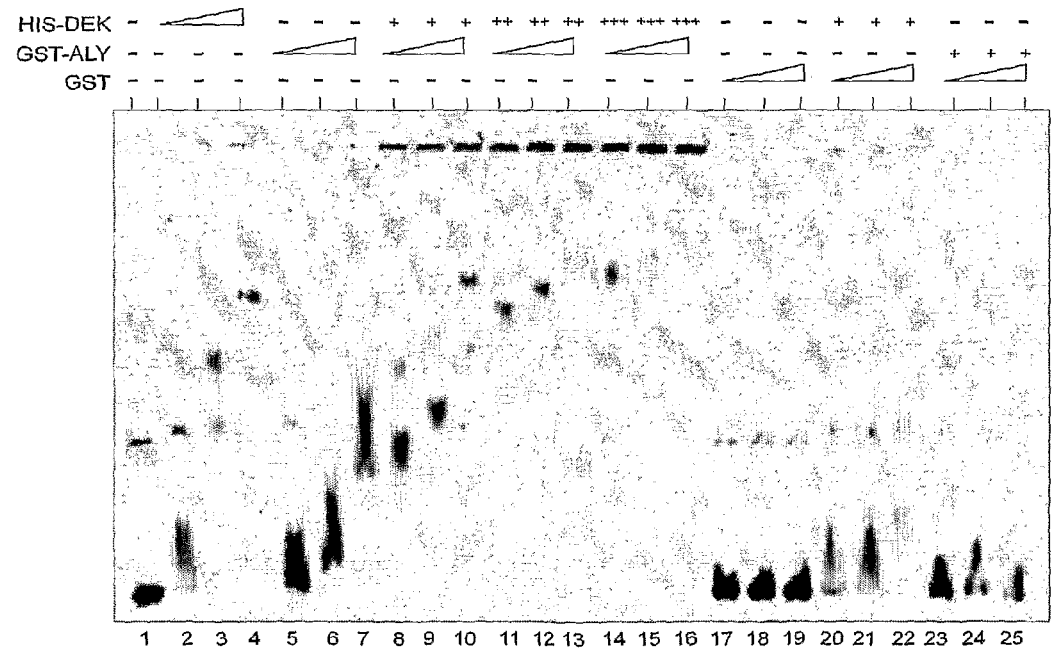

Experiments were conducted during development of the present invention to determine whether one interacting factor for DEK might be ALY, a protein initially identified as a co-factor for DNA binding and later shown to be involved in RNA export from the nucleus (See, e.g., Bruhn et al., Genes & Dev. 11:640-653, 1997; Gatfield and Izaurraide, J Cell Biol 159(4):579-588, 2002; Maniatis and Reed, Nature 416:499-506, 2002). GST pull-down assays were used, demonstrating that ALY and DEK can directly interact (See FIG. 17A). It was then determined whether ALY could influence DEK DNA binding. Using both aggregation assays and EMSA (See FIGS. 17B and 17C), it was observed that ALY clearly augments the ability of DEK to bind to DNA. In view of previous literature suggesting that ALY does not on its own bind to DNA (See, e.g., Bruhn et al., Genes & Dev. 11:640-653, 1997), it was surprising to observe that ALY, like DEK, was also able to bind DNA independently.

Figure 18:
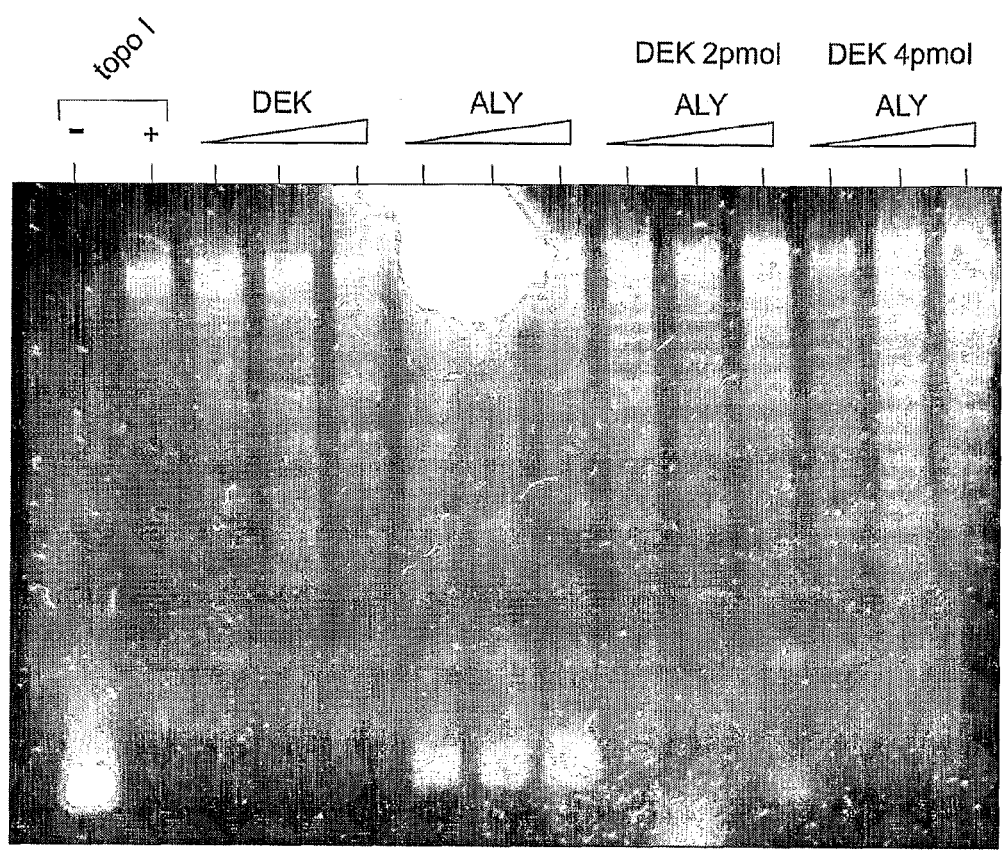
FIG. 18 shows topology assay with His-DEK and GST-ALY.

Having observed that DEK and ALY interact in DNA binding, it was next determined whether this might have functional ramifications. One reliable biochemical function of DEK is its ability to alter DNA topology by introducing positive supercoils. Thus, it was determined if ALY could alter DEK's functionality in this regard. As shown in FIG. 18, DEK induced supercoiling. Unexpectedly, ALY, which prior to the present invention had not been shown to independently bind DNA or influence DNA topology, was also able to induce supercoiling. Even more unexpected, ALY antagonized the ability of DEK to induce supercoils. Although an understanding of the mechanism is not necessary to practice the present invention and the present invention is not limited to any particular mechanism of action, in some embodiments, whereas DEK induces positive supercoils, ALY may introduce negative supercoils.

Example 14

DEK Knock-Down Cells have Less Compacted Chromatin

Figure 19:
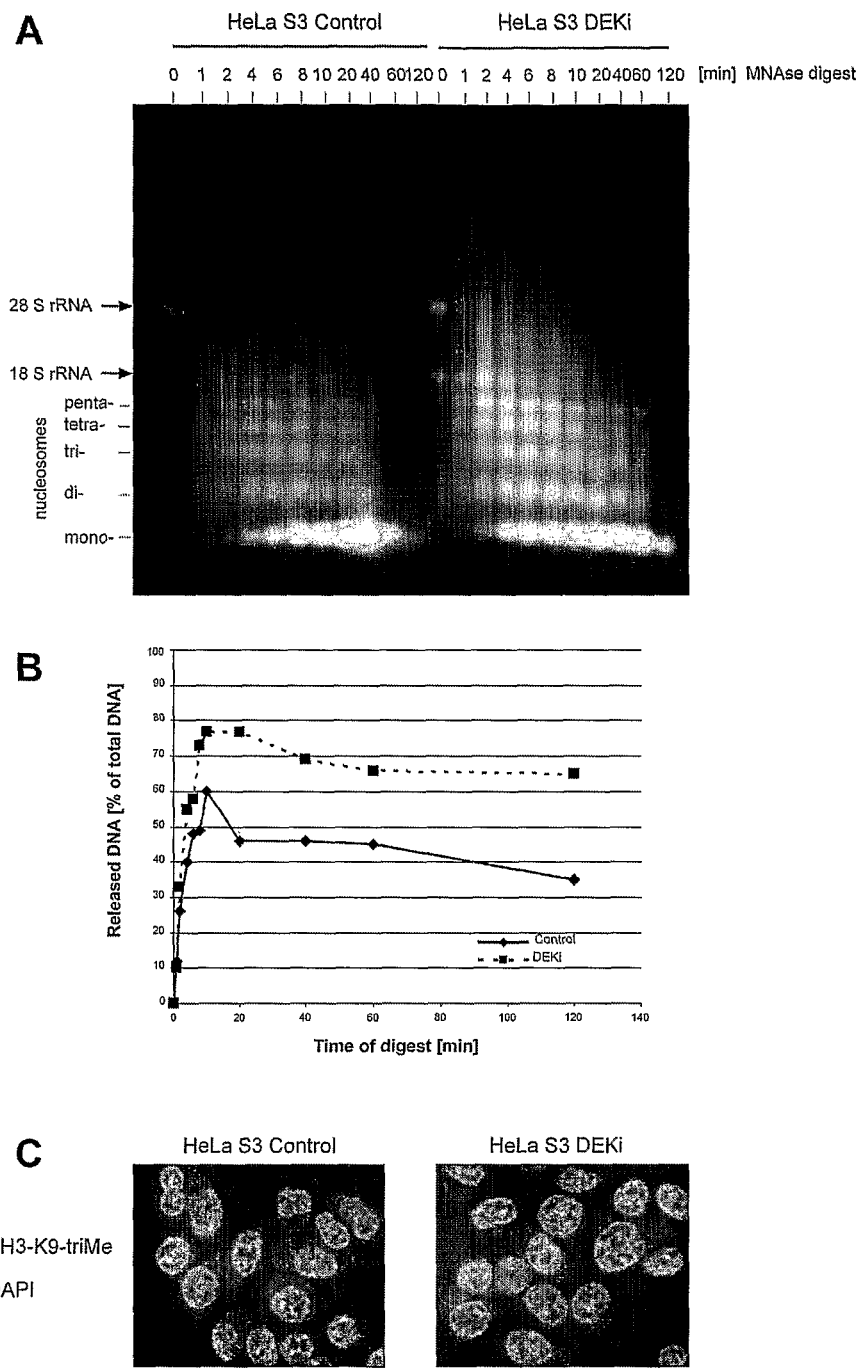
FIG. 19 shows DEK knock-down cells have less compacted chromatin.

While DEK has been implicated in several cellular processes, perhaps the strongest evidence to date has suggested a role for DEK in chromatin remodeling. DEK has been shown in vitro to induce positive supercoils to DNA, and thus diminished levels of DEK in a cell should result in more globally relaxed chromatin. This would then potentially have ramifications for DNA replication and transcription, and could affect sensitivity to DNA-damaging agents. To investigate this further, the nuclei of control HeLa cells and DEK knock-down HeLa cells were stained using an antibody that recognizes heterochromatin, and found that they had less heterochromatin than did the wild-type cells (FIG. 19C). To further confirm that DEK knock-down cells had a more open chromatin structure, a micrococcal nuclease analysis was performed of the wild-type and DEK knock-down cells. As shown in FIGS. 19A and 19B, the DNA from the DEK knock-down cells was considerably more sensitive to micrococcal nuclease, indicating that the chromatin has a more open structure in these cells. Thus, not only can DEK influence chromatin remodeling in vitro, but in vivo DEK is a crucial protein controlling this process.

Example 15

Figure 20:
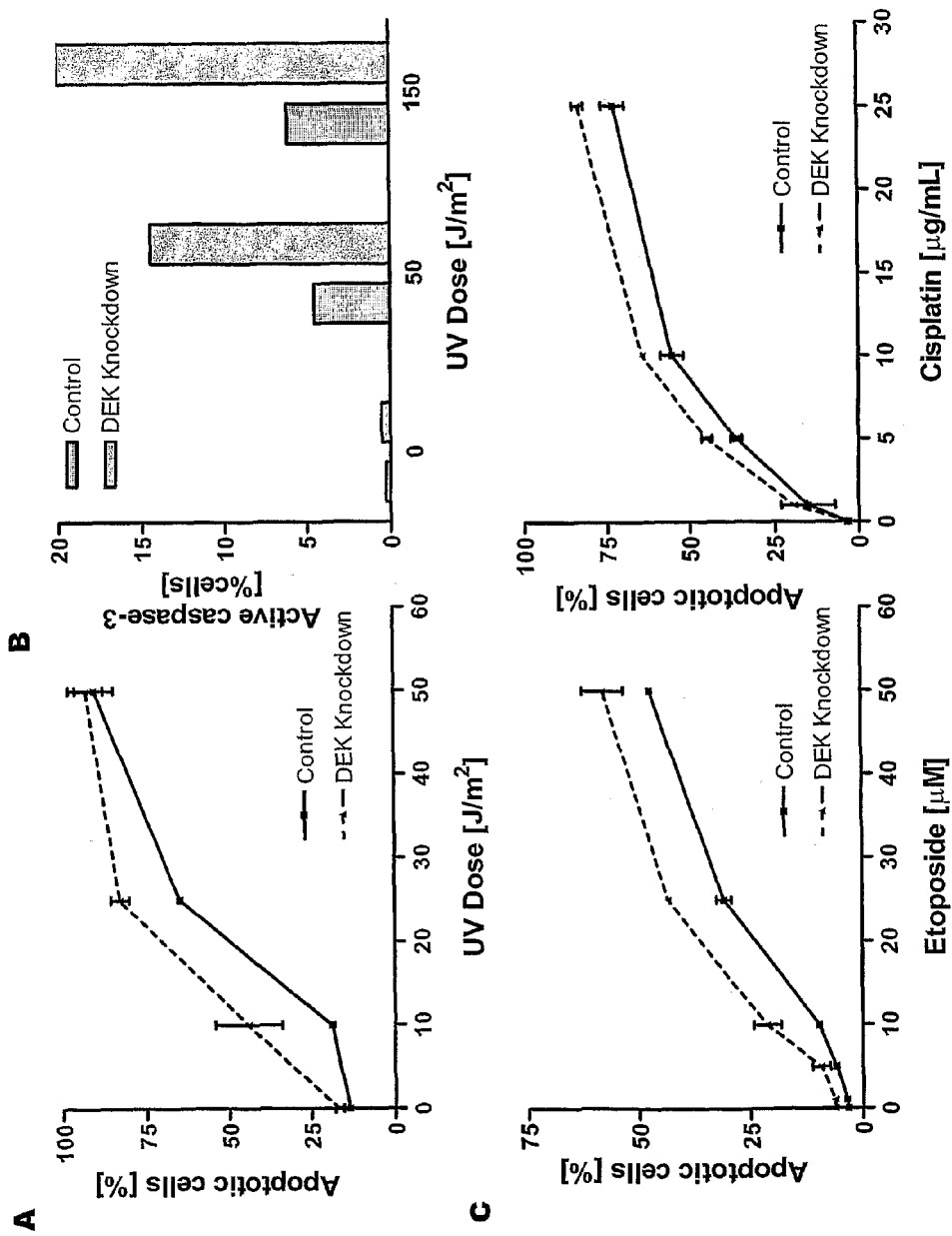
FIG. 20 shows DEK knockdown sensitizes cells to DNA damaging agents.

DEK Knock-Down Cells are More Sensitive to Ultraviolet (UV) Radiation and Other DNA-Damaging Agents The observation that DEK knock-down cells have less compacted chromatin suggested that the DNA of such cells might be more susceptible to specific types of damage. Indeed, UV radiation of either Jurkat cells (FIG. 20A) or HeLa cells (FIG. 20B) led to a significant increase in apoptosis in the DEK knock-down cells as compared to control cells in which only the empty lentiviral vector had been transduced. DEK knock-down cells were also consistently more sensitive to other DNA damaging agents, such as the antineoplastic agents cisplatinum and etoposide (See FIG. 20C). Thus, lack of DEK leads to an open chromatin configuration that might be responsible for increased sensitivity to UV radiation and other DNA damaging agents.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A method of treatment for rheumatoid arthritis comprising administering to a subject having rheumatoid arthritis a composition comprising a DEK inhibitor under conditions such that the expression of DEK is reduced in said subject wherein said DEK inhibitor is an anti-DEK antibody.

2. The method of claim 1, wherein said anti-DEK antibody is a monoclonal antibody.

3. The method of claim 1, wherein said anti-DEK antibody is a polyclonal antibody.

4. The method of claim 1, wherein said rheumatoid arthritis is juvenile rheumatoid arthritis (JRA).

5. The method of claim 1, wherein the antibody inhibits chemotaxis of cells in the subject.

6. The method of claim 5, wherein said anti-DEK antibody is a monoclonal antibody.

7. The method of claim 5, wherein said anti-DEK antibody is a polyclonal antibody.

8. The method of claim 5, wherein said antibody reduces activity and/or function of DEK.

9. The method of claim 8, wherein said antibody inhibits chemotaxis of neutrophils, CD8+ T cells, and NK cells.

* * * * *

UNITED STATES PATENT AND TRADEMARK OFFICE
CERTIFICATE OF CORRECTION

PATENT NO.       : 8,652,467 B2
APPLICATION NO. : 12/090164
DATED            : February 18, 2014
INVENTOR(S)      : Markovitz et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1502 days.

Signed and Sealed this
Twenty-ninth Day of September, 2015

Michelle K. Lee
*Director of the United States Patent and Trademark Office*